US007598029B2

(12) United States Patent
Geese et al.

(10) Patent No.: US 7,598,029 B2
(45) Date of Patent: Oct. 6, 2009

(54) METHOD FOR IDENTIFYING HIV-1 PROTEASE INHIBITORS WITH REDUCED METABOLIC AFFECTS

(75) Inventors: William J. Geese, Doylestown, PA (US); Koustubh Ranade, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/317,322

(22) Filed: Dec. 22, 2008

(65) Prior Publication Data
US 2009/0117535 A1     May 7, 2009

Related U.S. Application Data

(62) Division of application No. 11/823,707, filed on Jun. 27, 2007.
(60) Provisional application No. 60/817,846, filed on Jun. 30, 2006.

(51) Int. Cl.
*C12Q 1/00*     (2006.01)
(52) U.S. Cl. .......................................................... 435/4
(58) Field of Classification Search ........................ None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 5,837,832 | A | 11/1998 | Chee et al. |
| 5,849,911 | A | 12/1998 | Fässler et al. |
| 5,856,104 | A | 1/1999 | Chee et al. |
| 5,856,174 | A | 1/1999 | Lipshutz et al. |
| 5,858,659 | A | 1/1999 | Sapolsky et al. |
| 5,874,219 | A | 2/1999 | Rava et al. |
| 6,087,383 | A | 7/2000 | Singh et al. |
| 6,440,707 | B1 | 8/2002 | Kwok et al. |
| 6,458,540 | B1 | 10/2002 | Ramberg |
| 2005/0256202 | A1 | 11/2005 | Kim et al. |

FOREIGN PATENT DOCUMENTS

| WO | WO89/11548 | 11/1989 |
| WO | WO93/22456 | 11/1993 |
| WO | WO95/11995 | 5/1995 |
| WO | WO99/07865 | 2/1999 |
| WO | WO00/64920 | 11/2000 |

OTHER PUBLICATIONS

SNP Cluster Report: RS3219177, Entry Date Jul. 2, 2002.
Kamin, et al., "Resistin Levels in Human Immunodeficiency Virus-Infected Patients with Lipoatrophy Decrease in Response to Rosiglitazone", J. Clin. Endocrinology & Metabolism, vol. 90 (6), pp. 3423-3426 (2005).
Ranade, et al., "A Single Nucleotide Polymorphism in the Resistin Gene Is Associated with Adverse Metabolic Changes on HAART: An Exploratory Pharmacogenetic Association Study of A5005s, the Metabolic Sub-study of ACTG 384", 13th Conference on Retroviruses and Opportunistic Infections, Feb. 5, 2006, Session 131—"Genomic Mechanisms of Metabolic Complications".
Adeghate, E., "An update on the biology and physiology of resistin", Cell. Mol. Life Sci., vol. 61, pp. 2485-2496 (2004).
Alderborn, A., "Determination of Single-Nucleotide Polymorphisms by Realtime Pyrophosphate DNA Sequencing", Genome Research, vol. 10, pp. 1249-1258 (2000).
Armstrong, B. et al., "Suspension Arrays for High Throughput, Multiplexed Single Nucleotide Polymorphism Genotyping", Cytometry, vol. 40, pp. 102-108 (2000).
Ausubel, F. et al., "Hybridization Analysis of DNA Blots", Current Protocols in Molecular Biology, vol. 1, pp. 2.10.1-2.10.16 (1995).
Ausubel, F. et al., "Directed Mutagenesis Using the Polymerase Chain Reaction", Current Protocols in Molecular Biology, vol. 1, pp. 8.5.1-8.5.9 (1995).
Azuma, K. et al., "Novel Resistin Promoter Polymorphisms: Association with Serum Resistin Level in Japanese Obese Individuals", Horm Metab Res., vol. 36, pp. 564-570 (2004).
Banér, J. et al., "More keys to padlock probes: mechanisms for high-throughput nucleic acid analysis", Current Opinion in Biotechnology, vol. 12, pp. 11-15 (2001).
Banér, J. et a., "Signal amplification of padlock probes by rolling circle replication", Nucleic Acids Research, vol. 26(22), pp. 5073-5078 (1998).
Banerjee, R. et al., "Resistin: molecular history and prognosis", J. Mol. Med., vol. 81, pp. 218-226 (2003).
Banerjee, R. et al., "Regulation of Fasted Blood Glucose by Resistin", Science, vol. 303, pp. 1195-1198 (2004).
Bartlett, R. et al., "In vivo targeted repair of a point mutation in the canine dystrophin gene by a chimeric RNA/DNA oligonucleotide", Nature Biotechnology, vol. 18, pp. 615-622 (2000).
Beaudet, L. et al., "Homogeneous Assays for Single-Nucleotide Polymorphism Typing Using AlphaScreen", Genome Research, vol. 11, pp. 600-608 (2001).
Bennett, M. et al., "Correspondence Between a Mammalian Spliceosome Component and an Essential Yeast Splicing Factor", Science, vol. 262, pp. 105-108 (1993).

(Continued)

*Primary Examiner*—Gary B Nickol
*Assistant Examiner*—Nicole Kinsey White
(74) *Attorney, Agent, or Firm*—Stephen C. D'Amico

(57) ABSTRACT

The invention provides a novel in vitro method for identifying HIV-1 protease inhibitors with reduced potential for inducing metabolic abnormalities. The invention further provides diagnostic methods for identifying patients who may be at risk of developing metabolic abnormalities subsequent to the administration of an HIV-1 protease inhibitor. The invention also provides novel polynucleotides associated with the incidence of HIV-1 protease inhibitor induced metabolic abnormalities. The invention also provides polynucleotide fragments corresponding to the genomic and/or coding regions of these polynucleotides which comprise at least one polymorphic locus per fragment. Allele-specific primers and probes which hybridize to these regions, and/or which comprise at least one polymorphic locus are also provided. The polynucleotides, primers, and probes of the present invention are useful in phenotype correlations, medicine, and genetic analysis. The invention further relates to diagnostic methods for using these novel polynucleotides in the diagnosis, treatment, and/or prevention of HIV-1 protease inhibitor induced metabolic abnormalities.

8 Claims, 7 Drawing Sheets

OTHER PUBLICATIONS

Figure 1:
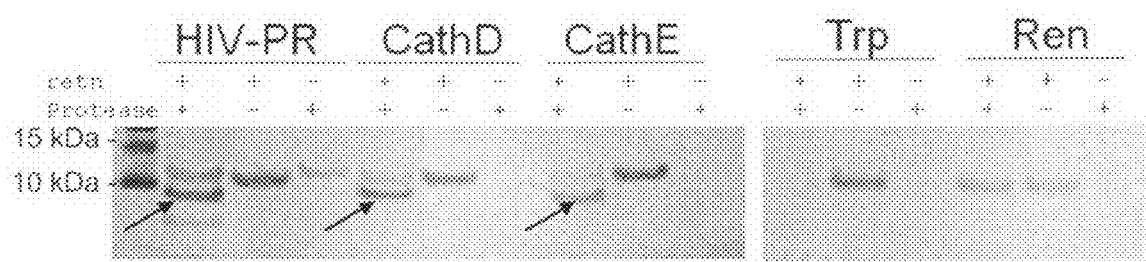

Berg, J. et al., "Lessons from Zinc-binding Peptides", Annu. Rev. Biophys. Biomol. Struct., vol. 26, pp. 357-371 (1997).
Bouchie, A. et al., "Confirmant to sell protein data" Business and Regulatory News, Nature Biotechnology, vol. 19, pp. 703-705 (2001).
Bray, M. et al., "High-Throughput Multiplex SNP Genotyping with MALDI-TOF Mass Spectrometry: Practice, Problems and Promise", Human Mutation, vol. 17, pp. 296-304 (2001).
Brown, P. et al., "Exploring the new world of the genome with DNA microarrays", Nature Genetics supplement, vol. 21, pp. 33-37 (1999).
Cai, H. et al., "Flow Cytometry-Based Minisequencing: A New Platform for High-Throughput Single-Nucleotide Polymorphism Scoring", ERRATUM, Genomics, vol. 69, pp. 395 (2000).
Calza, L. et al., "Dyslipidaemia associated with antiretroviral therapy in HIV-infected patients", J. of Antimicrobial Chemotherapy, vol. 53, pp. 10-14 (2004).
Cargill, M. et al., "Characterization of single-nucleotide polymorphisms in coding regions of human genes", Nature genetics, vol. 22, pp. 231-238 (1999).
Carr, A., "HIV Protease Inhibitor-Related Lipodystrophy Syndrome", Clinical Infectious Diseases, vol. 30(Suppl 2), pp. S135-S142 (2000).
Carr, A., "HIV lipodystrophy: risk factors, pathogenesis, diagnosis and management", AIDS, vol. 17(suppl 1), pp. S141-S148 (2003).
Chan, W. et al., Quantum Dot Bioconjugates for Ultrasensitive Nonisotopic Detection, Science, vol. 281, pp. 2016-2018 (1998).
Chen, X. et al., "Fluorescence energy transfer detection as a homogeneous DNA diagnostic method", PNAS, vol. 94, pp. 10756-10761 (1997).
Chen, J. et al., "A Microsphere-Based Assay for Multiplexed Single Nucleotide Polymorphism Analysis Using Single Base Chain Extension", Genome Research, vol. 10, pp. 549-557 (2000).
Chen, X. et al., "Fluorescence Polarization in Homogeneous Nucleic Acid Analysis", Genome Research, vol. 9, pp. 492-498 (1999).
Cho, Y. et al., "Common genetic polymorphisms in the promoter of resistin gene are major determinants of plasma resistin concentrations in humans", Diabetolgia, vol. 47, pp. 559-565 (2004).
Chou, K.C. et al., "Predicting Human Immunodeficiency Virus Protease Cleavage Sites in Proteins by a Discriminant Function Method", Proteins: Structure, Function, and Genetics, vol. 24, pp. 51-72 (1996).
Clark, A. et al., "Haplotype Structure and Population Genetic Inferences from Nucleotide-sequence Variation in Human Lipoprotein Lipase", Am. J. Hum. Genet., vol. 63, pp. 595-612 (1998).
Clark, A., "Inference of Haplotypes from PCR-amplified Samples of Diploid Populations", Mol. Biol. Evol., vol. 7(2), pp. 111-122 (1990).
Cohen, C. et al., "Comparison of atazanavir with lopinavir/ritonavir in patients with prior protease inhibitor failure: a randomized multinational trial", Current Medical Research and Opinions, vol. 21(10), pp. 1683-1692 (2005).
Conneely, K. et al., "Variation in the resistin gene is associated with obesity and insulin-related phenotypes in Finnish subjects", Diabetologia, vol. 47, pp. 1782-1788 (2004).
Criqui, M., "Triglycerides and cardiovascular disease", European Heart Journal, vol. 19, Supplement A, pp. A36-A39 (1998).
Dash, C. et al., "Aspartic Peptidase Inhibitors: Implications in Drug Development", Critical Reviews in Biochemistry and Molecular Biology, vol. 38(2), pp. 89-119 (2003).
Deutscher, M., "Guide to Protein Purification, Methods in Enzymology, vol. 182, Academic Press Inc, (1990).
Dong, S. et al., "Flexible use of High-Density Oligonucleotide Arrays for Single-Nucleotide Polymorphism Discovery and Validation", Genome Research, vol. 11, pp. 1418-1424 (2001).
Dubé, M. et al., "Glucose metabolism, lipid, and body fat changes in antiretroviral-naïve subjects randomized to nelfinavir or efavirenz plus dual nucleosides", AIDS, vol. 19, pp. 1807-1818 (2005).
Eckert, PCR Methods and Applications, Cold Spring Harbor Laboratory Press, (1991).
Egholm, M. et al., "PNA hybridizes to complementary oligonucleotides obeying the Watson-Crick hydrogen-bonding rules", Nature, vol. 365, pp. 566-568 (1993).
Engert, J. et al., "5' Flanking Variants of Resistin are associated with Obesity", Diabetes, vol. 51, pp. 1629-1634 (2002).
Erlich, H., "Principles and Applications for DNA Amplification", PCR Technology, Stockton Press, (1989).
Erlich, H. et al., "Recent Advances in the Polymerase Chain Reaction", Science, vol. 252, pp. 1643-1651 (1991).
Excoffier, L. et al., "Maximum-Likelihood Estimation of Molecular Haplotype Frequencies in a Diploid Population", Mol. Bio. Evol., vol. 12(5), pp. 921-927 (1995).
Fallin, D. et al., "Accuracy of Haplotype Frequency Estimation for Biallelic Loci, via the Expectation-Maximization Algorithm for Unphased Diploid Genotype Data", Am. J. Hum. Genet., vol. 67, pp. 947-959 (2000).
Fan, J. et al., "Parallel Genotyping of Human SNPs using Generic High-density Oligonucleotide Tag Arrays", Genome Research, vol. 10, pp. 853-860 (2000).
Faruqi, F. et al., "High-throughput genotyping of single nucleotide polymorphisms with rolling circle amplification", BMC Genomics, vol. 2:4 (2001).
Fisac, C. et al., "A Comparison of the Effects of Nevirapine and Nelfinavir on Metabolism and Body Habitus in Antiretroviral-Naïve Human Immunodeficiency Virus-Infected Patients: A Randomized Controlled Study", The J. of Clinical Endocrinology & Metabolism, vol. 88(11), pp. 5186-5192 (2003).
Fullerton, S. et al., "Apolipoprotein E Variation at the Sequence Haplotype Level: Implications for the Origin and Maintenance of a Major Human Polymorphism" Am. J. Hum. Genet., vol. 67, pp. 881-900 (2000).
Fulton, R. et al., "Advanced multiplexed analysis with the FlowMetrix™ system", Clinical Chemistry, vol. 43(9), pp. 1749-1756 (1997).
Gao, J. et al., "Changes in the Protein Expression of Yeast as a Function of Carbon Source", Journal of Proteome Research, vol. 2, pp. 643-649 (2003).
Gao, J. et al., "Identification of in vitro protein biomarkers of idiosyncratic liver toxicity", Toxicology in Vitro, vol. 18, pp. 533-541 (2004).
Gerry, N. et al., "Universal DNA Microarray Method for Multiplex Detection of Low Abundance Point Mutations", J. Mol. Biol., vol. 292, pp. 251-262 (1999).
Gibbs, R. et al., "Detection of single DNA base differences by competitive oligonucleotide priming", Nucleic Acids Research, vol. 17(7), pp. 2437-2448 (1989).
Gibson, N. et al., "A homogeneous method for genotyping with fluorescence polarization", Clinical Chemistry, vol. 43(8), pp. 1336-1341 (1997).
Goldsmith, D. et al., "Atazanavir: Adis Drug Profile", Drugs, vol. 63(16), pp. 1679-1693 (2003).
Gray, W.R., "Disulfide structures of highly bridged peptides: A new strategy for analysis", Protein Science, vol. 2, pp. 1732-1748 (1993).
Griffin, T. et al., "Direct genetic analysis by matrix-assisted laser desorption/ionization mass spectrometry", PNAS, vol. 96, pp. 6301-6306 (1999).
Griffin, T. et al., "Genetic analysis by peptide nucleic acid affinity MALDI-TOF mass spectrometry", Nature Biotechnology, vol. 15, pp. 1368-1372 (1997).
Griffin, T. et al., "Single-nucleotide polymorphism analysis by MALDI-TOF mass spectrometry", Trends Biotechnology, vol. 18, pp. 77-84 (2000).
Grinspoon, S. et al., "Cardiovascular Risk and Body-Fat Abnormalities in HIV-Infected Adults", The New England Journal of Medicine, vol. 352(1), pp. 48-62 (2005).
Grüninger-Leitch, F. et al., "Substrate and Inhibitor Profile of BACE (β-Secretase) and Comparison with Other Mammalian Aspartic Proteases", The J. of Biological Chemistry, vol. 277(7), pp. 4687-4693 (2002).
Guatelli, J. et al., "Isothermal, in vitro amplification of nucleic acids by a multienzyme reaction modeled after retroviral replication", PNAS, vol. 87, pp. 1874-1878 (1990).

Gut, I., "Automation in Genotyping of Single Nucleotide Polymorphisms", Human Mutation, vol. 17, pp. 475-492 (2001).
Gutiérrez, F. et al., Lipid Abnormalities in HIV-Infected Patients and Lopinavir Plasma Concentrations, J. Acquir Immune Defic Syndr., vol. 36(5), pp. 1107-1108 (2004).
Hacia, J., "Resequencing and mutational analysis using oligonucleotide microarrays", Nature genetics supplement, vol. 21, pp. 42-47 (1999).
Haff, L. et al., "Single-Nucleotide Polymorphism Identification Assays Using a Thermostable DNA Polymerase and Delayed Extraction MALDI-TOF Mass Spectrometry", Genome Research, vol. 7, pp. 378-388 (1997).
Hall, J. et al., "Sensitive detection of DNA polymorphisms by the serial invasive signal amplification reaction", PNAS, vol. 97(15), pp. 8272-8277 (2000).
Halushka, M. et al., "Patterns of single-nucleotide polymorphisms in candidate genes for blood-pressure homeostasis", Nature genetics, vol. 22, pp. 239-247 (1999).
Han, M. et al., "Quantum-dot-tagged microbeads for multiplexed optical coding of biomolecules", Nature biotechnology, vol. 19, pp. 631-635 (2001).
Hatch, A. et al., "Rolling circle amplification of DNA immobilized on solid surfaces and its application to multiplex mutation detection", Genetic Analysis: Biomolecular Engineering, vol. 15, pp. 35-40 (1999).
Head, S. et al., "Nested genetic bit analysis (N-GBA) for mutation detection in the p53 tumor suppressor gene", Nucleic Acids Research, vol. 25(24), pp. 5065-5071 (1997).
Hensel, M. et al., "Simultaneous Identification of Bacterial Virulence Genes by Negative Selection", Science, vol. 269, pp. 400-403 (1995).
Herschlag, D., "RNA Chaperones and the RNA Folding Problem", The Journal of Biological Chemistry, vol. 270(36), pp. 20871-20874 (1995).
Hirschhorn, J. et al., "SBE-TAGS: An array-based method for efficient single-nucleotide polymorphism genotyping", PNAS, vol. 97(22), pp. 12164-12169 (2000).
Holcomb, I. et al., "FIZZ1, a novel cysteine-rich secreted protein associated with pulmonary inflammation, defines a new gene family", The EMBO Journal, vol. 19(15), pp. 4046-4055 (2000).
Hsu, T. et al., "Genotyping Single-Nucleotide Polymorphisms by the Invader Assay with Dual-Color Fluorescence Polarization Detection", Clinical Chemistry, vol. 47(8), pp. 1373-1377 (2001).
Iannone, M. et al., "Multiplexed Single Nucleotide Polymorphism Genotyping by Oligonucleotide Ligation and Flow Cytometry", Cytometry, vol. 39, pp. 131-140 (2000).
Innis, M. et al., PCR Protocols: A Guide to Methods and Applications, Academic Press Inc, (1990).
Jackson, P. et al., "Mass spectrometry for genotyping: an emerging tool for molecular medicine", Molecular Medicine Today, vol. 6, pp. 271-276 (2000).
Jakoby, W., "Enzyme Purification and Related Techniques", Methods in Enzymology, vol. 104, Academic Press (1984).
Jemsek, J. et al., "Body Fat and Other Metabolic Effects of Atazanavir and Efavirenz, Each Administered in Combination with Zidovudine plus Lamivudine, in Antiretroviral-Naïve HIV-Infected Patients", HIV/AIDS, vol. 42, pp. 273-280 (2006).
Jiang-Baucom, P. et al., "DNA Typing of Human Leukocyte Antigen Sequence Polymorphisms by Peptide Nucleic Acid Probes and MALDI-TOF Mass Spectrometry", Anal. Chem., vol. 69, pp. 4894-4898 (1997).
Jurinke, C. et al., "Automated Genotyping using the DNA MassArray™ Technology", Methods in Molecular Biology, DNA Arrays Methods and Protocols, vol. 170, 103-116 (2001).
Kang, J. et al., "Zinc Finger Proteins as Designer Transcription Factors", The Journal of Biological Chemistry, vol. 275(12), p. 8742-8748 (2000).
Kaser, S. et al., "Resistin messenger-RNA expression is increased by proinflammatory cytokines in vitro", Biochemical and Biophysical Research Communications, vol. 309, pp. 286-290 (2003).
Kitatani, N. et al., "Association of serum resistin with TNF system activity in Japanese type 2 diabetic patients", Diabetes and Metabolism, vol. 33, pp. 156-157 (2007).

Knapp, M. et al., "The Haplotype-Relative-Risk (HRR) Method for analysis of Association in Nuclear Families", Am. J. Hum. Genet., vol. 52, pp. 1085-1093 (1993).
Kokoris, M. et al., "High-throughput SNP Genotyping with the Masscode Cystem", Molecular Diagnosis, vol. 5(4), pp. 329-340 (2000).
Kubota, T. et al., "Representational difference analysis using myeloid cells from C/EBPε deletional mice", Blood, vol. 96(12), pp. 3953-3957 (2000).
Kwoh, D. et al., "Transcription-based amplification system and detection of amplified human immunodeficiency virus type 1 with a bead-based sandwich hybridization format", PNAS, vol. 86, pp. 1173-1177 (1989).
Kwok, P., "High-throughput genotyping assay approaches", Pharmacogenomics, vol. 1(1), pp. 95-100 (2000).
Ladner, D. et al., "Multiplex detection of Hotspot Mutations by Rolling Circle-enabled Universal Microarrays", Laboratory Investigation, vol. 81(8), pp. 1079-1086 (2001).
Landegren, U. et al., "Reading Bits of Genetic Information: Methods for Single-Nucleotide Polymorphism Analysis", Genome Research, vol. 8, pp. 769-776 (1998).
Landegren, U. et al., "A Ligase-Mediated Gene Detection Technique", Science, vol. 241, pp. 1077-1080 (1988).
Latif, S. et al., "Fluorescence Polarization in Homogeneous Nucleic Acid Analysis II: 5'-Nuclease Assay", Genome Research, vol. 11, pp. 436-440 (2001).
Lehrke, M. et al., "An Inflammatory Cascade Leading to Hyper-resistinemia in Humans", PLoS Medicine, vol. 1(2), e45 pp. 161-168(Nov. 2004).
Leon, O. et al., "Zinc fingers: DNA binding and protein-protein interactions", Biol Res., vol. 33, pp. 21-30 (2000).
Li, J. et al., "Single nucleotide polymorphism determination using primer extension and time-of-flight mass spectrometry", Electrophoresis, vol. 20, pp. 1258-1265 (1999).
Li. T. et al., "Case-control, haplotype relative risk and transmission disequilibrium analysis of a dopamine D2 receptor functional promoter polymorphism in schizophrenia", Schizophrenia Research, vol. 32, pp. 87-92 (1998).
Lindblad-Toh, K. et al., "Large-scale discovery and genotyping of single-nucleotide polymorphisms in the mouse", Nature genetics, vol. 24, pp. 381-386 (2000).
Lindroos, K. et al., "Minisequencing on oligonucleotide microarrays: comparison of immobilization chemistries", Nucleic Acids Research, vol. 29(13), e69 (2001).
Link, A., "Multidimensional peptide separations in proteomics", Trends in Biotechnology, vol. 20(12) Supplement, pp. S8-S13 (2002).
Lipshutz, R. et al., "High density synthetic oligonucleotide arrays", Nature Genetics supplement, vol. 21, pp. 20-24 (1999).
Little, D. et al., "MALDI on a Chip: Analysis of Arrays of Low-Femtomole to Subfemtomole Quantities of Synthetic Oligonucleotides and DNA Diagnostic Products Dispensed by a Piezoelectric Pipet", Anal. Chem., vol. 69(22), pp. 4540-4546 (1997).
Little, D. et al., "Mass spectrometry from miniaturized arrays for full comparative DNA analysis", Nature Medicine, vol. 3(12), pp. 1413-1416 (1997).
Livak, K., "Allelic discrimination using fluorogenic probes and the 5' nuclease assay", Genetic Analysis: Biomolecular Engineering, vol. 14, pp. 143-149 (1999).
Lizardi, P. et al., "Mutation detection and single-molecule counting using isothermal rolling-circle amplification", Nature genetics, vol. 19, pp. 225-232 (1998).
Long, J. et al., "An E-M Algorithm and Testing Strategy for Multiple-Locus Haplotypes", Am. J. Hum. Genet., vol. 56, pp. 799-810 (1995).
Lyamichev, V. et al., "Polymorphism identification and quantitative detection of genomic DNA by invasive cleavage of oligonucleotide probes", Nature Biotechnology, vol. 17, pp. 292-296 (1999).
Ma, X. et al., "Genetic Variants at the Resistin Locus and Risk of Type 2 Diabetes in Caucasians", The J. of Clinical Endocrinology & Metabolism, vol. 87(9), pp. 4407-4410 (2002).

Manfredi, R. et al., "Disorders of Lipid Metabolism in Patients with HIV Disease Treated with Antiretroviral Agents: Frequency, Relations with Administered Drugs, and Role of Hypolipidaemic Therapy with Bezafibrate", Journal of Infection, vol. 42, pp. 181-188 (2001).
Marras, S. et al., "Multiplex detection of single-nucleotide variations using molecular beacons", Genetic Analysis: Biomolecular Engineering, vol. 14, pp. 151-156 (1999).
Matise, T. et al., "Genome Scanning for Complex Disease Genes using the Transmission/Disequilibrium Test and Haplotype-based Haplotype Relative Risk", Genetic Epidemiology, vol. 12, pp. 641-645 (1995).
Mattevi, V. et al., "A resistin gene polymorphism is associated with body mass index in women", Hum Genet., vol. 115, pp. 208-212 (2004).
Mattila, P. et al., "Fidelity of DNA synthesis by the *Thermococcus litoralis* DNA polymerase-an extremely heat stable enzyme with proofreading activity", Nucleic Acids Research, vol. 19(18), pp. 4967-4973 (1991).
McColl, D. et al., "Structure-based design of an RNA-binding zinc finger", PNAS, vol. 96, pp. 9521-9526 (1999).
McDonald, W. et al., "Shotgun proteomics and biomarker discovery", Disease Markers, vol. 18, pp. 99-105 (2002).
M^cTernan, P. et al., "Increased Resistin Gene and Protein Expression in Human Abdominal Adipose Tissue", The J. of Clinical Endocrinology & Metabolism, vol. 87(5), pp. 2407-2410 (2002).
Mein, C. et al., "Evaluation of Single Nucleotide Polymorphism Typing with Invader on PCR Amplicons and its Automation", Genome Research, vol. 10, pp. 330-343 (2000).
Michael, K. et al., "Randomly ordered Addressable High-Density Optical Sensor Arrays", Anal Chem., vol. 70, pp. 1242-1248 (1998).
Motojima, K., "The physiological role of resistin and its connection with metabolic diseases", J. Endocrinol. Invest., vol. 26, pp. 1171-1173 (2003).
Mullis, K. et al., "Specific enzymatic amplification of DNA In Vitro: The Polymerase Chain Reaction", Cold Spring Harbor Symposia on Quantitative Biology, vol. LI, pp. 263-273 (1986).
Muse, E. et al., "Hypothalamic resistin induces hepatic insulin resistance", The Journal of Clinical Investigation, vol. 117(6), pp. 1670-1678 (2007).
Myakishev, M. et al., "High-Throughput SNP Genotyping by Allele-Specific PCR with Universal Energy-Transfer-Labeled Primers", Genome Research, vol. 11, pp. 163-169 (2001).
Nielsen, P. et al., "Sequence-Selective Recognition of DNA by Strand Displacement with a Thymine-Substituted Polyamide", Science, vol. 254, pp. 1497-1500 (1991).
Nikiforov, T. et al., "Genetic Bit Analysis: a solid phase method for typing single nucleotide polymorphisms", Nucleic Acids Research, vol. 22(20), pp. 4167-4175 (1994).
Nilsson, M. et al., "Padlock Probes: Circularizing Oligonucleotides for Localized DNA Detection", Science, vol. 265, pp. 2085-2088 (1994).
Norata, G. et al., "Effect of the -420C/G variant of the resistin gene promoter on metabolic syndrome, obesity, myocardial infarction and kidney dysfunction", Journal of Internal Medicine, vol. 262, pp. 104-112 (2007).
Ochi, M. et al., "The absence of evidence for major effects of the frequent SNP+299G>A in the resistin gene on susceptibility to insulin resistance syndrome associated with Japanese type 2 diabetes", Diabetes Research and Clinical Practice, vol. 61, pp. 191-198 (2003).
Ohnishi, Y. et al., "A high-throughput SNP typing system for genome-wide association studies", J Hum Genet, vol. 46, pp. 471-477 (2001).
Ohtaka, H. et al., "Thermodynamic rules for the design of high affinity HIV-1 protease inhibitors with adaptability to mutations and high selectivity towards unwanted targets", The International Journal of Biochemistry & Cell Biology, vol. 36, pp. 1787-1799 (2004).
Orita, M. et al., "Detection of polymorphisms of human DNA by gel electrophoresis as single-strand conformation polymorphisms", PNAS, vol. 86, pp. 2766-2770 (1989).
Osawa, H. et al., "The G/G Genotype of a Resistin Single-Nucleotide Polymorphism at—420 Increases Type 2 Diabetes Mellitus Susceptibility by Inducing Promoter Activity through specific binding of Sp1/3", Am J Hum Genet, vol. 75, pp. 678-686 (2004).

Ott, J., "Statistical Properties of the Haplotype Relative Risk", Genetic Epidemiology, vol. 6, pp. 127-130 (1989).
Pang, J. et al., "Biomarker Discovery in Urine by Proteomics", Journal of Proteome Research, vol. 1, pp. 161-169 (2002).
Parker, R. et al., "Endoplasmic Reticulum Stress Links Dyslipidemia to Inhibition of Proteasome Activity and Glucose Transport by HIV Protease Inhibitors", Molecular Pharmacology, vol. 67(6), pp. 1909-1919 (2005).
Pastinen, T. et al., "A System for Specific, High-throughput Genotyping by Allele-specific Primer Extension on Microarrays", Genome Research, vol. 10, pp. 1031-1042 (2000).
Patel, S. et al., "Disulfide-Dependent Multimeric Assembly of Resistin Family Hormones", Science, vol. 304, pp. 1154-1158 (2004).
Pease, A. et al., "Light-generated oligonucleotide arrays for rapid DNA sequence analysis", PNAS, vol. 91, pp. 5022-5026 (1994).
Périard, D. et al., "Atherogenic Dyslipidemia in HIV-Infected Individuals Treated with Protease Inhibitors", Circulation, vol. 100, pp. 700-705 (1999).
Pizzuti, A. et al., "An ATG Repeat in the 3'-Untranslated Region of the Human Resistin Gene is Associated with a Decreased Risk of Insulin Resistance", The Journal of Clinical Endocrinology & Metabolism, vol. 87(9), pp. 4403-4406 (2002).
Pomerantz, J. et al., "Structure-Based Design of a Dimeric Zinc Finger Protein", Biochemistry, vol. 37(4), pp. 965-970 (1998).
Rajala, M. et al., "Adipose-derived resistin and gut-derived resistin-like molecular-β selectively impair insulin action on glucose production", The J. of Clinical Investigation, vol. 111(2), pp. 225-230 (2003).
Ranade, K. et al., "High-Throughput Genotyping with Single Nucleotide Polymorphisms", Genome Research, vol. 11, pp. 1262-1268 (2001).
Rojas, C. et al., "Indinavir did not further increase mean triglyceride levels in HIV-infected patients treated with nucleoside reverse transcriptase inhibitors: An analysis of three randomized clinical trials", Pharmacoepidemiology and Drug Safety, vol. 12, pp. 361-369 (2003).
Ronaghi, M., "Pyrosequencing Sheds Light on DNA Sequencing", Genome Research, vol. 11, pp. 3-11, (2001).
Ronaghi, M. et al., "A Sequencing Method Based on Real-Time Pyrophosphate", Science, vol. 281(5375), pp. 363-365 (1998).
Ross, P. et al., "Discrimination of Single-Nucleotide Polymorphisms in Human DNA Using Peptide Nucleic Acid Probes Detected by MALDI-TOF Mass Spectrometry", Anal Chem., vol. 69, pp. 4197-4202 (1997).
Ross, P. et al., "High level multiplex genotyping by MALDI-TOF mass spectrometry", Nature Biotechnology, vol. 16, pp. 1347-1351 (1998).
Saiki, R. et al., "Analysis of enzymatically amplified β-globin and HLA-DQα DNA with allele-specific oligonucleotide probes", Nature, vol. 324, pp. 163-166 (1986).
Saiki, R. et al., "Primer-Directed Enzymatic Amplification of DNA with a Thermostable DNA Polymerase", Science, vol. 239, pp. 487-491 (1988).
Sambrook, J. et al., Molecular Cloning, A Laboratory Manual, Second Edition, Cold Spring Harbor Laboratory Press (1989).
Sapolsky, R. et al., "High-throughput polymorphism screening and genotyping with high-density oligonucleotide arrays", Genetic Analysis: Biomolecular Engineering, vol. 14, pp. 187-192 (1999).
Sauer, S. et al., "Full flexibility genotyping of single nucleotide polymorphisms by the GOOD assay", Nucleic Acid Research, vol. 28(23) e100 (2000).
Sauer, S. et al., "A novel procedure for efficient genotyping of single nucleotide polymorphisms", Nucleic Acids Research, vol. 28(5), pp. e13 (2000).
Scopes, R., Protein Purification: Principles and Practice, Second Edition, Springer-Verlag (1987).
Segal, D. et al., "Toward controlling gene expression at will: Selection and design of zinc finger domains recognizing each of the 5'-GNN-3' DNA target sequences", PNAS, vol. 96, pp. 2758-2763 (1999).
Sentinelli, F. et al., "Human *Resistin* Gene, Obesity, and Type 2 Diabetes", Diabetes, vol. 51, pp. 860-862 (2002).

Seo, J. et al., "Functional Characterization of the Human Resistin Promoter with Adipocyte Determination- and Differentiation-Dependent Factor 1/Sterol Regulatory Element Binding Protein 1c and CCAAT Enhancer Binding Protein-α", Molecular Endocrinology, vol. 17(8), pp. 1522-1533 (2003).

Shoemaker, D. et al., "Quantitative phenotypic analysis of yeast deletion mutants using a highly parallel molecular bar-coding strategy", Nature genetics, vol. 14, pp. 450-456 (1996).

Shumaker, J. et al., "Mutation Detection by Solid Phase Primer Extension", Human Mutation, vol. 7, pp. 346-354 (1996).

Smith, S. et al., "A Promoter Genotype and Oxidative Stress Potentially Link Resistin to Human Insulin Resistance", Diabetes, vol. 52, pp. 1611-1618 (2003).

Southern, E. et al., "Analyzing and Comparing Nucleic Acid Sequences by Hybridization to Arrays of Oligonucleotides: Evaluation Using Experimental Models", Genomics, vol. 13, pp. 1008-1017 (1992).

Steemers, F. et al., "Screening unlabeled DNA targets with randomly ordered fiber-optic gene arrays", Nature Biotechnology, vol. 18, pp. 91-94 (2000).

Steppan, C. et al., "A family of tissue-specific resistin-like molecules", PNAS, vol. 98(2), pp. 502-506 (2001).

Steppan, C. et al., "The hormone resistin links obesity to diabetes", Nature, vol. 409, pp. 307-312 (2001).

Sun, X. et al., "A new MALDI-TOF based mini-sequencing assay for genotyping of SNPS", Nucleic Acids Research, vol. 28(12), e68, (2000).

Syvänen, A. et al., "Convenient and Quantitative Determination of the Frequency of a Mutant Allele Using Solid-Phase Minisequencing: Application to Aspartylglucosaminuria in Finland", Genomics, vol. 12, pp. 590-595 (1992).

Takeishi, Y. et al., "Serum Resistin is Associated with High Risk in Patients with Congestive Heart Failure—A Novel Link Between Metabolic Signals and Heart Failure—", Circulation Journal, vol. 71, pp. 460-464 (2007).

Tan, M. et al., "Association of Resistin Gene 3'-Untranslated Region +62G→A Polymorphism with Type 2 Diabetes and Hypertension in a Chinese Population", The J. of Clinical Endocrinology & Metabolism, vol. 88(3), pp. 1258-1263 (2003).

Tang, K. et al., "Chip-based genotyping by mass spectrometry", PNAS, vol. 96, pp. 10016-10020 (1999).

Taranenko, N. et al., "Laser desorption mass spectrometry for point mutation detection", Genetic Analysis: Biomolecular Engineering, vol. 13, pp. 87-94 (1996).

Templeton, A. et al., "Recombinational and Mutational Hotspots within the Human Lipoprotein Lipase Gene", Am J Hum Genet, vol. 66, pp. 69-83 (2000).

Terwilliger, J. et al., "A Haplotype-Based 'Haplotype Relating Risk' approach to Detecting Allelic Association", Hum Hered., vol. 42, pp. 337-346 (1992).

Tillib, S. et al., "Advances in the analysis of DNA sequence variations using oligonucleotide microchip technology", Current Opinion in Biotechnology, vol. 12, pp. 53-58 (2001).

Tokuyama, Y. et al., "Serum resistin level is associated with insulin sensitivity in Japanese patients with type 2 diabetes mellitus", Metabolism Clinical and Experimental, vol. 56, pp. 693-698 (2007).

Torti, C. et al., "Lipid Abnormalities in HIV-Infected Patients are not Correlated with Lopinavir Plasma Concentrations", Acquir Immune Defic Syndr, vol. 35(3), pp. 324-328 (2004).

Tsuchihashi, Z. et al., "DNA Strand Exchange and Selective DNA Annealing Promoted by the Human Immunodeficiency Virus Type 1 Nucleocapsid Protein", Journal of Virology, vol. 68(9), pp. 5863-5870 (1994).

Wang, D. et al., "Large-Scale Identification, Mapping, and Genotyping of Single-Nucleotide Polymorphisms in the Human Genome", Science, vol. 280, pp. 1077-1082 (1998).

Wang, H. et al., "Human Resistin Gene: Molecular Scanning and Evaluation of Association with Insulin Sensitivity and Type 2 Diabetes in Caucasians", The J. of Clinical Endocrinology & Metabolism, vol. 87(6), pp. 2520-2524 (2002).

Wang, B. et al., "Dimerization of zinc fingers mediated by peptides evolved in vitro from random sequences", PNAS, vol. 96, pp. 9568-9573 (1999).

Whitcombe, D. et al., "Advances in approaches to DNA-based diagnostics", Current Opinion in Biotechnology, vol. 9, pp. 602-608 (1998).

Winzeler, E. et al., "Direct Allelic Variation Scanning of the Yeast Genome", Science, vol. 281, pp. 1194-1197 (1998).

Wolfe, S. et al., "Combining structure-based design with phage display to create new $Cys_2His_2$ zinc finger dimers", Structure, vol. 8, pp. 739-750 (2000).

Wolfe, S. et al., "Analysis of Zinc Fingers Optimized via Phage Display: Evaluating the Utility of a Recognition Code", J. Mol Biology, vol. 285, pp. 1917-1934 (1999).

Wu, K. et al., The Ligation Amplification Reaction (LAR)—Amplification of Specific DNA Sequences Using Sequential Rounds of Template-dependent Ligation, Genomics, vol. 4, pp. 560-569 (1989).

Yagmur, E. et al., "Resistin Serum Levels are Associated with Insulin Resistance, Disease Severity, Clinical Complications, and Prognosis in Patients with Chronic Liver Diseases", American Journal of Gastroenterology, vol. 101, pp. 1244-1252 (2006).

Ye, F. et al., "Fluorescent Microsphere-Based Readout Technology for Multiplexed Human Single Nucleotide Polymorphism Analysis and Bacterial Identification", Human Mutation, vol. 17, pp. 305-316 (2001).

Zhong, X. et al., "Visualization of oligonucleotide probes and point mutations in interphase nuclei and DNA fibers using rolling circle DNA amplification", PNAS, vol. 98(7), pp. 3940-3945 (2001).

NCBI Entrez Accession No. AC008963 gi:9256098, Jul. 18, 2000 DOE Joint Genome Institute.

NCBI Entrez Accession No. NM_020415 gi:13435379 Sep. 25, 2007 Norata, et al.

NCBI Entrez Accession No. NP_065148 gi:9966777 Sep. 25, 2007 Norata, et al.

FIG. 3A

```
   1 ATAAAAATGTAATAACCATTCCAAGCTCATGGGTGGTCCAAGAAGAAACATGAGCTGGAC   60

61 CTTGGCCCATGAGCAATGGCTTTCCAACTTCTGTTGCAGGTGATGCCATTGATGGAATAA  120

121 ACCATGATTTTTCTTTCTTCTTTTTGAGATGGAGTCTTGCTATGGTGCCCAAGCTAGTCA  180

181 TCCAGGATGGAGTGCAGGGGCACGATCTCAGTGCACTGCAACCTCCACATCCCGGGTTCA  240

241 AGTGATTCTCCCACCTCAGCCTCCCAAGTAGCTGGGATTACAGGCACACGCCACCACGCC  300

301 CAGTTAATTTTTGTATGTCTAATGGAGACAGGGTTTCATCATGTTGGCCAGGTTGGTCTC  360

361 AAGCTCCTGACCTCAAGTGATCCGCCCGCCTTGGCCTCCCAAAGTGCTGGGATTACAGGC  420

421 GTGAGCCACCGGCCATAAACCATGATTTTATTTACCAGTTCTATTGCTCATGGGCATTTG  480

481 GGTATGAATGTGGTATGTCATTCTCACCCAGAGACATAATTATTATTACTATTTTAGAGA  540

541 AGTGGTCTTGCTCTGTTGCCCAGACTGGAGTGCAGTGCTGTGATCATAAGTCACTGTAGC  600

601 TTCGAACTCCCGGGCTCAAGCAATTCTCTCACGTCAGCCTCCTTAGTAGCTGGGACTACA  660

661 AGTGCTTGTCCGCACCATGCCTAGCAAGAGGCATTAATTTTGTCATGTTTGCATCAGCCA  720

721 CCCTTGCATGCAAAACTCTGCTTGTCTACCTGTTCCTCAGACCACAGCCCCTGGCATTAT  780

781 CCCTGGGGCACCACCTCCTGACCAGTCTCTGGACATGAAGACGGAGGCCCTGTTGGAAGT  840

841 GGGAAGGCTCCCTTCCTCCTCCAGCCCTTACTGTCTGCTCAGGGGCTTCCTCTTGGCCCC  900

901 GGATGTGGGACCGGAGGGTTGGGGGCCCAGGGACTTATTAGCCAAGCCAGGAAGCCCCAC  960

961 CCCAAGAGGCCTCAAAGAAAGAGCTGCGGTGCAGGAATTCGTGTGCCGGATTTGGTTAGC 1020

1021 TGAGCCCACCGAGAGGGTAAGTGACAGCTGCTCCTGCGCTTGCCATGGCACCAGCGGGGA 1080

1081 GGCTGGGGTCAAGGCTGAGCCTCCATCCCTGTCCCCACATGGGGGGACAGGGGTCCAGG 1140

1141 TCCAGGGGCAGATCCTACTCCCTCCATGGGCCGGATCTTCCCCACAGGGCAGGGCTGATC 1200
```

FIG. 3B

```
1201 CAGCTGTGGGTCTCTTGGTTCCCTCTTTCAGCGCCTGCAGGATGAAAGCTCTCTGTCTCC 1260

1261 TCCTCCTCCCTGTCCTGGGGCTGTTGGTGTCTAGCAAGACCCTGTGCTCCATGGAAGAAG 1320

1321 CCATCAATGAGAGGATCCAGGAGGTCGCCGGCTCCCTAAGTGAGGACCCCCCACTTGGGC 1380

1381 AAGCTCCCCAAGGGTCTCAGAGACCTCACTGATCCCTGGCACAGACCTGACTCCAACCCA 1440

1441 GCCCCAGCGCTCACCAAATCTCATCCTCAAATCCAACCAGATCATAAATTCAACCCCAAC 1500

1501 TCCACTCCCAACCCCTCCGACTGTCCCCACCTTATCCACGGCTCCAAACCCAATCCCCGC 1560

1561 TCTCACTCCAAACCTTCCCTTACTCCAAAACACCCAACTCAAGACAGGGTCCTGGAGGCC 1620

1621 AGTGAGCTCCTATGCCCACAGGGACCTAGCTCCAAACCAACAGGGCTAGGGGAGGATGGG 1680

1681 GGAGGGACCGTTTGGTCTCACAGCTCCCCCTGTCTCCTTTCCTCCTGCCCCCCAGTATTT 1740

1741 AGGGCAATAAGCAGCATTGGCCTGGAGTGCCAGAGCGTCACCTCCAGGGGGACCTGGCT 1800

1801 ACTTGCCCCCGAGGTGAGTGCAGGAGACTGTTGTCCAGGCGCCCATTTCTGTTCCAAGTC 1860

1861 CCCTGGGAATGCCCCCTCCCCGCCACGTTCCCCGTGTCCAGCCTCTACTCCCCTAGGATC 1920

1921 TTGGTCCTGACTCCCAGCCTTCTCCGCCCACCATCTGGACACTGGTGTCCACCCTCACTC 1980

1981 CCTGCCTCCAGTGCCCATTCAGTGGTTGGAGCCTCCAGCCGTCCCCGTCCCCACCCCCGC 2040

2041 CCCCCAACCCCCCTCCGCGCTCCCCACCCCCCTCCCGCTCCCACCCTCAGCCTCCCAGC 2100

2101 TCAGAGTCCACGCTCCTGTGTTCCGGGCTGCAGGCTTCGCCGTCACCGGCTGCACTTGTG 2160

2161 GCTCCGCCTGTGGCTCGTGGGATGTGCGCGCCGAGACCACATGTCACTGCCAGTGCGCGG 2220

2221 GCATGGACTGGACCGGAGCGCGCTGCTGTCGTGTGCAGCCCTGAGGTCGCGCGCAGCGCG 2280

2281 TGCACAGCGCGGGCGGAGGCGGCTCCAGGTCCGGAGGGGTTGCGGGGGAGCTGGAAATAA 2340

2341 ACCTGGAGATGATGATGATGATGATGATG 2369
```

FIG. 4A

```
   1 ATAAAAATGTAATAACCATTCCAAGCTCATGGGTGGTCCAAGAAGAAACATGAGCTGGAC   60

61 CTTGGCCCATGAGCAATGGCTTTCCAACTTCTGTTGCAGGTGATGCCATTGATGGAATAA  120

121 ACCATGATTTTTCTTTCTTCTTTTTGAGATGGAGTCTTGCTATGGTGCCCAAGCTAGTCA  180

181 TCCAGGATGGAGTGCAGGGGCACGATCTCAGTGCACTGCAACCTCCACATCCCGGGTTCA  240

241 AGTGATTCTCCCACCTCAGCCTCCCAAGTAGCTGGGATTACAGGCACACGCCACCACGCC  300

301 CAGTTAATTTTTGTATGTCTAATGGAGACAGGGTTTCATCATGTTGGCCAGGTTGGTCTC  360

361 AAGCTCCTGACCTCAAGTGATCCGCCCGCCTTGGCCTCCCAAAGTGCTGGGATTACAGGC  420

421 GTGAGCCACCGGCCATAAACCATGATTTTATTTACCAGTTCTATTGCTCATGGGCATTTG  480

481 GGTATGAATGTGGTATGTCATTCTCACCCAGAGACATAATTATTATTACTATTTTAGAGA  540

541 AGTGGTCTTGCTCTGTTGCCCAGACTGGAGTGCAGTGCTGTGATCATAAGTCACTGTAGC  600

601 TTCGAACTCCCGGGCTCAAGCAATTCTCTCACGTCAGCCTCCTTAGTAGCTGGGACTACA  660

661 AGTGCTTGTCCGCACCATGCCTAGCAAGAGGCATTAATTTTGTCATGTTTGCATCAGCCA  720

721 CCCTTGCATGCAAAACTCTGCTTGTCTACCTGTTCCTCAGACCACAGCCCCTGGCATTAT  780

781 CCCTGGGGCACCACCTCCTGACCAGTCTCTGGACATGAAGACGGAGGCCCTGTTGGAAGT  840

841 GGGAAGGCTCCCTTCCTCCTCCAGCCCTTACTGTCTGCTCAGGGGCTTCCTCTTGGCCCC  900

901 GGATGTGGGACCGGAGGGTTGGGGGCCCAGGGACTTATTAGCCAAGCCAGGAAGCCCCAC  960

961 CCCAAGAGGCCTCAAAGAAAGAGCTGCGGTGCAGGAATTCGTGTGCCGGATTTGGTTAGC 1020

1021 TGAGCCCACCGAGAGGGTAAGTGACAGCTGCTCCTGCGCTTGCCATGGCACCAGCGGGGA 1080

1081 GGCTGGGGTCAAGGCTGAGCCTCCATCCCTGTCCCCACATGGGGGGACAGGGGTCCAGG 1140

1141 TCCAGGGGCAGATCCTACTCCCTCCATGGGCCGGATCTTCCCCACAGGGCAGGGCTGATC 1200
```

FIG. 4B

```
1201 CAGCTGTGGGTCTCTTGGTTCCCTCTTTCAGCGCCTGCAGGATGAAAGCTCTCTGTCTCC 1260

1261 TCCTCCTCCCTGTCCTGGGGCTGTTGGTGTCTAGCAAGACCCTGTGCTCCATGGAAGAAG 1320

1321 CCATCAATGAGAGGATCCAGGAGGTCGCCGGCTCCCTAAGTGAGGACCCCCCACTTGGGC 1380

1381 AAGCTCCCCAAGGGTCTTAGAGACCTCACTGATCCCTGGCACAGACCTGACTCCAACCCA 1440

1441 GCCCCAGCGCTCACCAAATCTCATCCTCAAATCCAACCAGATCATAAATTCAACCCCAAC 1500

1501 TCCACTCCCAACCCCTCCGACTGTCCCCACCTTATCCACGGCTCCAAACCCAATCCCCGC 1560

1561 TCTCACTCCAAACCTTCCCTTACTCCAAAACACCCAACTCAAGACAGGGTCCTGGAGGCC 1620

1621 AGTGAGCTCCTATGCCCACAGGGACCTAGCTCCAAACCAACAGGGCTAGGGGAGGATGGG 1680

1681 GGAGGGACCGTTTGGTCTCACAGCTCCCCCTGTCTCCTTTCCTCCTGCCCCCCAGTATTT 1740

1741 AGGGCAATAAGCAGCATTGGCCTGGAGTGCCAGAGCGTCACCTCCAGGGGGGACCTGGCT 1800

1801 ACTTGCCCCCGAGGTGAGTGCAGGAGACTGTTGTCCAGGCGCCCATTTCTGTTCCAAGTC 1860

1861 CCCTGGGAATGCCCCCTCCCCGCCACGTTCCCCGTGTCCAGCCTCTACTCCCCTAGGATC 1920

1921 TTGGTCCTGACTCCCAGCCTTCTCCGCCCACCATCTGGACACTGGTGTCCACCCTCACTC 1980

1981 CCTGCCTCCAGTGCCCATTCAGTGGTTGGAGCCTCCAGCCGTCCCCGTCCCCACCCCCGC 2040

2041 CCCCCCAACCCCCCTCCGCGCTCCCCACCCCCCTCCCGCTCCCACCCTCAGCCTCCCAGC 2100

2101 TCAGAGTCCACGCTCCTGTGTTCCGGGCTGCAGGCTTCGCCGTCACCGGCTGCACTTGTG 2160

2161 GCTCCGCCTGTGGCTCGTGGGATGTGCGCGCCGAGACCACATGTCACTGCCAGTGCGCGG 2220

2221 GCATGGACTGGACCGGAGCGCGCTGCTGTCGTGTGCAGCCCTGAGGTCGCGCGCAGCGCG 2280

2281 TGCACAGCGCGGGCGGAGGCGGCTCCAGGTCCGGAGGGGTTGCGGGGGAGCTGGAAATAA 2340

2341 ACCTGGAGATGATGATGATGATGATGATG 2369
```

FIG. 5

Association Between Resistin SNP1 and
Incidence of HIV-1 Protease Inhibitor-Dependent Metabolic Abnormalities

| Genotype | Fold Incidence In High Risk Cluster Relative to Homozygous Wild-type (C/C) | Confidence Interval | P-Value |
|---|---|---|---|
| C/T | 2.7 | 95% C.I. 1.3-5.3 | P = 0.001 |
| T/T | 19 | 95% C.I. 2-183 | P = 0.001 |

SEQUENCE LISTING

<160> NUMBER OF SEQ ID NOS: 12

<210> SEQ ID NO 1
<211> LENGTH: 2369
<212> TYPE: DNA
<213> ORGANISM: homo sapiens

<400> SEQUENCE: 1

| | | | | | |
|---|---|---|---|---|---|
| ataaaaatgt | aataaccatt | ccaagctcat | gggtggtcca | agaagaaaca | tgagctggac | 60 |
| cttggcccat | gagcaatggc | tttccaactt | ctgttgcagg | tgatgccatt | gatggaataa | 120 |
| accatgattt | ttctttcttc | tttttgagat | ggagtcttgc | tatggtgccc | aagctagtca | 180 |
| tccaggatgg | agtgcagggg | cacgatctca | gtgcactgca | acctccacat | cccgggttca | 240 |
| agtgattctc | ccacctcagc | ctcccaagta | gctgggatta | caggcacacg | ccaccacgcc | 300 |
| cagttaattt | ttgtatgtct | aatggagaca | gggtttcatc | atgttggcca | ggttggtctc | 360 |
| aagctcctga | cctcaagtga | tccgcccgcc | ttggcctccc | aaagtgctgg | gattacaggc | 420 |
| gtgagccacc | ggccataaac | catgatttta | tttaccagtt | ctattgctca | tgggcatttg | 480 |
| ggtatgaatg | tggtatgtca | ttctcaccca | gagacataat | tattattact | attttagaga | 540 |
| agtggtcttg | ctctgttgcc | cagactggag | tgcagtgctg | tgatcataag | tcactgtagc | 600 |
| ttcgaactcc | cgggctcaag | caattctctc | acgtcagcct | ccttagtagc | tgggactaca | 660 |
| agtgcttgtc | cgcaccatgc | ctagcaagag | gcattaattt | tgtcatgttt | gcatcagcca | 720 |
| cccttgcatg | caaaactctg | cttgtctacc | tgttcctcag | accacagccc | ctggcattat | 780 |
| ccctggggca | ccacctcctg | accagtctct | ggacatgaag | acggaggccc | tgttggaagt | 840 |
| gggaaggctc | ccttcctcct | ccagcccctta | ctgtctgctc | aggggcttcc | tcttggcccc | 900 |
| ggatgtggga | ccggagggtt | gggggcccag | ggacttatta | gccaagccag | gaagccccac | 960 |
| cccaagaggc | ctcaaagaaa | gagctgcggt | gcaggaattc | gtgtgccgga | tttggttagc | 1020 |
| tgagcccacc | gagagggtaa | gtgacagctg | ctcctgcgct | tgccatggca | ccagcgggga | 1080 |
| ggctggggtc | aaggctgagc | ctccatccct | gtcccccaca | tgggggggaca | ggggtccagg | 1140 |
| tccaggggca | gatcctactc | cctccatggg | ccggatcttc | cccacagggc | agggctgatc | 1200 |
| cagctgtggg | tctcttggtt | ccctctttca | gcgcctgcag | gatgaaagct | ctctgtctcc | 1260 |
| tcctcctccc | tgtcctgggg | ctgttggtgt | ctagcaagac | cctgtgctcc | atggaagaag | 1320 |
| ccatcaatga | gaggatccag | gaggtcgccg | gctccctaag | tgaggacccc | ccacttgggc | 1380 |
| aagctcccca | agggtctcag | agacctcact | gatccctggc | acagacctga | ctccaaccca | 1440 |
| gccccagcgc | tcaccaaatc | tcatcctcaa | atccaaccag | atcataaatt | caaccccaac | 1500 |
| tccactccca | accccteega | ctgtccccac | cttatccacg | gctccaaacc | caatcccgc | 1560 |
| tctcactcca | aaccttccct | tactccaaaa | cacccaactc | aagacagggt | cctggaggcc | 1620 |
| agtgagctcc | tatgcccaca | gggacctagc | tccaaaccaa | cagggctagg | ggaggatggg | 1680 |
| ggagggaccg | tttggtctca | cagctccccc | tgtctccttt | cctcctgccc | ccagtatttt | 1740 |
| agggcaataa | gcagcattgg | cctggagtgc | cagagcgtca | cctccagggg | ggacctggct | 1800 |
| acttgccccc | gaggtgagtg | caggagactg | ttgtccaggc | gcccatttct | gttccaagtc | 1860 |
| ccctgggaat | gccccctccc | cgccacgttc | cccgtgtcca | gcctctactc | ccctaggatc | 1920 |
| ttggtcctga | ctcccagcct | tctccgccca | ccatctggac | actggtgtcc | accctcactc | 1980 |
| cctgcctcca | gtgcccattc | agtggttgga | gcctccagcc | gtccccgtcc | ccacccccgc | 2040 |

```
cccccaacc cccctccgcg ctccccaccc ccctcccgct cccaccctca gcctcccagc    2100
tcagagtcca cgctcctgtg ttccgggctg caggcttcgc cgtcaccggc tgcacttgtg    2160
gctccgcctg tggctcgtgg gatgtgcgcg ccgagaccac atgtcactgc cagtgcgcgg    2220
gcatggactg gaccggagcg cgctgctgtc gtgtgcagcc ctgaggtcgc gcgcagcgcg    2280
tgcacagcgc gggcggaggc ggctccaggt ccggaggggt tgcggggggag ctggaaataa    2340 acctggagat gatgatgatg atgatgatg                                      2369
```

<210> SEQ ID NO 2
<211> LENGTH: 2369
<212> TYPE: DNA
<213> ORGANISM: homo sapiens

<400> SEQUENCE: 2

```
ataaaaatgt aataaccatt ccaagctcat gggtggtcca agaagaaaca tgagctggac      60
cttggcccat gagcaatggc tttccaactt ctgttgcagg tgatgccatt gatggaataa     120
accatgattt ttcttttcttc tttttgagat ggagtcttgc tatggtgccc aagctagtca    180
tccaggatgg agtgcagggg cacgatctca gtgcactgca acctccacat cccgggttca    240
agtgattctc ccacctcagc ctcccaagta gctgggatta caggcacacg ccaccacgcc    300
cagttaattt ttgtatgtct aatggagaca gggtttcatc atgttggcca ggttggtctc    360
aagctcctga cctcaagtga tccgcccgcc ttggcctccc aaagtgctgg gattacaggc    420
gtgagccacc ggccataaac catgatttta tttaccagtt ctattgctca tgggcatttg    480
ggtatgaatg tggtatgtca ttctcaccca gagacataat tattattact atttagaga    540 agtggtcttg ctctgttgcc cagactggag tgcagtgctg tgatcataag tcactgtagc    600
ttcgaactcc cgggctcaag caattctctc acgtcagcct ccttagtagc tgggactaca    660
agtgcttgtc cgcaccatgc ctagcaagag gcattaattt tgtcatgttt gcatcagcca    720
cccttgcatg caaaactctg cttgtctacc tgttcctcag accacagccc ctggcattat    780
ccctggggca ccacctcctg accagtctct ggacatgaag acggaggccc tgttggaagt    840
gggaaggctc ccttcctcct ccagccctta ctgtctgctc aggggcttcc tcttggcccc    900
ggatgtggga ccggagggtt gggggcccag ggacttatta gccaagccag gaagccccac    960
cccaagaggc ctcaaagaaa gagctgcggt gcaggaattc gtgtgccgga tttggttagc    1020
tgagcccacc gagagggtaa gtgacagctg ctcctgcgct tgccatggca ccagcgggga    1080
ggctggggtc aaggctgagc ctccatccct gtcccccaca tggggggaca ggggtccagg    1140
tccaggggca gatcctactc cctccatggg ccggatcttc cccacagggc agggctgatc    1200
cagctgtggg tctcttggtt ccctcttttca gcgcctgcag gatgaaagct ctctgtctcc    1260
tcctcctccc tgtcctgggg ctgttggtgt ctagcaagac cctgtgctcc atggaagaag    1320
ccatcaatga gaggatccag gaggtcgccg gctccctaag tgaggacccc ccacttgggc    1380
aagctcccca agggtcttag agacctcact gatccctggc acagacctga ctccaaccca    1440
gccccagcgc tcaccaaatc tcatcctcaa atccaaccag atcataaatt caaccccaac    1500
tccactccca acccctccga ctgtcccccac cttatccacg gctccaaacc caatccccgc    1560
tctcactcca aaccttccct tactccaaaa cacccaactc aagacagggt cctggaggcc    1620
agtgagctcc tatgcccaca gggacctagc tccaaaccaa cagggctagg ggaggatggg    1680
ggagggaccg tttggtctca cagctccccc tgtctccttt cctcctgccc cccagtattt    1740
```

-continued

```
agggcaataa gcagcattgg cctggagtgc cagagcgtca cctccagggg ggacctggct    1800
acttgccccc gaggtgagtg caggagactg ttgtccaggc gcccatttct gttccaagtc    1860
ccctgggaat gccccctccc cgccacgttc cccgtgtcca gcctctactc ccctaggatc    1920
ttggtcctga ctcccagcct tctccgccca ccatctggac actggtgtcc accctcactc    1980
cctgcctcca gtgcccattc agtggttgga gcctccagcc gtcccgtcc ccaccccgc      2040 cccccaacc cccctccgcg ctccccaccc ccctcccgct cccaccctca gcctcccagc     2100
tcagagtcca cgctcctgtg ttccgggctg caggcttcgc cgtcaccggc tgcacttgtg    2160
gctccgcctg tggctcgtgg gatgtgcgcg ccgagaccac atgtcactgc cagtgcgcgg    2220
gcatggactg gaccggagcg cgctgctgtc gtgtgcagcc ctgaggtcgc gcgcagcgcg    2280
tgcacagcgc gggcggaggc ggctccaggt ccggaggggt tgcggggag ctggaaataa     2340 acctggagat gatgatgatg atgatgatg                                      2369
```

<210> SEQ ID NO 3
<211> LENGTH: 20
<212> TYPE: DNA
<213> ORGANISM: Homo sapiens

<400> SEQUENCE: 3
ccggctccct aagtgaggac                                                20

<210> SEQ ID NO 4
<211> LENGTH: 20
<212> TYPE: DNA
<213> ORGANISM: Homo sapiens

<400> SEQUENCE: 4
gagtcaggtc tgtgccaggg                                                20

<210> SEQ ID NO 5
<211> LENGTH: 25
<212> TYPE: DNA
<213> ORGANISM: Homo sapiens

<400> SEQUENCE: 5
tccccaaggg tctcagagac ctcac                                          25

<210> SEQ ID NO 6
<211> LENGTH: 27
<212> TYPE: DNA
<213> ORGANISM: Homo sapiens

<400> SEQUENCE: 6
tccccaaggg tcttagagac ctcactg                                        27

<210> SEQ ID NO 7
<211> LENGTH: 479
<212> TYPE: DNA
<213> ORGANISM: homo sapiens

<400> SEQUENCE: 7

```
gtgtgccgga tttggttagc tgagcccacc gagaggcgcc tgcaggatga aagctctctg    60
tctcctcctc ctccctgtcc tggggctgtt ggtgtctagc aagaccctgt gctccatgga    120
agaagccatc aatgagagga tccaggaggt cgccggctcc ctaatattta gggcaataag    180
cagcattggc ctggagtgcc agagcgtcac ctccaggggg gacctggcta cttgccccg     240 aggcttcgcc gtcaccggct gcacttgtgg ctccgcctgt ggctcgtggg atgtgcgcgc    300
```

```
cgagaccaca tgtcactgcc agtgcgcggg catggactgg accggagcgc gctgctgtcg    360
tgtgcagccc tgaggtcgcg cgcagcgcgt gcacagcgcg ggcggaggcg gctccaggtc    420
cggaggggtt gcgggggagc tggaaataaa cctggagatg atgatgatga tgatgatgg     479
```

<210> SEQ ID NO 8
<211> LENGTH: 24
<212> TYPE: DNA
<213> ORGANISM: Bacteriophage M13

<400> SEQUENCE: 8

```
cgccagggtt ttcccagtca cgac                                            24
```

<210> SEQ ID NO 9
<211> LENGTH: 24
<212> TYPE: DNA
<213> ORGANISM: Bacteriophage M13

<400> SEQUENCE: 9

```
agcggataac aatttcacac agga                                            24
```

<210> SEQ ID NO 10
<211> LENGTH: 39
<212> TYPE: DNA
<213> ORGANISM: Homo sapiens
<400> SEQUENCE: 10

```
ggcaagctcc ccaagggtct tagagacctc actgatccc                            39
```

<210> SEQ ID NO 11
<211> LENGTH: 39
<212> TYPE: DNA
<213> ORGANISM: Homo sapiens
<400> SEQUENCE: 11

```
gggatcagtg aggtctctaa gacccttggg gagcttgcc                            39
```

<210> SEQ ID NO 12
<211> LENGTH: 108
<212> TYPE: PRT
<213> ORGANISM: homo sapiens
<400> SEQUENCE: 12

```
Met Lys Ala Leu Cys Leu Leu Leu Pro Val Leu Gly Leu Leu Val
1               5                   10                  15

Ser Ser Lys Thr Leu Cys Ser Met Glu Glu Ala Ile Asn Glu Arg Ile
            20                  25                  30

Gln Glu Val Ala Gly Ser Leu Ile Phe Arg Ala Ile Ser Ser Ile Gly
        35                  40                  45

Leu Glu Cys Gln Ser Val Thr Ser Arg Gly Asp Leu Ala Thr Cys Pro
    50                  55                  60

Arg Gly Phe Ala Val Thr Gly Cys Thr Cys Gly Ser Ala Cys Gly Ser
65                  70                  75                  80

Trp Asp Val Arg Ala Glu Thr Thr Cys His Cys Gln Cys Ala Gly Met
                85                  90                  95

Asp Trp Thr Gly Ala Arg Cys Cys Arg Val Gln Pro
            100                 105
```

METHOD FOR IDENTIFYING HIV-1 PROTEASE INHIBITORS WITH REDUCED METABOLIC AFFECTS

This application is a divisional application of non-provisional application U.S. Ser. No. 11/823,707, filed Jun. 27, 2007, which claims benefit to provisional application U.S. Ser. No. 60/817,846 filed Jun. 30, 2006, under 35 U.S.C. 119(e). The entire teachings of the referenced application are incorporated herein by reference.

FIELD OF THE INVENTION

The invention provides a novel in vitro method for identifying HIV-1 protease inhibitors with reduced potential for inducing metabolic abnormalities. The invention further provides diagnostic methods for identifying patients who may be at risk of developing metabolic abnormalities subsequent to the administration of an HIV-1 protease inhibitor. The invention also provides novel polynucleotides associated with the incidence of HIV-1 protease inhibitor induced metabolic abnormalities. The invention also provides polynucleotide fragments corresponding to the genomic and/or coding regions of these polynucleotides which comprise at least one polymorphic locus per fragment. Allele-specific primers and probes which hybridize to these regions, and/or which comprise at least one polymorphic locus are also provided. The polynucleotides, primers, and probes of the present invention are useful in phenotype correlations, medicine, and genetic analysis. The invention further relates to diagnostic methods for using these novel polynucleotides in the diagnosis, treatment, and/or prevention of HIV-1 protease inhibitor induced metabolic abnormalities.

BACKGROUND OF THE INVENTION

Highly active antiretroviral therapy (HAART) involves the use of a combination of three different classes of antiviral compounds for the treatment of HIV infection. These compounds include the nucleoside reverse transcriptase inhibitors, non-nucleoside reverse transcriptase inhibitors and protease inhibitors.

HAART has improved the outcomes in HIV-1 infected patients, however, its use is complicated by metabolic adverse events that are collectively termed HAART-associated lipodystrophy Carr, A., Aids, 17 Suppl 1: p. S141-8 (2003). These metabolic changes include fat atrophy/hypertrophy, dyslipidemia and insulin resistance. Although the mechanistic basis underlying lipodystrophy associated with HAART is poorly understood, the associated metabolic abnormalities are well established cardiovascular risk factors (Grinspoon, S. et al., N Engl J Med, 352(1):48-62 (2005)).

Genetic association studies performed by the inventors revealed that a single nucleotide polymorphism in the resistin gene provided evidence of an association with a risk of developing lipodystrophy in patients enrolled on HAART. Resistin was originally cloned as an adipocytokine that provides a mechanistic link between obesity and insulin resistance (Steppan, C. M., et al., Nature, 409(6818):307-12 (2001)). In mice, hyperresistinemia results in insulin resistance (Rajala, M. W., et al., J Clin Invest, 111(2):225-30 (2003)) and knockout studies have shown that resistin deficient mice are protected from insulin resistance (Banerjee, R. R., et al., Science, 303(5661):1195-8 (2004)). In humans, resistin has been shown to be associated with components of lipodystrophy syndrome in some (Conneely, K. N., et al., Diabetologia, 47(10): 1782-8 (2004), Mattevi, V. S., et al., Hum Genet, 115(3):208-12 (2004)), but not all studies (Ochi, M., et al., Diabetes Res Clin Pract, 61(3): p. 191-8 (2003)).

Aspartyl proteases comprise a group of proteolytic enzymes that share the same catalytic mechanism (Dash, C., et al., Crit. Rev Biochem Mol Biol, 38(2):89-119 (2003)). Members of this family include HIV-1 protease and at least five human enzymes. In pre-clinical development, the human aspartyl proteases are used to counter-screen HIV-1 protease inhibitors for selectivity toward HIV-1 protease. However, selectivity toward HIV-1 protease can vary widely across HIV-1 protease inhibitors (Ohtaka, H., et al., Int J Biochem Cell Biol, 36(9):1787-99 (2004)).

The present invention provides, for the first time, an in vitro assay for identifying protease inhibitors that either lack or have a lower propensity for causing metabolic abnormalities in patients.

The present invention also provides genetic polymorphisms in the resistin gene which may cause alterations in the function and/or expression of resistin. Such polymorphisms may genetically predispose certain individuals to an increased risk of developing metabolic abnormalities, particularly in response to HIV protease-inhibitor therapy. Genotypes of such polymorphisms may predict each individual's susceptibility to metabolic abnormalities, and thus will be useful in identifying a group of patients that may be subject to modified HAART treatment regimens. Alternatively, the identification of such a group may preclude one or more individuals within said group from being administered HAART therapy.

SUMMARY OF THE INVENTION

Figure 2:
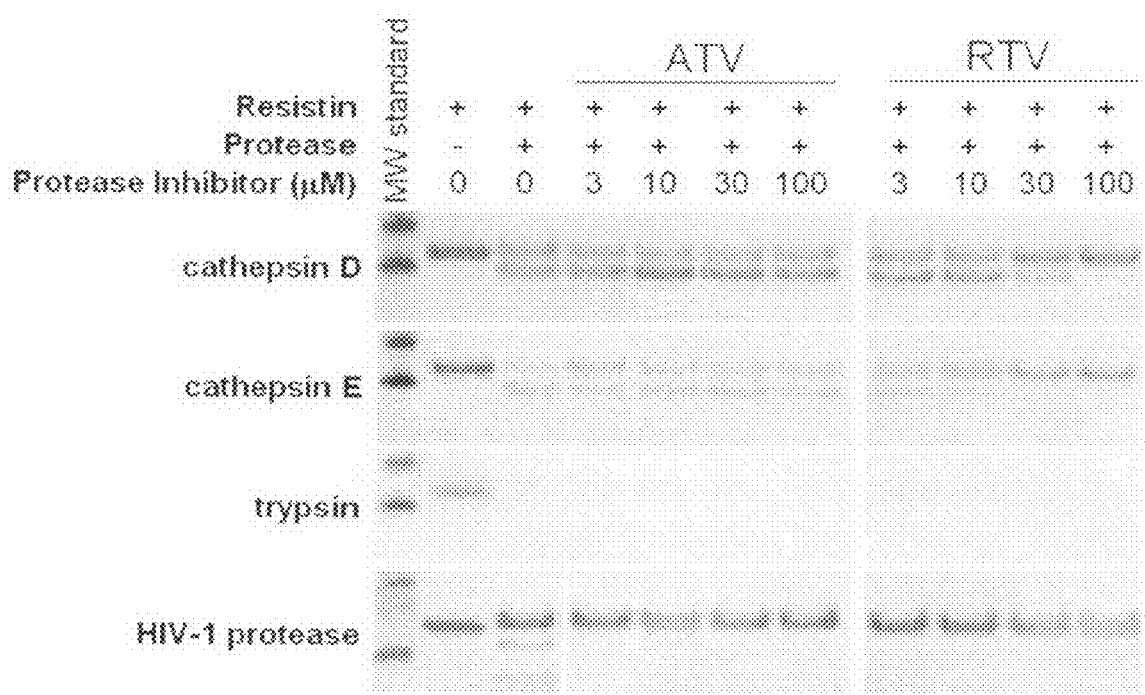

The present invention also relates to a method for screening for HIV-1 protease inhibitor compounds with a diminished ability to increase an individuals likelihood of developing HIV-1 protease inhibitor-dependent metabolic abnormalities upon the administration of the same. In specific embodiments of the invention, such a method comprises the step of combining a mixture of resistin and cathepsin D or E with either one or more test drugs, compounds, or other therapeutic agents, or a control compound as shown in FIG. 2; followed by the step of measuring the level of proteolyzed resistin between the test and control samples, and selecting the test compound with a diminished ability to inhibit cathepsin D- or cathepsin E-dependent degradation of resistin relative to a control compound.

The present invention relates to methods of predicting whether a patient has an increased risk of developing HIV-1 protease inhibitor-dependent metabolic abnormalities upon the administration of a pharmaceutically acceptable level of a HIV-1 protease inhibitor; whether said patient requires a lower level of administered HIV-1 protease inhibitor to limit the risk of developing said HIV-1 protease inhibitor-dependent metabolic abnormalities; or whether said patient may be administered a higher level of administered HIV-1 protease inhibitor without the risk or of a lower risk of developing said HIV-1 protease inhibitor-dependent metabolic abnormalities, comprising the step of assessing the level of resistin expression or resistin plasma/serum levels resulting from the administration of a HIV-1 protease inhibitor relative to a control compound, wherein an elevated level of resistin expression or resistin plasma/serum levels is indicative of an increased risk of developing HIV-1 protease inhibitor-dependent metabolic abnormalities subsequent to the administration of a HIV-1 protease inhibitor.

The invention relates to a nucleic acid molecule which comprises, or alternatively consists of, at least one single nucleotide polymorphism within the resistin genomic sequence at a specific polymorphic locus. In a particular embodiment the invention relates to the variant allele of the resistin gene or polynucleotide having at least one single nucleotide polymorphism, which variant allele differs from a reference allele by one nucleotide at the site(s) identified in FIGS. 3A-B, and/or FIGS. 4A-B, or elsewhere herein. The complementary sequence of each of these nucleic acid molecules are also provided. The nucleic acid molecules can be comprised of DNA or RNA, can be double- or single-stranded, and may comprise fragments. Fragments can be, for example, about 5 to about 10, about 5 to about 15, about 10 to about 20, about 15 to about 25, about 10 to about 30, about 10 to about 50, or about 10 to about 100 bases long, and preferably comprise at least one polymorphic allele.

In another embodiment, the invention relates to the reference or wild type allele of a gene or polynucleotide having a polymorphic locus, in which said reference or wild type allele differs from a variant allele by one nucleotide at the polymorphic site(s) identified in FIGS. 3A-B, and/or FIGS. 4A-B, or elsewhere herein. The complementary sequence of each of these nucleic acid molecules are also provided. The nucleic acid molecules can be comprised of DNA or RNA, can be double- or single-stranded, and may comprise fragments. Fragments can be, for example, about 5 to about 10, about 5 to about 15, about 10 to about 20, about 15 to about 25, about 10 to about 30, about 10 to about 50, or about 10 to about 100 bases long, and preferably comprise at least one polymorphic locus.

The invention further provides variant and reference allele-specific oligonucleotides that hybridize to a nucleic acid molecule comprising at least one polymorphic locus, in addition to the complement of said oligonucleotide. These oligonucleotides can be probes or primers.

The invention further provides oligonucleotides that may be used to amplify a portion of either the variant or reference sequences comprising at least one polymorphic locus of the present invention, in addition to providing oligonucleotides that may be used to sequence said amplified sequence. The invention further provides a method of analyzing a nucleic acid from a DNA sample using said amplification and sequencing primers to assess whether said sample contains the reference or variant nucleotide (allele) at the polymorphic locus, comprising the steps of amplifying a sequence using appropriate oligonucleotide primers for amplifying across a polymorphic locus, and sequencing the resulting amplified product using appropriate sequencing primers to sequence said product to determine whether the variant or reference base is present at the polymorphic locus.

The invention further provides a method of analyzing a nucleic acid from patient sample(s) using said amplification and sequencing primers to assess whether said sample(s) contain the reference or variant nucleotide (allele) at the polymorphic locus in an effort to identify populations at risk of developing HIV-1 protease inhibitor-dependent metabolic abnormalities upon administration of a HIV-1 protease inhibitor, comprising the steps of amplifying a sequence using appropriate oligonucleotide primers for amplifying across a polymorphic locus, and sequencing the resulting amplified product using appropriate sequencing primers to sequence said product to determine whether the variant or reference nucleotide is present at the polymorphic locus.

The invention further provides oligonucleotides that may be used to genotype patient sample(s) to assess whether said sample(s) contain the reference or variant nucleotide (allele) at the polymorphic site(s). The invention provide a method of using oligonucleotides that may be used to genotype a patient sample to assess whether said sample contains the reference or variant nucleotide (allele) at the polymorphic locus. An embodiment of the method comprises the steps of amplifying a sequence using appropriate oligonucleotide primers for amplifying across a polymorphic locus, and subjecting the product of said amplification to a genetic bit analysis (GBA) reaction.

The invention provides a method of using oligonucleotides that may be used to genotype patient sample(s) to identify individual(s) at risk of developing HIV-1 protease inhibitor-dependent metabolic abnormalities upon administration of a HIV-1 protease inhibitor to assess whether said sample(s) contains the reference or variant nucleotide (allele) at one or more polymorphic loci. An embodiment of the method comprises the steps of amplifying a sequence using appropriate oligonucleotide primers for amplifying across a polymorphic locus, and subjecting the product of said amplification to a genetic bit analysis (GBA) reaction, and optionally determining the statistical association between either the reference or variant allele at the polymorphic site(s) to the incidence of HIV-1 protease inhibitor-dependent metabolic abnormalities.

The invention provides a method of using oligonucleotides that may be used to genotype patient sample(s) to identify ethnic population(s) that may be at risk of developing HIV-1 protease inhibitor-dependent metabolic abnormalities upon administration of a HIV-1 protease inhibitor to assess whether said sample(s) contains the reference or variant nucleotide (allele) at one or more polymorphic loci comprising the steps of amplifying a sequence using appropriate oligonucleotide primers for amplifying across a polymorphic locus, and subjecting the product of said amplification to a genetic bit analysis (GBA) reaction, and optionally determining the statistical association between either the reference or variant allele at the polymorphic site(s) to the incidence of HIV-1 protease inhibitor-dependent metabolic abnormalities.

The invention further provides a method of analyzing a nucleic acid from one or more individuals. The method allows the determination of whether the reference or variant base is present at any one, or more, of the polymorphic sites identified FIGS. 3A-B, and/or FIGS. 4A-B, or elsewhere herein. Optionally, a set of nucleotides occupying a set of the polymorphic loci shown in FIGS. 3A-B, and/or FIGS. 4A-B, or elsewhere herein, is determined. This type of analysis can be performed on a number of individuals, who are also tested (previously, concurrently or subsequently) for the presence of HIV-1 protease inhibitor-dependent metabolic abnormalities. The presence or absence of a HIV-1 protease inhibitor-dependent metabolic abnormalities phenotype is then correlated with said nucleotide or set of nucleotides present at the polymorphic locus or loci in the individuals tested.

The invention further relates to a method of predicting the presence, absence, likelihood of the presence or absence, or severity of a HIV-1 protease inhibitor-dependent metabolic abnormalities or related disorder associated with a particular genotype. The method comprises obtaining a nucleic acid sample from an individual and determining the identity of one or more nucleotides at specific polymorphic loci of nucleic acid molecules described herein, wherein the presence of a particular base at that site is correlated with the incidence of HIV-1 protease inhibitor-dependent metabolic abnormalities or related disorder, thereby predicting the presence, absence, likelihood of the presence or absence, or severity, of the HIV-1 protease inhibitor-dependent metabolic abnormalities phenotype or related disorder in the individual.

The invention further relates to polynucleotides having one or more polymorphic loci comprising one or more variant alleles. The invention also relates to said polynucleotides lacking a start codon. The invention further relates to polynucleotides of the present invention containing one or more variant alleles wherein said polynucleotides encode a polypeptide of the present invention. The invention relates to polypeptides of the present invention containing one or more variant amino acids encoded by one or more variant alleles.

The present invention relates to antisense oligonucleotides capable of hybridizing to the polynucleotides of the present invention. Preferably, such antisense oligonucleotides are capable of discriminating between the reference or variant allele of the polynucleotide, preferably at one or more polymorphic sites of said polynucleotide.

The present invention relates to siRNA or RNAi oligonucleotides capable of hybridizing to the polynucleotides of the present invention. Preferably, such siRNA or RNAi oligonucleotides are capable of discriminating between the reference or variant allele of the polynucleotide, preferably at one or more polymorphic sites of said polynucleotide.

The present invention also relates to zinc finger proteins capable of binding to the polynucleotides of the present invention. Preferably, such zinc finger proteins are capable of discriminating between the reference or variant allele of the polynucleotide, preferably at one or more polymorphic sites of said polynucleotide.

The present invention also relates to recombinant vectors, which include the isolated nucleic acid molecules of the present invention, and to host cells containing the recombinant vectors, as well as to methods of making such vectors and host cells, in addition to their use in the production of polypeptides or peptides provided herein using recombinant techniques. Synthetic methods for producing the polypeptides and polynucleotides of the present invention are provided. Also provided are diagnostic methods for detecting diseases, disorders, and/or conditions related to the polypeptides and polynucleotides provided herein, and therapeutic methods for treating such diseases, disorders, and/or conditions. The invention further relates to screening methods for identifying binding partners of the polypeptides.

The invention relates to a method of analyzing at least one nucleic acid sample, comprising the step of determining the nucleic acid sequence from one or more samples at one or more polymorphic loci in the human resistin gene, wherein the presence of the reference allele at said one or more polymorphic loci is indicative of an increased risk of developing HIV-1 protease inhibitor-dependent metabolic abnormalities in a patient receiving HIV-1 protease inhibitor therapy.

The invention relates to a method of analyzing at least one nucleic acid sample, comprising the step of determining the nucleic acid sequence from one or more samples at one or more polymorphic loci in the human resistin gene, wherein the presence of the variant allele at said one or more polymorphic loci is indicative of a decreased risk of developing HIV-1 protease inhibitor-dependent metabolic abnormalities in a patient receiving HIV-1 protease inhibitor therapy.

The invention further relates to a method of constructing haplotypes using the isolated nucleic acids referred to in FIGS. 3A-B and/or FIGS. 4A-B, or elsewhere herein, comprising the step of grouping at least two said nucleic acids.

The invention further relates to a method of constructing haplotypes further comprising the step of using said haplotypes to identify an individual for the presence of HIV-1 protease inhibitor-dependent metabolic abnormalities or related disease phenotype, and correlating the presence of the disease phenotype with said haplotype.

The invention further relates to a library of nucleic acids, each of which comprises one or more polymorphic positions within a gene encoding the human resistin protein, wherein said polymorphic positions are selected from a group consisting of the polymorphic positions provided in FIGS. 3A-B and FIGS. 4A-B.

The invention further relates to a library of nucleic acids, wherein the sequence at said aforementioned polymorphic position is selected from the group consisting of the polymorphic position identified in FIGS. 3A-B, and/or FIGS. 4A-B, or elsewhere herein, the complimentary sequence of said sequences, and/or fragments of said sequences.

The invention further relates to a kit for identifying an individual at risk of developing HIV-1 protease inhibitor-dependent metabolic abnormalities or related disorder upon administration of a pharmaceutically acceptable amount of a HIV-1 protease inhibitor, wherein said kit comprises oligonucleotide primers capable of identifying the nucleotide residing at one or more polymorphic loci of the human resistin gene, wherein the presence of the variant allele at said one or more polymorphic loci is indicative of a decreased risk of developing HIV-1 protease inhibitor-dependent metabolic abnormalities in a patient receiving HIV-1 protease inhibitor therapy, while the presence of the reference allele at said one or more polymorphic loci is indicative of an increased risk of developing HIV-1 protease inhibitor-dependent metabolic abnormalities in a patient receiving HIV-1 protease inhibitor therapy.

The invention further relates to a kit for identifying an individual at risk of developing HIV-1 protease inhibitor-dependent metabolic abnormalities or related disorder upon administration of a pharmaceutically acceptable amount of a HIV-1 protease inhibitor, wherein said kit comprises oligonucleotide primers capable of identifying the nucleotide residing at one or more polymorphic loci of the human resistin gene, wherein the presence of the variant allele at said one or more polymorphic loci is indicative of a decreased risk of developing HIV-1 protease inhibitor-dependent metabolic abnormalities in a patient receiving HIV-1 protease inhibitor therapy, while the presence of the reference allele at said one or more polymorphic loci is indicative of an increased risk of developing HIV-1 protease inhibitor-dependent metabolic abnormalities in a patient receiving HIV-1 protease inhibitor therapy, and wherein said oligonucleotides hybridize immediately adjacent to said one or more polymorphic positions, or wherein said primer(s) hybridizes to said polymorphic positions such that the central position of the primer aligns with the polymorphic position of said gene.

The invention further relates to a method for predicting the likelihood that an individual will be diagnosed as being at risk of developing HIV-1 protease inhibitor-dependent metabolic abnormalities or related disorder upon administration of a pharmaceutically acceptable amount of a HIV-1 protease inhibitor comprising the step of determining the nucleotide present within at least one or more nucleic acid sample(s) from an individual to be assessed at one or more polymorphic position(s) of the human resistin gene sequence selected from the group consisting of: SEQ ID NOS:1 and/or 2, wherein the presence of the reference nucleotide at the one or more polymorphic position(s) indicates that the individual has an increased likelihood of being diagnosed as at risk of developing HIV-1 protease inhibitor-dependent metabolic abnormalities or related disorder upon administration of a pharmaceutically acceptable amount of an HIV-1 protease inhibitor as compared to an individual having the variant allele at said polymorphic position(s).

The invention further relates to a method for predicting the likelihood that an individual will be diagnosed as being at risk of developing a HIV-1 protease inhibitor-dependent metabolic abnormalities or related disorder upon administration of a pharmaceutically acceptable amount of a HIV-1 protease inhibitor comprising the step of determining the nucleotide present within at least one or more nucleic acid sample(s) from an individual to be assessed at one or more polymorphic position(s) of the human resistin gene sequence selected from the group consisting of: SEQ ID NOS:1 and/or 2, wherein the presence of the variant nucleotide at the one or more polymorphic position(s) indicates that the individual has an decreased likelihood of being diagnosed as at risk of developing HIV-1 protease inhibitor-dependent metabolic abnormalities or related disorder upon administration of a pharmaceutically acceptable amount of an HIV-1 protease inhibitor as compared to an individual having the reference allele at said polymorphic position(s).

The invention further relates to a method for predicting the likelihood that an individual will be diagnosed as being at risk of developing HIV-1 protease inhibitor-dependent metabolic abnormalities or related disorder upon administration of a pharmaceutically acceptable amount of a HIV-1 protease inhibitor comprising the step of determining the nucleotide present within at least one or more nucleic acid sample(s) from an individual to be assessed at one or more polymorphic position(s) of the human resistin gene sequence selected from the group consisting of: nucleotide position 1398 of SEQ ID NOS:1 or 2, wherein the presence of the reference nucleotide at the one or more polymorphic position(s) indicates that the individual has an increased likelihood of being diagnosed as at risk of developing HIV-1 protease inhibitor-dependent metabolic abnormalities or related disorder upon administration of a pharmaceutically acceptable amount of a HIV-1 protease inhibitor as compared to an individual having the variant allele at said polymorphic position(s).

The invention further relates to a method for predicting the likelihood that an individual will be diagnosed as being at risk of developing a HIV-1 protease inhibitor-dependent metabolic abnormalities or related disorder upon administration of a pharmaceutically acceptable amount of a HIV-1 protease inhibitor comprising the step of determining the nucleotide present within at least one or more nucleic acid sample(s) from an individual to be assessed at one or more polymorphic position(s) of the human resistin gene sequence selected from the group consisting of: nucleotide position 1398 of SEQ ID NOS:1 or 2, wherein the presence of the variant nucleotide at the one or more polymorphic position(s) indicates that the individual has a decreased likelihood of being diagnosed as at risk of developing HIV-1 protease inhibitor-dependent metabolic abnormalities or related disorder upon administration of a pharmaceutically acceptable amount of a HIV-1 protease inhibitor as compared to an individual having the reference allele at said polymorphic position(s).

A method of decreasing the risk of a patient developing HIV-1 protease inhibitor-dependent metabolic abnormalities upon administration of an HIV-1 protease inhibitor comprising the step of administering either an agent that inhibits resistin activity, or an agent that decreases the expression level of resistin in a patient, wherein said agent is a PPARγ agonist, including but not limited to either rosiglitazone or pioglitazone.

A method of decreasing the level of HIV-1 protease inhibitor-dependent metabolic abnormalities in a patient comprising the step of administering either an agent that inhibits resistin activity, or an agent that decreases the expression level of resistin in a patient in response to or in combination with the administration of an HIV-1 protease inhibitor, wherein said agent is a PPARγ agonist, including but not limited to either rosiglitazone or pioglitazone, or both rosiglitazone or pioglitazone.

A method of identifying HIV patients who may benefit from the administration of a pharmaceutically acceptable amount of atazanavir, comprising the step of comparing the plasma/serum level of resistin in a patient sample relative to a reference sample, wherein an elevated level of resistin relative to the reference sample is indicative of a patient who may have an increased risk of developing HIV-1 protease inhibitor-dependent metabolic abnormalities and who would benefit from the administration of a pharmaceutically acceptable amount of atazanavir.

BRIEF DESCRIPTION OF THE FIGURES/DRAWINGS

FIG. 1 shows that resistin is cleaved by the aspartyl proteases HIV-1 protease, Cathepsin D and Cathepsin E. In each reaction, 1 υg of alkylated and reduced resistin was co-incubated for 24 hr with 1 υg HIV-1 protease, 0.1 υg Cathepsin D, 0.1 υg Cathepsin E, 0.1 υg trypsin or 0.1 υg renin. Control experiments were also performed, in parallel, in which either protease or resistin was omitted from the reaction, respectively. Protease digestion products were separated by 4-12% SDS-PAGE, followed by coomassie blue staining. Abbreviations are as follows: resistin ("Retn"), HIV-1 protease ("HIV-1 PR"); cathepsin D ("CathD"); cathepsin E ("CathE"); trypsin ("Trp"); and renin ("Ren"). Arrows indicate resistin cleavage products.

FIG. 2 shows an evaluation of HIV-1 protease inhibitors on cleavage of resistin by proteases. Protease digestion experiments were performed as in FIG. 1 with the addition of atazanavir ("ATV"), ritonavir ("RTV") or lopinovir ("LPV") at the respective concentrations indicated.

FIGS. 3A-B show the polynucleotide sequence (SEQ ID NO:1) of SNP1 allele C of the human resistin genomic sequence comprising, or alternatively consisting of, a predicted polynucleotide polymorphic locus located at nucleotide 1398 of SEQ ID NO:1. The polynucleotide sequence contains a sequence of 2369 nucleotides. The nucleotide at the polymorphic locus within this allele is a "C" and is denoted in bold and double underlining. Exons encoding the resistin polypeptide are denoted by single underlining, while non-underlined sequence represent introns.

FIGS. 4A-B show the polynucleotide sequence (SEQ ID NO:2) of SNP1 allele T of the human resistin genomic sequence comprising, or alternatively consisting of, a predicted polynucleotide polymorphic locus located at nucleotide 1398 of SEQ ID NO:2. The polynucleotide sequence contains a sequence of 2369 nucleotides. The nucleotide at the polymorphic locus within this allele is a "T" and is denoted in bold and double underlining. Exons encoding the resistin polypeptide are denoted by single underlining, while non-underlined sequence represents introns.

FIG. 5 shows the statistical association between human resistin SNP1 alleles "C" and "T" with the incidence of HIV-1 protease inhibitor-dependent metabolic abnormalities in patients administered HAART therapy. Results are shown in terms of fold incidence of each genotype residing in a patient that was part of the high-risk cluster for HIV-1 protease inhibitor-dependent metabolic abnormalities. As shown, "T" allele homozygous patients ("T/T") at the SNP1 locus have the highest incidence of HIV-1 protease inhibitor-dependent metabolic abnormalities; heterozygous patients ("C/T") at the SNP1 locus have a lower incidence of HIV-1 protease inhibitor-dependent metabolic abnormalities compared to homozygous "T/T" allele patients; while "C" allele homozygous patients ("C/C") at the SNP1 locus have a significantly lower incidence of HIV-1 protease inhibitor-dependent metabolic abnormalities compared to homozygous "T" and heterozygous ("C/T") allele patients.

Table I provides a summary of the SNPs of the present invention.

DETAILED DESCRIPTION OF THE INVENTION

The present invention relates to a method of screening for HIV-1 protease inhibitor compounds with diminished ability to increase an individuals likelihood of developing HIV-1 protease inhibitor-dependent metabolic abnormalities upon the administration of the same. The present invention is based on the novel discovery that resistin is sensitive to proteolytic degradation by aspartyl proteases cathepsin D and E as shown in FIG. 1. Since cathepsin D and E are inhibited by some HIV-1 protease inhibitors, inhibition of cathepsin D and E can result in increased levels of resistin and thus result in metabolic abnormalities. The method of the present invention comprises the step of incubating a mixture of resistin and cathepsin D or E with either one or more test drugs, compounds, or therapeutic agents, in addition to a control compound as shown in FIG. 2; followed by the step of measuring the level of proteolyzed resistin between the test and control samples, and selecting the test compound with a diminished ability to inhibit cathepsin D- or cathepsin E-dependent degradation of resistin relative to a control compound. Such an HIV-1 protease inhibitor compound would be expected to have a diminished ability to cause metabolic abnormalities in a patient.

The present invention also relates to a nucleic acid molecule comprising a single nucleotide polymorphism (SNP) at a specific location, referred to herein as the polymorphic locus, and complements thereof. The nucleic acid molecule, e.g., a gene, which includes the SNP has at least two alleles, referred to herein as the reference allele and the variant allele. The reference allele (prototypical or wild type allele) typically corresponds to the nucleotide sequence of the native form of the nucleic acid molecule.

The present invention pertains to novel polynucleotides of the human resistin gene comprising at least one single nucleotide polymorphism (SNP) which has been shown to be associated with the incidence of HIV-1 protease inhibitor-dependent metabolic abnormalities in patients administered HIV-1 protease inhibitors. These resistin SNPs were identified by sequencing the resistin genomic sequence of a large number of individuals that were subjected to HIV-1 protease inhibitor therapy, and comparing the resistin sequences of those individuals who developed HIV-1 protease inhibitor-dependent metabolic abnormalities to those individuals who did not develop HIV-1 protease inhibitor-dependent metabolic abnormalities. Each of the novel resistin SNPs were located in non-coding regions of the resistin gene and are thought to affect the expression levels of resistin in those patients containing one or more of these SNPs.

The present invention also relates to variant alleles of the described gene and to complements of the variant alleles. The variant allele differs from the reference allele by one nucleotide at the polymorphic locus identified in the FIGS. 3A-B, and/or FIGS. 4A-B.

The invention further relates to fragments of the variant alleles and portions of complements of the variant alleles which comprise the site of the SNP (e.g., polymorphic locus) and are at least 10 nucleotides in length. Fragments can be, for example, about 5-10, about 5-15, about 10-20, about 5-25, about 10-30, about 10-50 or about 10-100 bases long. For example, a portion of a variant allele which is about 10 nucleotides in length comprises at least one single nucleotide polymorphism (the nucleotide which differs from the reference allele at the polymorphic locus) and nine additional nucleotides which flank the site in the variant allele. These additional nucleotides can be on one or both sides of the polymorphism. Polymorphisms which are the subject of this invention are defined in FIGS. 3A-B, and/or FIGS. 4A-B herein.

Specifically, the invention relates to the human resistin gene having a nucleotide sequence according to FIGS. 3A-B or FIGS. 4A-B (SEQ ID NOs:1 or 2) comprising a single nucleotide polymorphism at a polymorphic locus at nucleotide 1398 of SEQ ID NOs:1 or 2. The reference nucleotide for the polymorphic locus at nucleotide 1398 is "C". The variant nucleotide for the polymorphic locus at nucleotide 1398 is "T". The nucleotide sequences of the present invention can be double- or single-stranded.

The invention further relates to a portion of the human resistin gene comprising one or more polymorphic loci selected from the group consisting of: nucleotide 1398 of SEQ ID NOs:1 or 2.

The single nucleotide polymorphisms described herein derive from the resistin gene that have been shown to be associated, for the first time, with the incidence of HIV-1 protease inhibitor-dependent metabolic abnormalities or related disorders. Specifically, the reference single nucleotide polymorphisms of the human resistin gene described herein have been demonstrated to statistically increase an individuals susceptibility to developing HIV-1 protease inhibitor-dependent metabolic abnormalities upon the administration of an increased dose of a HIV-1 protease inhibitor.

The human resistin gene was chosen as a candidate gene to investigate the potential of it comprising one or more single nucleotide polymorphisms associated with HIV-1 protease inhibitor-dependent metabolic abnormalities phenotype, and in particular, the potential of identifying a resistin SNP associated with the incidence of HIV-1 protease inhibitor-dependent metabolic abnormalities phenotype upon the administration of an HIV-1 protease inhibitor, based upon the association of resistin in glucose metabolism, obesity and insulin resistance.

The invention further provides allele-specific oligonucleotides that hybridize to the human resistin gene, or fragments or complements thereof, comprising one or more single nucleotide polymorphisms and/or polymorphic locus. Such oligonucleotides are expected to hybridize to one polymorphic allele of the nucleic acid molecules described herein but not to the other polymorphic allele(s) of the sequence. Thus, such oligonucleotides can be used to determine the presence or absence of particular alleles of the polymorphic sequences described herein and to distinguish between reference and variant allele for each form. These oligonucleotides can be probes or primers.

The invention further provides a method of analyzing a nucleic acid from an individual to identify the presence or absence of a particular nucleotide at a given polymorphic locus and to distinguish between the reference and variant allele at each locus. The method determines which base is present at any one of the polymorphic loci shown in FIGS. 3A-B or FIGS. 4A-B (SEQ ID NOs:1 or 2), or elsewhere herein. Optionally, a set of bases occupying a set of the polymorphic loci shown in FIGS. 3A-B or FIGS. 4A-B (SEQ ID NOs:1 or 2) is determined. This type of analysis can be performed on a number of individuals, who are also tested (previously, concurrently or subsequently) for the presence of HIV-1 protease inhibitor-dependent metabolic abnormalities phenotype in the presence or absence of a HIV-1 protease inhibitor. The presence or absence of HIV-1 protease inhibitor-dependent metabolic abnormalities phenotype is then correlated with a base or set of bases present at the polymorphic locus or loci in the patient and/or sample tested.

Thus, the invention further relates to a method of predicting the presence, absence, likelihood of the presence or absence, or severity of a particular HIV-1 protease inhibitor-dependent metabolic abnormalities phenotype associated with a particular genotype in the presence or absence of an increased dose of a HIV-1 protease inhibitor. The method comprises obtaining a nucleic acid sample from an individual and determining the identity of one or more bases (nucleotides) at on or more polymorphic loci of the nucleic acid molecules described herein, wherein the presence of a particular base is correlated with the incidence of HIV-1 protease inhibitor-dependent metabolic abnormalities phenotype or an increased risk of developing HIV-1 protease inhibitor-dependent metabolic abnormalities phenotype in the presence of a HIV-1 protease inhibitor, thereby predicting the presence, absence, likelihood of the presence or absence, or severity of HIV-1 protease inhibitor-dependent metabolic abnormalities in the individual or sample. The correlation between a particular polymorphic form of a gene and a phenotype can thus be used in methods of diagnosis of that phenotype, as well as in the development of treatments for the phenotype.

DEFINITIONS

An "oligonucleotide" can be DNA or RNA, and single- or double-stranded. An oligonucleotide may be used as either a "primer" or a "probe". Oligonucleotides can be naturally occurring or synthetic, but are typically prepared by synthetic means. An oligonucleotide primer, for example, may be designed to hybridize to the complementary sequence of either the sense or antisense strand of a specific target sequence, and may be used alone or as a pair, such as in DNA amplification reactions, and may or may not comprise one or more polymorphic loci of the present invention. An oligonucleotide probe may also be designed to hybridize to the complementary sequence of either the sense or antisense strand of a specific target sequence, and may be used alone or as a pair, such as in DNA amplification reactions, but necessarily will comprise one or more polymorphic loci of the present invention. Preferred oligonucleotides of the invention include fragments of DNA, or their complements thereof, of the human resistin gene, and may comprise one or more of the polymorphic loci shown or described in FIGS. 3A-B, FIGS. 4A-B, or as described elsewhere herein. The fragments can be between 10 and 250 bases, and, in specific embodiments, are between about 5 to about 10, about 5 to about 15, about 10 to about 20, about 15 to about 25, about 10 to about 30, about 10 to about 50, or about 10 to about 100 bases in length. For example, the fragment can be 40 bases in length. The polymorphic locus can occur within any nucleotide position of the fragment, including at either terminus or directly in the middle, for example. The fragments can be from any of the allelic forms of DNA shown or described herein.

As used herein, the terms "nucleotide", "base" and "nucleic acid" are intended to be equivalent. The terms "nucleotide sequence", "nucleic acid sequence", "nucleic acid molecule" and "segment" are intended to be equivalent.

Hybridization probes are oligonucleotides which bind in a base-specific manner to a complementary strand of nucleic acid and are designed to identify the allele at one or more polymorphic loci within the resistin gene of the present invention. Such probes include peptide nucleic acids, as described in Nielsen et al., Science 254, 1497-1500 (1991). Probes can be any length suitable for specific hybridization to the target nucleic acid sequence. The most appropriate length of the probe may vary depending upon the hybridization method in which it is being used; for example, particular lengths may be more appropriate for use in microfabricated arrays, while other lengths may be more suitable for use in classical hybridization methods. Such optimizations are known to the skilled artisan. Suitable probes can range from about 12 nucleotides to about 25 nucleotides in length. For example, probes and primers can be about 4, 6, 8, 10, 12, 14, 16, 18, 20, 22, 24, 25, 26, or about 40 nucleotides in length. The probe preferably comprises at least one polymorphic locus occupied by any of the possible variant nucleotides. For comparison purposes, the present invention also encompasses probes that comprise the reference nucleotide at least one polymorphic locus. The nucleotide sequence can correspond to the coding sequence of the allele or to the complement of the coding sequence of the allele, where applicable.

As used herein, the term "primer" refers to a single-stranded oligonucleotide which acts as a point of initiation of template-directed DNA synthesis under appropriate conditions. Such DNA synthesis reactions may be carried out in the traditional method of including all four different nucleoside triphosphates (e.g., in the form of phosphoramidates, for example) corresponding to adenine, guanine, cytosine and thymine or uracil nucleotides, and an agent for polymerization, such as DNA or RNA polymerase or reverse transcriptase in an appropriate buffer and at a suitable temperature. Alternatively, such a DNA synthesis reaction may utilize only a single nucleoside (e.g., for single base-pair extension assays). The appropriate length of a primer depends on the intended use of the primer, but typically ranges from about 10 to about 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

As used herein, "linkage" describes the tendency of genes, alleles, loci or genetic markers to be inherited together as a result of their location on the same chromosome. It can be measured by percent recombination between the two genes, alleles, loci or genetic markers.

As used herein, "polymorphism" refers to the occurrence of two or more genetically determined alternative sequences or alleles in a population. A "polymorphic locus" is a marker or site at which divergence from a reference allele occurs. The phrase "polymorphic loci" is meant to refer to two or more markers or sites at which divergence from two or more reference alleles occurs. Preferred markers have at least two alleles, each occurring at frequency of greater than 1%, and more preferably greater than 10% or 20% of a selected population. A polymorphic locus may be as small as one base pair. Polymorphic loci include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the "reference form" or "reference allele" and other allelic forms are designated as alternative forms or "variant alleles". The allelic form occurring most frequently in a selected population is sometimes referred to as the wild type form. Diploid organisms may be homozygous or heterozygous for allelic forms. A diallelic or biallelic polymorphism has two forms. A triallelic polymorphism has three forms.

As used herein, the term "genotype" is meant to encompass the particular allele present at a polymorphic locus of a DNA sample, a gene, and/or chromosome.

As used herein, the term "haplotype" is meant to encompass the combination of genotypes across two or more polymorphic loci of a DNA sample, a gene, and/or chromosome, wherein the genotypes are closely linked, may be inherited together as a unit, and may be in linkage disequilibrium relative to other haplotypes and/or genotypes of other DNA samples, genes, and/or chromosomes.

As used herein, the term "linkage disequilibrium" refers to a measure of the degree of association between two alleles in a population. For example, when alleles at two distinctive loci occur in a sample more frequently than expected given the known allele frequencies and recombination fraction between the two loci, the two alleles may be described as being in "linkage disequilibrium".

As used herein, the terms "genotype assay" and "genotype determination", and the phrase "to genotype" or the verb usage of the term "genotype" are intended to be equivalent and refer to assays designed to identify the allele or alleles at a particular polymorphic locus or loci in a DNA sample, a gene, and/or chromosome. Such assays may employ single base extension reactions, DNA amplification reactions that amplify across one or more polymorphic loci, or may be as simple as sequencing across one or more polymorphic loci. A number of methods are known in the art for genotyping, with many of these assays being described herein or referred to herein.

Work described herein pertains to the resequencing of the human resistin gene in a large number of individuals to identify polymorphisms associated with the incidence of HIV-1 protease inhibitor-dependent metabolic abnormalities disorders upon the administration of a HIV-1 protease inhibitor, which may predispose individuals to developing such a disorder. For example, polymorphisms in the resistin gene described herein are associated with the incidence of HIV-1 protease inhibitor-dependent metabolic abnormalities disorders and are useful for predicting the likelihood that an individual will be susceptible to such a disorder, or that such an individual may have an increased susceptibility to such a disorder, upon the administration of a HIV-1 protease inhibitor.

By altering amino acid sequence, SNPs may alter the function of the encoded proteins. The discovery of the SNP facilitates biochemical analysis of the variants and the development of assays to characterize the variants and to screen for pharmaceutical compounds that would interact directly with one or another form of the protein. SNPs (including silent SNPs) may also alter the regulation of the gene at the transcriptional or post-transcriptional level. SNPs (including silent SNPs) also enable the development of specific DNA, RNA, or protein-based diagnostics that detect the presence or absence of the polymorphism in particular conditions.

The phrase "HIV-1 protease inhibitor" is meant to encompass compounds, including, but not limited to, atazanavir, lopinovir, ritonavir, indinavir, saquinavir, ramelteon, tipranavir, nepafenac, deferasirox, fosamprenavir, amprenavir, brecanvir, nelfinavir, as well as any combination and/or boosted formulation of the same.

The phrase "PPAR-agonist" is meant to encompass compounds, including small molecules, antibodies, RNAi reagents, siRNA reagents, antisense compounds, or any compound in general capable of increasing the activity or expression of one or more peroxisome proliferator activator receptors (PPAR), including but not limited to, PPAR-alpha agonists, PPAR-beta agonists, PPAR-gamma agonists, and PPAR-delta agonists, including mono-PPAR-alpha agonists, mono-PPAR-beta agonists, mono-PPAR-gamma agonists, mono-PPAR-delta agonists, dual PPAR-alpha and gamma agonists, and any combination of the same. In addition, such PPAR-agonists are necessarily meant to encompass the following, non-limiting compounds: Muraglitazar, peliglitazar, Farglitazar, thiazolidinediones class of PPAR-agonists, Troglitazone, Pioglitazone, Rosiglitazone, MCC555, KRP297, JTT-501, BM 17.0744, L764486, GW501516, NN622, bezafibrate, gemfibrozil, fibrate class of PPAR-agonists, DRF 2725, WY 14,643, SB 213068, Tesaglitazar (AZ 242), Avandaryl, Naveglitazar, Ragaglitazar (NN622), PLX 204, PLX 134, PLX 203, CS 7017, DRF 10945, AVE 0847, AVE 8134, 641597 (GSK), 590735 (GSK), MK 767, AA 10090, LY 674, LY 929, T 131, DRF 4158, CLX 0921, NS 220, LY 293111, DRF 4832, GW 7282, 501516 (GSK), LG 100754, GW 544, AR H049020, AK-109, E-3030 (Eisai), CS-7017 (Sankyo), DRF-10945, KRP-101, ONO-5129, TY-51501, GSK-677954, LSN-862, LY-518674, GW-590735, KT6-207, K-111 (Roche), Bay-54-9801 (GSK), R-483 (Roche), EMD-336340 (Merck KGaA), LR-90 (Merck KGaA), CLX-0940, CLX-0921, LG-100754, GW-409890, SB-219994, NIP-223, T-174 (Tanabe Seiyaku), balaglitazone (DRF-2593), VDO-52, GW-1929, NC-2100, netoglitazone, ciglitazone, LGD 1268, LG 101506, LGD 1324, GW 9578, Englitazone, and/or Darglitazone.

The phrases "a pharmaceutically acceptable amount of an agent that inhibits resistin activity" and "a pharmaceutically acceptable amount of an agent that decreases the expression level of resistin in a patient" are meant to encompass any inhibitor of resistin, including, but not limited to, small molecule inhibitors, antisense oligonucleotides, RNAi molecules, siRNAi molecules, ribozymes, zinc finger proteins, antibodies, antibody fragments, among other inhibitors directed to renin, otherwise known in the art.

A single nucleotide polymorphism occurs at a polymorphic locus occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations).

A single nucleotide polymorphism usually arises due to substitution of one nucleotide for another at the polymorphic locus. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele. Typically the polymorphic locus is occupied by a base other than the reference base. For example, where the reference allele contains the base "C" at the polymorphic site, the altered allele can contain a "T", "G" or "A" at the polymorphic locus.

For the purposes of the present invention the terms "polymorphic position", "polymorphic site", "polymorphic locus", and "polymorphic allele" shall be construed to be equivalent and are defined as the location of a sequence identified as having more than one nucleotide represented at that location in a population comprising at least one or more individuals, and/or chromosomes.

Probe hybridizations are usually performed under stringent conditions, for example, at a salt concentration of no more than 1 M and a temperature of at least 25° C. For example, conditions of 5×SSPE (750 mM NaCl, mM NaPhosphate, mM EDT A, pH 7.4) and a temperature of 25-30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

The term "isolated" is used herein to indicate that the material in question exists in a physical milieu distinct from that in which it occurs in nature, and thus is altered "by the hand of man" from its natural state.

On one hand, and in specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, and may comprise all or a portion of an intron. In another embodiment, the polynucleotides preferentially do not contain the genomic sequence of the gene or genes flanking the human resistin (i.e., 5' or 3' to the resistin gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

On the other hand, and in specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, comprise a portion of non-coding sequences, comprise a portion of an intron sequence, etc., or any combination of the latter, as disclosed herein. Alternatively, the polynucleotides of the invention may comprise the entire coding sequence, the entire 5' non-coding sequence, the entire 3' non-coding sequence, an entire intron sequence, an entire exon sequence, or any combination of the latter, as disclosed herein. In another embodiment, the polynucleotides may correspond to a genomic sequence flanking a gene (i.e., 5' or 3' to the gene of interest in the genome). In other embodiments, the polynucleotides of the invention may contain the non-coding sequence of more than 1000, 500, 250, 100, 50, 25, 20, 15, 10, 5, 4, 3, 2, or 1 genomic flanking gene(s).

As used herein, a "polynucleotide" refers to a molecule comprising a nucleic acid of SEQ ID NO:1 or 2. For example, the polynucleotide can contain the nucleotide sequence of the full length cDNA sequence, including the 5' and 3' untranslated sequences, the coding region, with or without a signal sequence, the secreted protein coding region, and the genomic sequence with or without the accompanying promoter and transcriptional termination sequences, as well as fragments, epitopes, domains, and variants of the nucleic acid sequence. Moreover, as used herein, a "polypeptide" refers to a molecule having the translated amino acid sequence generated from the polynucleotide as defined.

Unless otherwise indicated, all nucleotide sequences determined by sequencing a DNA molecule herein were determined using an automated DNA sequencer (such as the Model 3730-XL from Applied Biosystems, Inc., and/or ther PE 9700 from Perkin Elmer), and all amino acid sequences of polypeptides encoded by DNA molecules determined herein were predicted by translation of a DNA sequence determined above. The nucleotide sequence can also be determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. Since the present relates to the identification of single nucleotide polymorphisms whereby the novel sequence differs by as few as a single nucleotide from a reference sequence, identified SNPs were multiply verified to ensure each novel sequence represented a true SNP.

Using the information provided herein, a nucleic acid molecule of the present invention encoding a polypeptide of the present invention may be obtained using standard cloning and screening procedures, such as those for cloning cDNAs using mRNA as starting material.

A "polynucleotide" of the present invention also includes those polynucleotides capable of hybridizing, under stringent hybridization conditions, to sequences described herein, or the complement thereof. "Stringent hybridization conditions" refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The term "organism" as referred to herein is meant to encompass any organism referenced herein, though preferably to eukaryotic organisms, more preferably to mammals, and most preferably to humans.

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

The phrase "HIV-1 protease inhibitor-dependent metabolic abnormalities" is meant to encompass the following non-limiting diseases and/or disorders: HAART-associated lipodystrophy, lipodystrophy, fat atrophy, fat hypertrophy, dyslipidemia, insulin resistance, cardiovascular disorders, myocardial infarction, stroke, atherosclerosis, peripheral lipoatrophy, central fat accumulation, hepatic steatosis, lipodystrophy syndrome, lipodystrophy-lie syndromes, hyperglycemia, decreased HDL levels, elevated levels of VLDL, hypertriglyceridemia, hypercholesterolemia, and hyperlipidemia. The definition necessarily encompasses any other diseases and/or disorders that are known to be associated with HIV-1 protease inhibitor administration, in addition to other diseases or disorders disclosed herein.

The term "HAART" is a reference to highly active antiretroviral therapy for the treatment of HIV-1 infection. HAART therapy typically encompasses a double nucleoside (NRTI) backbone plus either a non-nucleoside reverse transcriptase inhibitor (NNRTI) or a ritonavir pharmacologically enhanced protease inhibitor (PI/r). However the actual therapeutic composition in terms of both class and active agent varies depending upon availability of each agent and a patients individual tolerance for each ingredient, among others. Accordingly, use of the term "HAART" is meant to broadly encompass all combinations of active therapeutic agents that the art would ascribe to this term.

The terms "1398T" and "C1398T" are meant to refer to the "t" allele at the polymorphic locus located at nucleotide 1398 of SEQ ID NO:1. One skilled in the art would recognize that reference to this allele is not limited to only SEQ ID NO:1, but rather necessarily also includes any other polynucleotide that may include this sequence, or a portion of this sequence surrounding this locus, on account of SEQ ID NO:1 merely representing a small portion of chromosome 19 encoding the resistin gene.

The term "C1398" is meant to refer to the "c" allele at the polymorphic locus located at nucleotide 1398 of SEQ ID NO:1. One skilled in the art would recognize that reference to this allele is not limited to only SEQ ID NO:1, but rather necessarily also includes any other polynucleotide that may include this sequence, or a portion of this sequence surrounding this locus, on account of SEQ ID NO:1 merely representing a small portion of chromosome 19 encoding the resistin gene.

Methods of Screening for HIV-1 Protease Inhibitors with Diminished Ability to Proteotyically Process Resistin As part of an ongoing effort to understand the mechanistic basis underlying HAART-associated lipodystrophy, resistin was evaluated as a substrate for the endogenous aspartyl proteases renin, cathepsin D, cathepsin E for the viral aspartyl protease encoded by HIV-1.

Resistin was chosen as a candidate substrate based upon genetic data that associated a single nucleotide polymorphism in resistin with the risk of developing lipodystrophy in patients enrolled on HAART therapy. The resistin SNP is described elsewhere herein.

There are at least two, non mutually exclusive, mechanisms that could account for elevated resistin levels in patients on HAART. Because HIV infection itself is considered to be a state of chronic inflammation, it is possible that HIV positive patients express higher circulating levels of resistin compared to healthy subjects. Indeed, it has been demonstrated in vitro and in vivo that treatment with pro-inflammatory cytokines such as interleukin 6, TNF, as well as lipopolysaccharide results in increased resistin expression (Kaser, S., et al., Biochem Biophys Res Commun, 309(2): 286-90 (2003), Lehrke, M., et al., PLoS Med, 1(2):e45 (2004)). Furthermore, in patients treated with HAART, it is conceivable that inhibition of endogenous proteases that regulate steady-state levels of resistin could result in increased circulating resistin levels. In genetically susceptible patients, these mechanisms could contribute to lipodystrophy syndrome.

Resistin is known to form highly-folded, multimers that are maintained via extensive disulfide bridging (Patel, S. D., et al., Science, 304(5674):1154-8 (2004)). Proteins exhibiting these properties are typically refractory to proteolytic cleavage (Patel, S. D., et al., Science, 304(5674):1154-8 (2004)). Consistent with that expectation, preliminary protease digestion experiments revealed that native resistin was refractory to proteolytic cleavage by trypsin, suggestive of a highly folded state (data not shown). Therefore, to evaluate additional proteases, resistin was fully denatured via alkylation and reduction of cysteine residues.

Aspartyl proteases such as cathepsin D and cathepsin E are used to counter screen HIV-1 protease inhibitors for selectivity toward HIV-1 protease. It is well-established that these enzymes display relaxed substrate specificity (Dash, C., et al., Crit. Rev Biochem Mol Biol, 38(2):89-119 (2003), Chou, K. C., et al., Proteins, 24(1): p. 51-72 (1996)), whereas others, such as renin, display more stringent substrate specificity (Dash, C., et al., Crit. Rev Biochem Mol Biol, 38(2):89-119 (2003)). Four aspartyl proteases, HIV-1 protease, cathepsin D, cathepsin E and renin were evaluated for their ability to cleave resistin (MW ca. 10.4 kDa) in vitro. Incubation with HIV-1 protease, cathepsin D and cathepsin E resulted in the appearance of a ca. 7 kDa resistin cleavage product (see FIG. 1). Additional cleavage products were not detectable by SDS-PAGE, suggesting that the remaining ca. 3.4 kDa fragment was further proteolyzed. Consistent with expectation, resistin was completely degraded by the non-specific protease, trypsin, but was refractory to cleavage by the highly specific protease, renin.

The ability of resistin to be proteolytically degraded by the aspartyl proteases cathepsin D and E represents a novel finding and provides a unique insight into the physiological regulation of resistin levels. The connection between resistin, cathepsins D and E, and HAART therapy becomes apparent due to the discovery that some HIV-1 protease inhibitors vary substantially in their selectivity toward HIV-1 protease (i.e. they are also capable of inhibiting cathepsin D and cathepsin E, (Int J Biochem Cell Biol, 36(9):1787-99 (2004)).

The inventors therefore evaluated the protease inhibitors atazanavir and ritonavir for their ability to inhibit the proteolysis of resistin by cathepsin D and cathepsin E. Cleavage of resistin by cathepsin D and cathepsin E was not detectably inhibited by atazanavir, however, cleavage of resistin by cathepsin D and cathepsin E was detectably inhibited by ritonavir at 30 micromolar and 10 micromolar, respectively (see FIG. 2). Cathepsin D and cathepsin E were fully inhibited by ritonavir at 100 micromolar and 30 micromolar, respectively. Consistent with expectation, control experiments revealed that all three protease inhibitors antagonized HIV-1 protease-dependent cleavage of resistin at all concentrations evaluated. As expected, trypsin, an unrelated serine protease, was not detectably inhibited by any protease inhibitor in this study (see FIG. 2).

Additional HIV-1 protease inhibitors were also evaluated in parallel for comparison, including nelfinavir, saquinavir and indinavir. In further support of the hypothesis that inhibition of resistin cleavage by cathepsins D and E is predictive of HIV-1 protease inhibitors that are more likely to cause metabolic abnormalities, cleavage of resistin by cathepsins D and E was prevented by saquinavir, but not by nelfinavir or indinavir (data not shown). Saquinavir is known to be associated with the incidence of HIV-1 protease inhibitor induced metabolic abnormalities (Calza et al., J Antimicrob Chemother. 53(1):10-4 (2004), whereas nelfinavir (Fisac et al., J Clin Endocrinol Metab. 88(11):5186-92 (2003)), or indinavir (Rojas et al., Pharmacoepidemiol Drug Saf. 12(5): 361-9 (2003)) are not.

The sensitivity of cathepsin D and cathepsin E to ritonavir, and the proposed effect of the latter on elevated resistin levels, is indirectly supported by clinical trials demonstrating administration of ritonavir is associated with pronounced metabolic abnormalities relative to other protease inhibitors. Periard et al. show that elevated plasma cholesterol and plasma triglyceride levels were significantly more pronounced in patients administered ritonavir relative to indinavir or nelfinavir (Circulation, 100:700-705 (1999)). Manfredi, R. and Chiodo, F. demonstrated that administration of ritonavir was associated with severe hypertriglyceridaemia compared to patients administered indinavir, while hypercholesterolemia was observed in patients administered ritonavir and indinavir relative to saquinavir (J. Infect., 42:181-188 (2001)). Calza et al., also stated that "hypertriglyceridaemia appear(ed) to be more frequent in patients treated with ritonavir, rinonavir-saquinavir, or ritonavir-lopinovir" (J. Antimicro. Chemo., 53:10-14 (2004).

In addition, atazanavir is known in the art to not result in significant metabolic changes. Cohen et al., describe the results of a head-to-head clinical trial comparing atazanavir with lopinovir/ritonavir therapy and noted that "atazanavir resulted in either no change or decreases in fasting LDL cholesterol, total cholesterol, and fasting triglycerides . . . , whereas lopinovir/ritonavir resulted in increases . . . " (Curr. Med. Res. Opin., 21(10):1683-92 (2005)). Further, Goldsmith et al. states that "Atazanavir was not associated with increases in total cholesterol, low density lipoprotein-cholesterol or triglyceride levels after 108 weeks" in another clinical trial (Drugs, 63(16):1679-93 (2003)).

Although clinical trials directed at assessing the metabolic affects of lopinovir alone appear to be limited because it is typically administered in combination with ritonavir, at least two independent groups published results that indicated lipid abnormalities did not correlate with lopinovir plasma concentrations suggesting the lipid affects were attributable to ritonavir (J. Acquir. Immune. Defic. Syndr. 35(3):324-6 (2004); and J. Acquir. Immune. Defic. Syndr. 36(5):1107-9 (2004)).

Therefore, since HIV-1 protease inhibitors vary in their potential to contribute toward the metabolic side-effects associated with lipodystrophy syndrome (Carr, A., Clin Infect Dis, 30 Suppl 2:S135-42 (2000)), it would be of utility to be able to screen preclinical compounds to reduce the likelihood of a patient developing HIV-1 protease inhibitor-dependent metabolic abnormalities. In this study, the inventors have demonstrated that the HIV-1 protease inhibitors atazanavir, ritonavir and lopinovir differentially inhibit cleavage of resistin by cathepsin D and cathepsin E. Because resistin is associated with obesity and insulin resistance (Rajala, M. W., et al., J Clin Invest, 111(2):225-30 (2003)), and because HIV-1 protease inhibitor therapy can cause hyperlipidemia (Carr, A., Clin Infect Dis, 30 Suppl 2:S135-42 (2000)), it is conceivable, that inhibition of cathepsins D and E by HIV-1 protease inhibitors, may result in elevated resistin levels. In genetically susceptible HIV-1 positive patients on HAART therapy, this may ultimately lead to components of lipodystrophy syndrome and/or metabolic abnormalities, in general.

The present invention relates to a method for screening for HIV-1 protease inhibitor compounds with a diminished ability to increase an individuals likelihood of developing HIV-1 protease inhibitor-dependent metabolic abnormalities upon the administration of the same. In specific embodiments of the invention, such a method comprises the step of combining a mixture of resistin and cathepsin D or E with either one or more test drugs, compounds, or other therapeutic agents, or a control compound; followed by the step of measuring the level of proteolyzed resistin between the test and control samples, and selecting the test compound with a diminished ability to inhibit cathepsin D- or cathepsin E-dependent degradation of resistin relative to a control compound.

The present invention relates to methods of predicting whether a patient has an increased risk of developing HIV-1 protease inhibitor-dependent metabolic abnormalities upon the administration of a pharmaceutically acceptable level of a HIV-1 protease inhibitor; whether said patient requires a lower level of administered HIV-1 protease inhibitor to limit the risk of developing said HIV-1 protease inhibitor-dependent metabolic abnormalities; or whether said patient may be administered a higher level of administered HIV-1 protease inhibitor without the risk or of a lower risk of developing said HIV-1 protease inhibitor-dependent metabolic abnormalities, comprising the step of assessing the level of resistin expression or resistin plasma/serum levels resulting from the administration of a HIV-1 protease inhibitor relative to a control compound, wherein an elevated level of resistin expression or resistin plasma/serum levels is indicative of an increased risk of developing HIV-1 protease inhibitor-dependent metabolic abnormalities subsequent to the administration of a HIV-1 protease inhibitor.

In addition, the expression level or plasma/serum level of human resistin is believed to be significantly elevated in the presence of HIV-1 protease inhibitors that are capable of inhibiting cathepsin D and/or cathepsin E thus suggesting that human resistin may be useful as a biomarker for predicting whether a patient administered an HIV-1 protease inhibitor may develop metabolic abnormalities. In accordance with the present invention, an elevated basal level of resistin prior to the administration of an HIV-1 protease inhibitor would be indicative of an increased risk of developing metabolic abnormalities subsequent to the administration of an HIV-1 protease inhibitor. In addition, an elevated basal level of resistin prior to the administration of an HIV-1 protease inhibitor would be indicative of an even greater increased risk of developing metabolic abnormalities subsequent to the administration of an HIV-1 protease inhibitor capable of inhibiting cathepsin D and/or cathepsin E.

An elevated basal resistin plasma/serum level in a patient may warrant closer monitoring of the patient prior to increasing the level of administered HIV-1 protease inhibitor to limit the risk of developing said HIV-1 protease inhibitor-dependent metabolic abnormalities, particularly if an HIV-1 protease inhibitor capable of inhibiting cathepsin D and/or cathepsin E is administered. Accordingly, an elevated basal resistin plasma/serum level in a patient may warrant lowering the amount of the HIV-1 protease inhibitor administered or changing to another HIV-1 protease inhibitor that does not inhibit cathepsin D and/or cathepsin E, or at least inhibits cathepsin D and/or cathepsin E to a lesser extent. Alternatively, basal or normal plasma/serum levels of resistin in a patient may justify the administration of a higher level of HIV-1 protease inhibitor with a diminished risk of developing HIV-1 protease inhibitor-dependent metabolic abnormalities. Alternatively, elevated basal resistin plasma/serum level in a patient may indicate that the patient may benefit from hypertriglyceridemia therapy which may include administration of bezafibrate either alone or in combination with an HIV-1 protease inhibitor.

In another embodiment of the present invention, human resistin is useful as a biomarker for pre- or post-clinical screening to identify HIV-1 protease inhibitor compounds or combinations of such compounds that are likely to increase the risk of a patient developing HIV-1 protease inhibitor-dependent metabolic abnormalities in response to the administration of HIV-1 protease inhibitor compounds or combinations of such compounds, and thus to prevent or diminish the likelihood of a patient developing HIV-1 protease inhibitor-dependent metabolic abnormalities by either advising patients be monitored more closely if such a compound or combination of compounds are administered at a corresponding higher dose, or by changing the amount of HIV-1 protease inhibitor administered or the composition of the combination. Preferably, such an identified HIV-1 protease inhibitor compound or combinations of such compounds would not be capable of inhibiting cathepsin D and/or cathepsin E.

Cells endogenously expressing human resistin can be treated with at least one test substance, and extracellular and/or intracellular levels of the biomarker resistin polypeptide in the presence and absence of the test substance(s) can be compared. The observation of high levels of the resistin biomarker polypeptide in the presence of the substance(s) can be used to predict which compounds are likely to increase the risk of a patient developing HIV-1 protease inhibitor-dependent metabolic abnormalities in response to the administration of HIV-1 protease inhibitor compounds or combinations of such compounds, and thus to prevent or diminish the likelihood of a patient developing HIV-1 protease inhibitor-dependent metabolic abnormalities by not selecting such a test compound in the screen. In an additional aspect, the assays of the invention are automated for high throughput screening. The results of such screening may be used to determine the need to modify or discontinue an existing treatment.

The present invention also encompasses microarrays, e.g., protein, antibody, or cell-based microarrays, which can be used in conjunction with the disclosed screening assays for measuring the resistin biomarker polypeptide. The protein, antibody, and cell-based microarrays can be used in the manual or automated screening assays of the invention as disclosed herein to test one or more drugs, compounds, or other therapeutic agents. For protein microarrays, polypeptides obtained from resistin expressing cells (e.g., from extracellular media or cell lysates) incubated in the presence and absence of at least one test substance can be affixed to a support, and then contacted with antibodies that specifically bind to the resistin biomarker polypeptide. For antibody microarrays, one or more anti-biomarker antibodies can be affixed to a support, and then contacted with extracellular media or cell lysates obtained from resistin expressing cells incubated in the presence and absence of at least one test substance. For cell-based microarrays, one or more cells can be affixed to a support, and then incubated in the presence and absence of at least one test substance. The microarrays can then be analyzed (e.g., by immunoassay) to determine elevated levels of at least one biomarker polypeptide in the presence of the test substance(s), which can be used to predict which compound are likely to increase the risk of a patient developing HIV-1 protease inhibitor-dependent metabolic abnormalities in response to the administration of HIV-1 protease inhibitor compounds or combinations of such compounds, and thus to prevent or diminish the likelihood of a patient developing HIV-1 protease inhibitor-dependent metabolic abnormalities by either decreasing the level of the administered HIV-1 protease inhibitor compounds or combinations of such compounds, or by changing the HIV-1 protease inhibitor combination administered.

The present invention additionally encompasses kits comprising one or more biomarker polypeptides, and/or anti-biomarker antibodies, which can be used to predict the likelihood of HIV-1 protease inhibitor-dependent metabolic abnormalities of one or more drugs, compounds, or other therapeutic agents. Such kits can be used in clinical or preclinical settings, and can include one or more biomarker polypeptides and anti-biomarker antibodies. In specific aspects of the invention, the kits can include one or more microarrays comprising antibodies that specifically bind with these biomarker polypeptides. The kits can be employed in conjunction with the manual and automated screening methods of the invention. In various aspects, the kits can include instructions for use, and reagents and materials for measuring levels of the biomarker polypeptides e.g., in immunoassays, such as enzyme linked immunosorbent assays (ELISAs); Western blotting; direct or indirect immunofluorescence, immunohistochemistry, and the like.

The present invention further encompasses cell culture systems for the identification of polypeptides, in addition to the specified biomarker polypeptides, whose levels (e.g., extracellular, intracellular, or cell lysate levels) correlate with increased risk of developing HIV-1 protease inhibitor-dependent metabolic abnormalities upon the administration of a HIV-1 protease inhibitor. In specific aspects of the invention, such systems can comprise resistin expressing cell lines, which can be incubated in the presence or absence of one or more drugs, compounds, or other therapeutic agents. The biomarker polypeptides identified from these systems can be useful for identifying test substances (or combinations of test substances) that may directly or indirectly increase the risk of a patient developing HIV-1 protease inhibitor-dependent metabolic abnormalities in response to the administration of HIV-1 protease inhibitor compounds or combinations of such compounds, and thus to prevent or diminish the likelihood of a patient developing HIV-1 protease inhibitor-dependent metabolic abnormalities by either decreasing the level of the administered HIV-1 protease inhibitor compounds or combinations of such compounds, or by changing the HIV-1 protease inhibitor combination administered.

The present invention encompasses methods of measuring the levels of polypeptides (e.g., extracellular polypeptides in the media) using mass spectrometry data to determine the number of peptide "hits" for each polypeptide, and comparing the results obtained in the presence and absence of a test substance.

Also encompassed by the invention are nucleic acids encoding the disclosed resistin biomarker polypeptide (SEQ ID NO:12), and fragments, variants, and derivatives thereof, as well as screening assays, kits, microarrays, and cell culture systems employing these nucleic acids. In one aspect of the invention, screening assays (e.g., RT-PCR or in situ assays) that measure levels of one or more biomarker nucleic acids are used to predict which compound are likely to increase the risk of a patient developing HIV-1 protease inhibitor-dependent metabolic abnormalities in response to the administration of HIV-1 protease inhibitor compounds or combinations of such compounds, and thus to prevent or diminish the likelihood of a patient developing HIV-1 protease inhibitor-dependent metabolic abnormalities by either decreasing the level of the administered HIV-1 protease inhibitor compounds or combinations of such compounds, or by changing the HIV-1 protease inhibitor combination administered. Elevated levels of one or more biomarker nucleic acids in the presence of the test substance(s) can be used to predict which patients have an increased risk of developing HIV-1 protease inhibitor-dependent metabolic abnormalities in response to the administration of HIV-1 protease inhibitor compounds or combinations of such compounds, and thus to identify those patients that require monitoring more closely if an increased dosage of a HIV-1 protease inhibitor is contemplated in order to avoid the potential of increasing the likelihood of developing HIV-1 protease inhibitor-dependent metabolic abnormalities. Alternatively, low levels of one or more biomarker nucleic acids in the presence of the test substance(s) can be used to predict which patients have a decreased risk of developing HIV-1 protease inhibitor-dependent metabolic abnormalities in response to the administration of HIV-1 protease inhibitor compounds or combinations of such compounds, and thus identify which patients may be administered a correspondingly higher amount of a HIV-1 protease inhibitor without increasing the likelihood of developing HIV-1 protease inhibitor-dependent metabolic abnormalities.

The present invention also encompasses a method of predicting the risk that compound may increase the risk of a patient developing HIV-1 protease inhibitor-dependent metabolic abnormalities of a test substance comprising the steps of: a) incubating a resistin expressing cell in the presence and absence of a test substance; and b) comparing levels of at least one biomarker polypeptide, in the presence and absence of said test substance; wherein an elevated level of said biomarker polypeptide(s) in the presence of the test substance indicates that the substance is predicted to increase the risk of a patient developing HIV-1 protease inhibitor-dependent metabolic abnormalities in response to the administration of HIV-1 protease inhibitor compounds or combinations of such compounds, and wherein the level of said biomarker polypeptide(s) is measured using single or multi dimensional high performance liquid chromatography coupled to tandem mass spectrometry wherein the number of peptide hits from each protein identification are used to determine the abundance of said biomarker polypeptide(s) in the presence and absence of said test substance.

Publications and other materials setting forth such the proteomics methodologies include the following: McDonald W H, Yates J R 3rd., 2002, Shotgun proteomics and biomarker discovery, *Dis. Markers*. 18(2):99-105; Link A J, 2002, Multidimensional peptide separations in proteomics, *Trends Biotechnol*. Dec; 20(12 Suppl):S8-13. Additional publications outlining the application of such proteomic methods is set forth in the following: J. Gao et al, "Identification of In Vitro Protein Biomarkers of Idiosyncratic Liver Toxicity," Toxicology In Vitro, 18(4), 533-541 (2004); J. Gao et al, "Changes in the Protein Expression of Yeast as a Function of Carbon Source," Journal of Proteome Research, 2(6), 643-649 (2003); J. X. Pang et al, "Biomarker Discovery in Urine by Proteomics," Journal of Proteome Research, 1(2), 161-169 (2002). All of these publications are incorporated by reference herein in their entirety.

Polynucleotides and Polypeptides of the Invention

Features of Gene No:1

The present invention relates to isolated nucleic acid molecules comprising, or alternatively consisting of, all or a portion of one or more alleles of SNP1 of the human resistin gene, as provided in FIGS. 3A-B (SEQ ID NO:1) comprising at least one polymorphic locus. The allele described for SNP1 in FIGS. 3A-B (SEQ ID NO:1) represents the reference allele for this SNP and is exemplified by a "C" at nucleotide position 1398. Fragments of this polynucleotide are at least about 10, at least about 20, at least about 40, or at least about 100, contiguous nucleotides and comprise one or more reference alleles at the nucleotide position(s) provided in FIGS. 3A-B (SEQ ID NO:1).

In one embodiment, the invention relates to a method for predicting the likelihood that an individual will have a disorder, particularly HIV-1 protease inhibitor-dependent metabolic abnormalities, or be susceptible to developing HIV-1 protease inhibitor-dependent metabolic abnormalities upon the administration of a pharmaceutically acceptable amount of an HIV-1 protease inhibitor, comprising the step of identifying the nucleotide present at nucleotide position 1398 of SEQ ID NO:1, from a DNA sample to be assessed, or the corresponding nucleotide at this position if only a fragment of the sequence provided as SEQ ID NO:1 is assessed. The presence of the reference allele at said position indicates that the individual from whom said DNA sample or fragment was obtained has a decreased likelihood of developing HIV-1 protease inhibitor-dependent metabolic abnormalities upon the administration of a pharmaceutically acceptable amount of a HIV-1 protease inhibitor than an individual having the variable allele(s) at said position(s); or an decreased likelihood of developing more severe HIV-1 protease inhibitor-dependent metabolic abnormalities upon administration of the same.

Importantly, the presence of the reference allele at said position in a nucleic acid sample provided by an individual, indicates that said individual may be administered a correspondingly higher amount of a HIV-1 protease inhibitor without increasing the likelihood of developing HIV-1 protease inhibitor-dependent metabolic abnormalities relative to another individual having the variant allele(s) at said position. Therefore, such individuals may have the level of administered HIV-1 protease inhibitor "titrated-up" or maintained at the normal level without increasing the risk, or at least having a decreased risk, of a patient developing HIV-1 protease inhibitor-dependent metabolic abnormalities.

Representative disorders which may be detected, diagnosed, identified, treated, prevented, and/or ameliorated by the SNPs and methods of the present invention include, the following, non-limiting diseases and disorders: HIV-1 protease inhibitor-dependent metabolic abnormalities, susceptibility to developing HIV-1 protease inhibitor-dependent metabolic abnormalities upon the administration of a pharmaceutically acceptable amount of an HIV-1 protease inhibitor, susceptibility to developing HIV-1 protease inhibitor-dependent metabolic abnormalities upon the administration of an increased level of a HIV-1 protease inhibitor, adverse reactions associated with HIV-1 protease inhibitor, disorders associated with aberrant resistin expression, disorders associated with aberrant resistin regulation, disorders associated with aberrant resistin activity, disorders associated with aberrant regulation of resistin by cathepsin, disorders associated with aberrant regulation of resistin by cathepsin D, disorders associated with aberrant regulation of resistin by cathepsin E, disorders associated with elevated resistin plasma/serum levels, HAART-associated lipodystrophy, fat atrophy, fat hypertrophy, dyslipidemia, insulin resistance, cardiovascular disorders, myocardial infarction, stroke, atherosclerosis, peripheral lipoatrophy, central fat accumulation, hepatic steatosis, lipodystrophy syndrome, lipodystrophy-lie syndromes, hyperglycemia, decreased HDL levels, elevated levels of VLDL, hypertriglyceridemia, hypercholesterolemia, and hyperlipidemia.

Features of Gene No:2

The present invention relates to isolated nucleic acid molecules comprising, or alternatively consisting of, all or a portion of one or more alleles of SNP2 of the human resistin gene, as provided in FIGS. 4A-B (SEQ ID NO:2) comprising at least one polymorphic locus. The allele described for SNP2 in FIGS. 4A-B (SEQ ID NO:2) represents the variable allele for this SNP and is exemplified by an "T" at nucleotide position 1398. Fragments of this polynucleotide are at least about 10, at least about 20, at least about 40, at least about 100, contiguous nucleotides and comprise one or more variable alleles at the nucleotide position(s) provided in FIGS. 4A-B (SEQ ID NO:2).

In one embodiment, the invention relates to a method for predicting the likelihood that an individual will have a disorder, particularly HIV-1 protease inhibitor-dependent metabolic abnormalities, or be susceptible to developing HIV-1 protease inhibitor-dependent metabolic abnormalities upon the administration of a pharmaceutically acceptable amount of a HIV-1 protease inhibitor, comprising the step of identifying the nucleotide present at nucleotide position 1398 of SEQ ID NO:2, from a DNA sample to be assessed, or the corresponding nucleotide at this position if only a fragment of the sequence provided as SEQ ID NO:2 is assessed. The presence of the variable allele at said position indicates that the individual from whom said DNA sample or fragment was obtained has an increased likelihood of developing HIV-1 protease inhibitor-dependent metabolic abnormalities upon the administration of a pharmaceutically acceptable amount of a HIV-1 protease inhibitor, compared to an individual having the reference allele(s) at said position(s); or at least an increased likelihood of developing more severe HIV-1 protease inhibitor-dependent metabolic abnormalities upon administration of the same.

Representative disorders which may be detected, diagnosed, identified, treated, prevented, and/or ameliorated by the SNPs and methods of the present invention include, the following, non-limiting diseases and disorders: HIV-1 protease inhibitor-dependent metabolic abnormalities, susceptibility to developing HIV-1 protease inhibitor-dependent metabolic abnormalities upon the administration of a pharmaceutically acceptable amount of an HIV-1 protease inhibitor, susceptibility to developing HIV-1 protease inhibitor-dependent metabolic abnormalities upon the administration of an increased level of a HIV-1 protease inhibitor, adverse reactions associated with HIV-1 protease inhibitor, disorders associated with aberrant resistin expression, disorders associated with aberrant resistin regulation, disorders associated with aberrant resistin activity, disorders associated with aberrant regulation of resistin by cathepsin, disorders associated with aberrant regulation of resistin by cathepsin D, disorders associated with aberrant regulation of resistin by cathepsin E, disorders associated with elevated resistin plasma/serum levels, HAART-associated lipodystrophy, fat atrophy, fat hypertrophy, dyslipidemia, insulin resistance, cardiovascular disorders, myocardial infarction, stroke, atherosclerosis, peripheral lipoatrophy, central fat accumulation, hepatic steatosis, lipodystrophy syndrome, lipodystrophy-lie syndromes, hyperglycemia, decreased HDL levels, elevated levels of VLDL, hypertriglyceridemia, hypercholesterolemia, and hyperlipidemia.

TABLE I

| Polynucleotide No. | CDNA CloneID | Allele | Polymorphic Locus Number | Nucleotide Position of Polymorphic Locus | Nucleotide at Polymorphic Locus | SEQ ID NO: |
|---|---|---|---|---|---|---|
| 1 | Human Resistin Gene - SNP1 | Reference | 1 | 1398 | C | 1 |
| 2 | Human Resistin Gene - SNP1 | Variable | 1 | 1398 | T | 2 |

Importantly, the presence of the variable allele at said position in a DNA sample provided by an individual indicates that said individual should be monitored more closely if an increased dosage of a HIV-1 protease inhibitor is contemplated in order to avoid the potential of increasing the likelihood of developing HIV-1 protease inhibitor-dependent metabolic abnormalities relative to another individual having the variant allele(s) at said position. In addition, the presence of the variable allele at said position in a DNA sample indicates a lower dose of HIV-1 protease inhibitor may be warranted or that it may be warranted to administer to the patient a different HIV-1 protease inhibitor that does not have as much of a likelihood of causing HIV-1 protease inhibitor-dependent metabolic abnormalities. Specifically, a patient harboring the variable allele, either heterozygously or homozygously, should be administered atazanavir, a protease inhibitor less likely to cause metabolic abnormalities (Jemsek, J. G. et al., Clin Infect Dis. 42:273-80 (2006)), or administered one or more PPARγ agonists, such as for example, rosiglitazone and/or pioglitazone, which are known to inhibit expression of resistin (Steppan, C. M. et al., Nature 409:307-12 (2001), alone or in combination with HAART.

Alternatively, the presence of the variable allele at said position in a DNA sample provided by an individual indicates that the patient may benefit from hypertriglyceridemia therapy which may include administration of bezafibrate either alone or in combination with an HIV-1 protease inhibitor (Ericsson, C G, J. Eur Heart, 19(Supplement A):A36-A39 (1998).

The present invention provides a polynucleotide comprising, or alternatively consisting of, the sequence identified as SEQ ID NO:1 and/or 2; or a fragment containing the polymorphic allele, wherein said fragment comprises at least 10 contiguous nucleotides of SEQ ID NO:1 and/or 2.

Preferably, the present invention is directed to a polynucleotide comprising, or alternatively consisting of, the sequence identified as SEQ ID NO:1 and/or 2, that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1 and/or 2.

The invention encompasses the application of PCR methodology to the polynucleotide sequences of the present invention, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide Variants

The present invention also encompasses variants (e.g., allelic variants, orthologs, etc.) of the polynucleotide sequence disclosed herein in SEQ ID NO:1 and/or 2, and the complementary strand thereto.

The present invention also encompasses variants of the polypeptide sequence, and/or fragments therein, disclosed in SEQ ID NO:12, a polypeptide encoded by the polynucleotide sequence in SEQ ID NO:1 and/or 2.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), or (d), above. Polynucleotides which hybridize to the complement of these nucleic acid molecules under stringent hybridization conditions or alternatively, under lower stringency conditions, are also encompassed by the invention, as are polypeptides encoded by these polypeptides.

Polynucleotide Fragments

The present invention is directed to polynucleotide fragments of the polynucleotides of the invention, and polynucleotide sequences that hybridize thereto.

In the present invention, a "polynucleotide fragment" refers to a short polynucleotide having a nucleic acid sequence which: is a portion of that shown in SEQ ID NO:1 and/or 2 or the complementary strand thereto, or is a portion of a polynucleotide sequence encoding the polypeptide of SEQ ID NO:12. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length, and comprise at least one polymorphic locus. A fragment "at least 20 nt in length," for example, is intended to include 20 or more contiguous bases from the cDNA sequence shown in SEQ ID NO:1 and/or 2. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, isolated fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:1 and/or 2, or the complementary strand thereto. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

Kits

The invention further provides kits comprising at least one agent for identifying which alleleic form of the SNPs identified herein is present in a sample. For example, suitable kits can comprise at least one antibody specific for a particular protein or peptide encoded by one alleleic form of the gene, or allele-specific oligonucleotide as described herein. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least 1, 10, 100 or all of the polymorphisms shown in Table I. Optional additional components of the kit include, for example, reagents, buffers, restriction enzymes, reverse-transcriptase or polymerase, the substrate nucleoside triphosphates, means used to label (for example, an avidin-enzyme conjugate and enzyme substrate and chromogen if the label is biotin, fluophores, and others as described herein), and the appropriate buffers for reverse transcription, PCR, or hybridization reactions. Usually, the kit also contains instructions for carrying out the methods.

The present invention provides kits that can be used in the methods described herein. In one embodiment, a kit comprises a single primer or probe of the invention comprising a means to detect at least one polymorphic locus, said means preferably comprises a purified primer or probe, in one or more containers. Such a primer or probe may further comprise a detectable label such as a fluorescent compound, an enzymatic substrate, a radioactive compound, a luminescent compound, a fluorophore, and/or a fluorophore linked to a terminator contained therein. Such a kit may further comprise reagents required to enable adequate hybridization of said single primer or probe to a DNA test sample, such that under suitable conditions, the primer or probe is capable of binding to said DNA test sample and signaling whether the variant or reference allele at the polymorphic locus is present in said DNA test sample.

In one example, the kit comprises a means method for detecting the presence of a polymorphic locus comprising one specific allele of at least one polynucleotide in a DNA test sample which serves as a template nucleic acid comprising: (a) forming an oligonucleotide bound to the polymorphic locus wherein the oligonucleotide comprises a fluorophore linked to a terminator contained therein; and (b) detecting fluorescence polarization of the fluorophore of the fluorescently-labeled oligonucleotide, wherein the oligonucleotide is formed from a primer bound to said DNA sample immediately 3' to the polymorphic locus and a terminator covalently linked to a fluorophore, and wherein said terminator-linked fluorophore binds to the polymorphic locus and reacts with the primer to produce an extended primer which is said fluorescently labeled oligonucleotide, wherein an increase in fluorescence polarization indicates the presence of the specific allele at the polymorphic locus, thereby detecting the presence of the specific allele at the polymorphic locus by said increase in fluorescence polarization.

The kit of the present invention may comprise the following non-limiting examples of fluorophores linked to a primer or probe of the present invention: 5-carboxyfluorescein (FAM-ddNTPs); 6-carboxy-X-rhodamine (ROX-ddNTPs); N,N,N',N'-tetramethyl-6-carboxyrhodamine (TMR-ddNTPs); and BODIPY-Texas Red (BTR-ddNTPs).

The present invention is also directed towards a kit comprising a solid support to which oligonucleotides comprising at least 10 contiguous nucleotides of SEQ ID NO:1, 2, 3, 4, 5, 6, or 7, wherein said oligonucleotide further comprises at least one polymorphic locus of SEQ ID NO:1, 2, 3, 4, 5, 6, or 7, are affixed. In such an embodiment, detection of a polynucleotide within a sample comprising the same or similar sequence to said oligonucleotide can be detected by hybridization.

The solid surface reagent in the above assay is prepared by known techniques for attaching protein material to solid support material, such as polymeric beads, dip sticks, 96-well plate or filter material. These attachment methods generally include non-specific adsorption of the oligonucleotide to the support or covalent attachment of the oligonucleotide to a chemically reactive group on the solid support. Alternatively, streptavidin coated plates can be used in conjunction with biotinylated oligonucleotide(s).

Thus, the invention provides an assay system or kit for carrying out this diagnostic method. The kit generally includes a support with surface-bound oligonucleotides, and a reporter for detecting hybridization of said oligonucleotide to a test polynucleotide.

Methods of Use of the Allelic Polynucleotides of the Present Invention

The determination of the polymorphic form(s) present in an individual at one or more polymorphic sites defined herein can be used in a number of methods.

In preferred embodiments, the polynucleotides and polypeptides of the present invention, including allelic and variant forms thereof, have uses which include, but are not limited to diagnosing individuals to identify whether a given individual has increased susceptibility or risk for developing HIV-1 protease inhibitor-dependent metabolic abnormalities disorder using the genotype assays of the present invention. In addition, the polynucleotides and polypeptides of the present invention, including allelic and variant forms thereof, have uses which include, but are not limited to, diagnosing individuals to identify whether a given individual, upon administration of an increased dose of a HIV-1 protease inhibitor, has increased susceptibility or risk for developing HIV-1 protease inhibitor-dependent metabolic abnormalities disorder using the genotype assays of the present invention.

Wherever the term "atazanavir" is used herein, it is understood (unless otherwise indicated) that the compound "atazanavir" is intended as well as all pharmaceutically acceptable salts thereof. Use of the term encompasses (unless otherwise indicated) solvates (including hydrates), crystal structures (including polymorphic forms of such structures) and salts of the compound. Pharmaceutical compositions of atazanavir include all pharmaceutically acceptable compositions comprising atazanavir and one or more diluents, vehicles and/or excipients. Atazanavir is commercially available as a prescription medicine from Bristol-Myers Squibb Company, New York, under the tradename REYATAZ® (atazanavir sulfate) for the treatment of HIV. Approved in 2003 by the U.S. Food and Drug Administration, REYATAZ® (atazanavir sulfate) is currently available in the form of 100 milligram ("mg"), 150 mg, 200 mg, and 300 mg capsules.

U.S. Pat. No. 5,849,911 to Fässler et al. discloses a series of azapeptide HIV protease inhibitors (which includes atazanavir) which have the structure

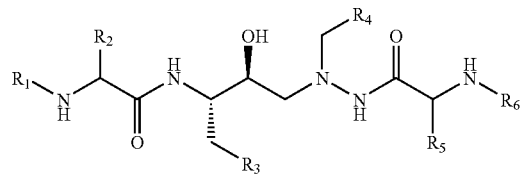

wherein
$R_1$ is lower alkoxycarbonyl,
$R_2$ is secondary or tertiary lower alkyl or lower alkylthio-lower alkyl,
$R_3$ is phenyl that is unsubstituted or substituted by one or more lower alkoxy radicals, or $C_4$-$C_8$ cycloalkyl,
$R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl (—SO—) and sulfonyl (—$SO_2$—) and is unsubstituted or substituted by lower alkyl or by phenyl-lower alkyl,
$R_5$, independently of $R_2$, has one of the meanings mentioned for $R_2$, and
$R_6$, independently of $R_1$, is lower alkoxycarbonyl, or a salt thereof, provided that at least one salt-forming group is present which includes various pharmaceutically acceptable acid addition salts thereof.

U.S. Pat. No. 6,087,383 to Singh et al. discloses the bisulfate salt of the azapeptide HIV protease inhibitor known as atazanavir which has the structure

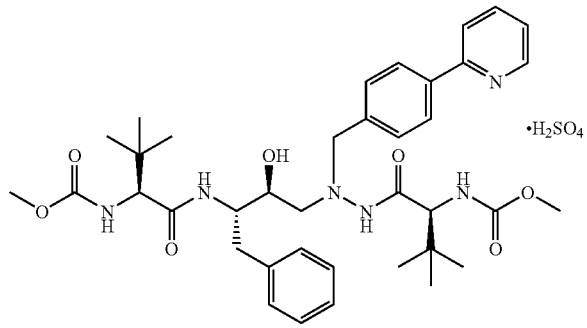

(referred to herein as "atazanavir bisulfate" or "atazanavir sulfate").

U.S. Patent Publication No. US20050256202A1, published Nov. 17, 2005, discloses processes for preparing the HIV protease inhibitor atazanavir bisulfate and novel forms thereof.

The typical dose of atazanavir to be administered to patients, for example human beings of approximately 70 kilograms ("kg") body weight, is from about 3 miligrams ("mg") to about 1.5 grams ("g"), preferably from about 10 mg to about 1.25 g, for example from about 50 mg to about 600 mg per person per day, divided preferably into 1 to 4 single doses which may, for example, be of the same size. Usually, children receive half of the adult dose.

Ritonavir is typically administered in combination with atazanavir sulfate as another agent having anti-HIV activity. When given as a protease inhibitor booster, the dosing typically ranges from 100-400 mg twice daily or, if used as a part of a once-daily regimen, 100-200 mg once-daily. Ritonavir is commercially available as a prescription medicine from Abbott Laboratories. Abbott Park, Ill., under the tradename Norvir® (ritonavir) for the treatment of HIV.

In preferred embodiments, the polynucleotides and polypeptides of the present invention, including allelic and variant forms thereof, have uses which include, but are not limited to diagnosing individuals to identify whether a given individual is at a higher risk of developing HIV-1 protease inhibitor-dependent metabolic abnormalities. An acceptable higher level of a pharmaceutically acceptable dose of a HIV-1 protease inhibitor for a patient identified as being at low risk of developing HIV-1 protease inhibitor-dependent metabolic abnormalities may be 5%, 10%, 15%, 20%, 25%, 30%, 35%, 40%, 45%, 50%, 55%, 60%, 65%, 75%, 80%, 85%, 90%, or 95% higher than the prescribed or typical dose, as may be the case.

In another preferred embodiment, the polynucleotides and polypeptides of the present invention, including allelic and variant forms thereof, have uses which include, but are not limited to diagnosing individuals to identify whether a given individual should be administered a correspondingly higher dose of a HIV-1 protease inhibitor in order to ameliorate an individuals susceptibility or risk for developing HIV-1 protease inhibitor-dependent metabolic abnormalities disorder using the genotype assays of the present invention.

In preferred embodiments, the polynucleotides and polypeptides of the present invention, including allelic and variant forms thereof, have uses which include, but are not limited to use in methods of screening to identify compounds, particularly HIV-1 protease inhibitor compounds, that have a lower risk of inducing HIV-1 protease inhibitor-dependent metabolic abnormalities or related disorder in a patient. Such identified compounds would be expected to retain all the benefits of a HIV-1 protease inhibitor but would have diminished ability of inducing increased resistin expression and/or function, or alternatively, capable of increasing resistin expression and/or function to a lesser extent than a reference compound known to be capable of inducing HIV-1 protease inhibitor-dependent metabolic abnormalities. Such compounds would be expected to be less likely to result in the development of HIV-1 protease inhibitor-dependent metabolic abnormalities.

In another embodiment, the polynucleotides and polypeptides of the present invention, including allelic and variant forms thereof, either alone, or in combination with other polymorphic polynucleotides (haplotypes) are useful as genetic markers for predicting an individuals suspectability to develop HIV-1 protease inhibitor-dependent metabolic abnormalities, and particularly to predicting an individuals suspectability to develop HIV-1 protease inhibitor-dependent metabolic abnormalities upon the administration of an increased dose of a HIV-1 protease inhibitor.

Additionally, the polynucleotides and polypeptides of the present invention, including allelic and/or variant forms thereof, are useful for creating additional antagonists directed against these polynucleotides and polypeptides, which include, but are not limited to the design of antisense RNA, ribozymes, PNAs, recombinant zinc finger proteins (Wolfe, S A., Ramm, E I., Pabo, C O, Structure, Fold, Des., 8 (7):739-50, (2000); Kang, J S., Kim, J S, J. Biol, Chem., 275 (12): 8742-8, (2000); Wang, B S., Pabo, C O, Proc. Natl. Acad. Sci. USA, 96 (17):9568-73, (1999); McColl, D J., Honchell, C D., Frankel, A D, Proc. Natl. Acad. Sci. USA, 96 (17):9521-6, (1999); Segal, D J., Dreier, B., Beerli, R R., Barbas, C F-3rd, Proc. Natl. Acad. Sci. USA, 96 (6):2758-63, (1999); Wolfe, S A., Greisman, H A., Ramm, E I., Pabo, C O, J. Mol, Biol., 285 (5):1917-34, (1999); Pomerantz, J L., Wolfe, S A., Pabo, C O, Biochemistry., 37 (4):965-70, (1998); Leon, O., Roth, M., Biol. Res. 33 (1):21-30 (2000); Berg, J M., Godwin, H A, Ann. Rev. Biophys. Biomol. Struct., 26:357-71 (1997)), in addition to other types of antagonists which are either described elsewhere herein, or known in the art.

The polynucleotides and polypeptides of the present invention, including allelic and/or variant forms thereof, are useful for identifying small molecule antagonists directed against the variant forms of these polynucleotides and polypeptides, preferably wherein such small molecules are useful as therapeutic and/or pharmaceutical compounds for the treatment, detection, prognosis, and/or prevention of the following, non-limiting diseases and/or disorders: HIV-1 protease inhibitor-dependent metabolic abnormalities, susceptibility to developing HIV-1 protease inhibitor-dependent metabolic abnormalities upon the administration of a pharmaceutically acceptable amount of an HIV-1 protease inhibitor, susceptibility to developing HIV-1 protease inhibitor-dependent metabolic abnormalities upon the administration of an increased level of a HIV-1 protease inhibitor, adverse reactions associated with HIV-1 protease inhibitor, disorders associated with aberrant resistin expression, disorders associated with aberrant resistin regulation, disorders associated with aberrant resistin activity, disorders associated with aberrant regulation of resistin by cathepsin, disorders associated with aberrant regulation of resistin by cathepsin D, disorders associated with aberrant regulation of resistin by cathepsin E, disorders associated with elevated resistin plasma/serum levels, HAART-associated lipodystrophy, fat atrophy, fat hypertrophy, dyslipidemia, insulin resistance, cardiovascular disorders, myocardial infarction, stroke, atherosclerosis, peripheral lipoatrophy, central fat accumulation, hepatic steatosis, lipodystrophy syndrome, lipodystrophy-lie syndromes, hyperglycemia, decreased HDL levels, elevated levels of VLDL, hypertriglyceridemia, hypercholesterolemia, and hyperlipidemia.

Additional disorders which may be detected, diagnosed, identified, treated, prevented, and/or ameliorated by the SNPs and methods of the present invention include, the following, non-limiting diseases and disorders: diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, and related diseases.

Additional uses of the polynucleotides and polypeptides of the present invention are provided herein.

Modified Polypeptides and Gene Sequences

The invention further provides variant forms of nucleic acids and corresponding proteins. The nucleic acids comprise one of the sequences described in Table I, in which the polymorphic position is occupied by one of the alternative bases for that position. Some nucleic acids encode full-length variant forms of proteins. Variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as E. coli, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like. As used herein, "gene product" includes mRNA, peptide and protein products.

The protein may be isolated by conventional means of protein biochemistry and purification to obtain a substantially pure product, i.e., 80, 95 or 99% free of cell component contaminants, as described in Jakoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990). If the protein is secreted, it can be isolated from the supernatant in which the host cell is grown. If not secreted, the protein can be isolated from a lysate of the host cells.

Haplotype Based Genetic Analysis

The invention further provides methods of applying the polynucleotides of the present invention to the elucidation of haplotypes. Such haplotypes may be associated with any one or more of the disease conditions referenced elsewhere herein.

A "haplotype" is defined as the pattern of a set of alleles of single nucleotide polymorphisms along a chromosome. For example, consider the case of three single nucleotide polymorphisms (SNP1, SNP2, and SNP3) in one chromosome region, of which SNP1 is an A/G polymorphism, SNP2 is a G/C polymorphism, and SNP3 is an A/C polymorphism. A and G are the alleles for the first, G and C for the second and A and C for the third SNP. Given two alleles for each SNP, there are three possible genotypes for individuals at each SNP. For example, for the first SNP, A/A, A/G and G/G are the possible genotypes for individuals. When an individual has a genotype for a SNP in which the alleles are not the same, for example A/G for the first SNP, then the individual is a heterozygote. When an individual has an A/G genotype at SNP1, G/C genotype at SNP2, and A/C genotype at SNP3, there are four possible combinations of haplotypes (A, B, C, and D) for this individual. The set of SNP genotypes of this individual alone would not provide sufficient information to resolve which combination of haplotypes this individual possesses. However, when this individual's parents' genotypes are available, haplotypes could then be assigned unambiguously. For example, if one parent had an A/A genotype at SNP1, a G/C genotype at SNP2, and an A/A genotype at SNP3, and the other parent had an A/G genotype at SNP1, C/C genotype at SNP2, and C/C genotype at SNP3, while the child was a heterozygote at all three SNPs, there is only one possible haplotype combination, assuming there was no crossing over in this region during meiosis.

When the genotype information of relatives is not available, haplotype assignment can be done using the long range-PCR method (Clark, A. G. Mol Biol Evol 7 (2): 111-22 (1990); Clark, A. G., K. M. Weiss, et al. Am J Hum Genet 63 (2): 595-612 (1998); Fullerton, S. M., A. G. Clark, et al., Am J Hum. Genet 67 (4): 881-900 (2000); Templeton, A. R., A. G. Clark, et al., Am J Hum Genet 66 (1): 69-83 (2000)). When the genotyping result of the SNPs of interest are available from general population samples, the most likely haplotypes can also be assigned using statistical methods (Excoffier, L. and M. Slatkin. Mol Biol Evol 12 (5): 921-7 (1995); Fallin, D. and N. J. Schork, Am J Hum Genet 67 (4): 947-59 (2000); Long, J. C., R. C. Williams, et al., Am J Hum Genet 56 (3): 799-810 (1995)).

Once an individual's haplotype in a certain chromosome region (i.e., locus) has been determined, it can be used as a tool for genetic association studies using different methods, which include, for example, haplotype relative risk analysis (Knapp, M., S. A. Seuchter, et al., Am J Hum Genet 52 (6): 1085-93 (1993); Li, T., M. Arranz, et al., Schizophr Res 32 (2): 87-92 (1998); Matise, T. C., Genet Epidemiol 12 (6): 641-5 (1995); Ott, J., Genet Epidemiol 6 (1): 127-30 (1989); Terwilliger, J. D. and J. Ott, Hum Hered 42 (6): 337-46 (1992)). Haplotype based genetic analysis, using a combination of SNPs, provides increased detection sensitivity, and hence statistical significance, for genetic associations of diseases, as compared to analyses using individual SNPs as markers. Multiple SNPs present in a single gene or a continuous chromosomal region are useful for such haplotype-based analyses.

Uses of the Polynucleotides

Each of the polynucleotides identified herein can be used in numerous ways as reagents. The following description should be considered exemplary and utilizes known techniques.

Increased or decreased expression of the gene in affected organisms as compared to unaffected organisms can be assessed using polynucleotides of the present invention. Any of these alterations, including altered expression, or the presence of at least one SNP of the present invention within the gene, can be used as a diagnostic or prognostic marker.

The invention provides a diagnostic method useful during diagnosis of a disorder, involving measuring the presence or expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

REFERENCES

1. Carr, A., HIV lipodystrophy: risk factors, pathogenesis, diagnosis and management. Aids, 2003. 17 Suppl 1: p. S141-8.

2. Grinspoon, S. and A. Carr, Cardiovascular risk and body-fat abnormalities in HIV-infected adults. N Engl J Med, 2005. 352(1): p. 48-62.

3. Steppan, C. M., et al., The hormone resistin links obesity to diabetes. Nature, 2001. 409(6818): p. 307-12.

4. Rajala, M. W., et al., Adipose-derived resistin and gut-derived resistin-like molecule-beta selectively impair insulin action on glucose production. J Clin Invest, 2003. 111(2): p. 225-30.

5. Banerjee, R. R., et al., Regulation of fasted blood glucose by resistin. Science, 2004. 303(5661): p. 1195-8.

6. Conneely, K. N., et al., Variation in the resistin gene is associated with obesity and insulin-related phenotypes in Finnish subjects. Diabetologia, 2004. 47(10):p. 1782-8.

7. Mattevi, V. S., V. M. Zembrzuski, and M. H. Hutz, A resistin gene polymorphism is associated with body mass index in women. Hum Genet, 2004. 115(3): p. 208-12.

8. Ochi, M., et al., The absence of evidence for major effects of the frequent SNP +299G>A in the resistin gene on susceptibility to insulin resistance syndrome associated with Japanese type 2 diabetes. Diabetes Res Clin Pract, 2003. 61(3): p. 191-8.

9. Kaser, S., et al., Resistin messenger-RNA expression is increased by proinflammatory cytokines in vitro. Biochem Biophys Res Commun, 2003. 309(2): p. 286-90.

10. Lehrke, M., et al., An inflammatory cascade leading to hyperresistinemia in humans. PLoS Med, 2004. 1(2): p. e45.

11. Dash, C., et al., Aspartic peptidase inhibitors: implications in drug development. Crit. Rev Biochem Mol Biol, 2003. 38(2): p. 89-119.

12. Ohtaka, H., et al., Thermodynamic rules for the design of high affinity HIV-1 protease inhibitors with adaptability to mutations and high selectivity towards unwanted targets. Int J Biochem Cell Biol, 2004. 36(9): p. 1787-99.

13. Patel, S. D., et al., Disulfide-dependent multimeric assembly of resistin family hormones. Science, 2004. 304 (5674): p. 1154-8.

14. Gray, W. R., Disulfide structures of highly bridged peptides: a new strategy for analysis. Protein Sci, 1993. 2(10): p. 1732-48.

15. Chou, K. C., et al., Predicting human immunodeficiency virus protease cleavage sites in proteins by a discriminant function method. Proteins, 1996. 24(1): p. 51-72.

16. Carr, A., HIV protease inhibitor-related lipodystrophy syndrome. Clin Infect Dis, 2000. 30 Suppl 2: p. S135-42.

EXAMPLES

Example 1

Method of Discovering Cathepsin D and Cathepsin E Proteolytic Degradation of Resistin As described elsewhere herein, a SNP was identified in the resistin gene, referred to herein as SNP1, that was determined to be associated with the incidence of lipodystrophy in patients administered HAART therapy. On account of the potential for HIV positive patients to have elevated plasma/serum levels of resistin, in conjunction with the fact that some aspartyl proteases may be inhibited by HIV-1 protease inhibitors, the inventors sought to determine whether either of the latter could serve as the basis for the observed association of resistin to lipodystrophy.

The protease assays were performed as follows:

HIV-1 Protease Inhibitors: HIV-1 protease inhibitors ritonavir and lopinovir were purified by reverse phase high-performance liquid chromatography from commercial pharmaceutical preparations. Atazanavir was synthesized by and provided in pure form from the Chemistry Division of Bristol-Myers Squibb Co. All compounds were dissolved in 100% DMSO (Sigma). The final concentration of DMSO was 0.2% in experiments that included a protease inhibitor.

Recombinant Proteins: Recombinant human and mouse resistin were obtained from Santa Cruz Biotech. Recombinant cathepsin D and cathepsin E were obtained from R&D Systems Inc. Recombinant HIV-1 protease was obtained from Protein One. Recombinant renin was obtained from Cayman Chemical and recombinant trypsin was from Promega.

Alkylation/Reduction of Cysteine Residues: Lyophilized resistin (24 micrograms) was resuspended in 50 ul of fresh UA buffer (8 M urea, 0.4 M ammonium bicarbonate) and 5 ul of 45 mM DTT. The mixture was then incubated at 50° C. for 15 min, followed by addition of 5 ul of 0.1 M iodoacetamide. The reaction was then incubated for an additional 15 min in the dark at room temperature, followed by the addition of 140 ul of H20.

Preparation of Proteases: Lyophilized cathepsin D (10 ug) was resuspended in 100 ul H20. Cathepsin D was activated prior to use by incubating at 20 ng/ul in CathD buffer (100 mM NaOAc, 200 mM NaCl, pH 4.7) for 30 min at 37° C. Lyophilized cathepsin E (10 ug) was resuspended in 100 ul of reconstitution buffer (25 mM MES, 0.15 M NaCl, pH 6.5). Cathepsin E was activated prior to use by incubating at 20 ng/ul in CathE buffer (100 mM NaOAc, 100 mM NaCl, pH 4.7) for 30 min at room temperature. Renin was diluted to 20 ng/ul in renin buffer (50 mM Tris-HCl, pH 8, 100 mM NaCl) prior to use. Lyophilized trypsin (20 ug) was resuspended in 500 ul reconstitution buffer provided by the manufacturer (Promega). Trypsin was activated prior to use by incubating for 15 min at 30° C. HIV-1 protease was used directly from the manufacturer.

Protease Digestion Experiments: In all protease digestion reactions, 1 ug of alkylated and reduced resistin was incubated with either 1 ug HIV-1 protease, 0.1 ug cathepsin D, 0.1 ug cathepsin E or 0.1 ug trypsin. HIV-1 protease digestion was performed in HIV-1 PR buffer (50 mM MES (pH 6), 100 mM NaCl). Trypsin digestion was performed in TE buffer (10 mM Tris (pH 8), 0.1 mM EDTA (pH 8)). The respective reaction buffers for cathepsin D, cathepsin E and renin are listed above under "Preparation of proteases". For experiments that contained HIV-1 protease inhibitors, varying concentrations of atazanavir, ritonavir or lopinovir were added to the protease digestion reactions. Control experiments that did not contain protease inhibitor contained additional 0.2% DMSO (vehicle control). All protease digestion experiments were incubated for 24 hr at 37° C. with the exception of experiments containing cathepsin E, which were incubated at room temperature. Reactions were quenched in LDS loading dye (Invitrogen) containing reducing agent (Invitrogen). Reactions were subsequently heated at 70° C. for 5 min prior analysis by SDS-PAGE.

SDS-PAGE Analysis: Cleavage products were resolved using 4-12% Bis-Tris NUPAGE® Gels (Invitrogen). Gels were run at 200 V for 20 min in MES buffer. Protein bands were visualized by staining with Gel Code reagent (Pierce).

Four aspartyl proteases, HIV-1 protease, cathepsin D, cathepsin E and renin were evaluated for their ability to cleave resistin (MW ca. 10.4 kDa) in vitro. As shown in FIG. 1, incubation with HIV-1 protease, cathepsin D and cathepsin E resulted in the appearance of a ca. 7 kDa resistin cleavage product. Additional cleavage products were not detectable by SDS-PAGE, suggesting that the remaining ca. 3.4 kDa fragment was further proteolyzed. Consistent with expectation, resistin was completely degraded by the non-specific protease, trypsin, but was refractory to cleavage by the highly specific protease, renin.

In addition, the protease inhibitors atazanavir and ritonavir were also evaluated for their ability to inhibit the proteolysis of resistin by cathepsin D and cathepsin E. As shown in FIG. 2, cleavage of resistin by cathepsin D and cathepsin E was not detectably inhibited by atazanavir, however, cleavage of resistin by cathepsin D and cathepsin E by ritonavir at 30 μM and 10 μM, respectively. Cathepsin D and cathepsin E were fully inhibited by ritonavir at 100 μM and 30 μM, respectively.

Ritonavir is known in the art to cause metabolic abnormalities, while atazanavir is not. The above results support the hypothesis that screening for HIV-1 protease inhibitor compound that lack the ability to inhibit cathepsin D and/or cathepsin E-dependent proteolysis of resistin would be desirable in order to identify compounds that have a decreased likelihood of causing metabolic abnormalities in patients.

Example 2

Method of Discovering the Single Nucleotide Polymorphisms (SNPs) of the Present Invention Elevated lipid levels, insulin resistance and changes in body fat, collectively known as lipodystrophy, are common in HIV infected individuals (Grinspoon, S. & Carr, A., N. Engl. J. Med. 352: 48-62 (2005)). Highly active anti-retroviral therapy (HAART) is one of the strongest predictors of lipodystrophy (Grinspoon, S. & Carr, A., N. Engl. J. Med. 352: 48-62 (2005)). With the reduction in mortality resulting from treatment with HAART, these metabolic side-effects are of concern as they are well-established risk factors for cardiovascular disease. The mechanistic basis of HAART-associated lipodystrophy is poorly understood, however.

Metabolic profiles of participants in a HAART-trial were clustered to identify a sub-group of patients who had a normal metabolic profile at baseline but developed significantly elevated plasma lipid levels and insulin resistance on HAART. 189 participants of a HAART trial (Dube, M. P. et al., AIDS 19: 1807-18 (2005)) who had metabolic measurements at baseline and up to 64 weeks of treatment were analyzed. All subjects gave written informed consent. The metabolic profile for each patient after 32 weeks of HAART comprised measurements of body mass index, total, LDL, HDL and non-HDL cholesterol, triglycerides, glucose and insulin resistance by homeostasis model adjustment (HOMA-IR). Individuals with similar metabolic profiles were grouped together, and this process was iteratively repeated until all individuals were clustered into groups. By using change in information content as a function of cluster number, the optimal number of clusters was determined, which in this case was two. Examination of mean values of metabolic traits led to labeling one cluster normal (N=142) and the other high-risk (N=47).

The 189 individuals in these two clusters were genotyped for 285 SNPs in 135 candidate genes. Genes were selected based on their likely involvement in regulating lipid and glucose metabolism, cytokines, drug metabolizing enzymes and transcription factors that regulate expression of these genes. Genes were also selected based upon those genes that had significantly perturbed expression patterns in cell-culture after exposure to protease inhibitors. Single nucleotide polymorphisms (SNPs) that were more likely to affect the activity (e.g. coding sequence changes) or expression (promoter or near splice-sites) of the gene were selected for further analysis.

Example 3

Method of Genotyping Each SNP of the Present Invention

Genomic DNA samples from patients enrolled in a HAART trial (Dube, M. P. et al., AIDS 19: 1807-18 (2005)) were genotyped for 285 SNPs identified in 135 candidate genes (see Example 1) and evaluated for association with HAART-dependent metabolic abnormalities.

All analyses were based on data collected at baseline and up to 64 weeks of treatment. DNA was extracted from frozen blood by a third-party.

Genotyping was performed using the 5' nuclease assay, essentially as described (Ranade K et al., Genome Research 11: 1262-1268 (2001); which is hereby incorporated by reference herein in its entirety), with the following modifications: six nanograms of genomic DNA were used in a 8 ul reaction. All PCR reactions were performed in an ABI 9700 machine and fluorescence was measured using an ABI 7900 machine.

Genotyping of the SNPs of the present invention was performed using sets of TAQMAN® probes (100 uM each) and primers (100 uM each) specific to each SNP. Each probe/primer set was manually designed using ABI Primer Express software (Applied Biosystems). Genomic samples were prepared as described herein. The following TAQMAN® probes and primers were utilized for one of the resistin SNPs. Genotyping primers for the other 284 SNPs have not been provided.

| SNP | TAQMAN® Forward Primer | TAQMAN® Reverse Primer | Reference TAQMAN® Probe | Variable TAQMAN® Probe |
|---|---|---|---|---|
| SNP1 | CCGGCTCCCTA AGTGAGGAC (SEQ ID NO:3) | GAGTCAGGTCT GTGCCAGGG (SEQ ID NO:4) | TCCCCAAGGGT CTCAGAGACCT CAC (SEQ ID NO:5) | TCCCCAAGGGT CTTAGAGACCT CACT (SEQ ID NO:6) |

** The allelic nucleotide in each probe sequence is shown in bold and underlined.

The genotype assay conditions are provided below.

| Components: | Final Concentration: |
|---|---|
| 2x PE Master Mix (#4318157) | 1X |
| 100 uM FAM labeled probe | 200 nmol |
| 100 uM VIC labeled probe | 200 nmol |
| Forward PCR primer | 600 nmol |
| Reverse PCR primer | 600 nmol |
| 6 ng template DNA | as required |
| ddH20 | volume to 8 ul |

TAQMAN® thermo-cycling was performed on Perkin Elmer PE 9700 machines using the following cycling conditions below:

1) 50 C for 2 minutes
2) 95 C for 10 seconds*
3) 94 C for 15 seconds
4) 62 C for 1 minute
5) 4 C hold

*Steps 2-4 were cycled 40 times

Analysis of genotypes was performed by using the Applied Biosystems ABI 7900 HT sequence detection system.

Example 4

Statistical Analysis of the Association Between HAART-Dependent Metabolic Abnormalities and the SNPs of the Present Invention The association between HAART-dependent metabolic abnormalities and the single nucleotide polymorphisms of the present invention were investigated by applying statistical analysis to the results of the genotyping assays described elsewhere herein. The central hypothesis of this analysis is that a predisposition to develop HIV-1 protease inhibitor-dependent metabolic abnormalities may be conferred by specific genomic factors. The analysis attempted to identify one or more of these factors, in genomic DNA samples from index cases and matched control subjects who were exposed to HAART in a clinical study (see Example 2).

SNPs of the present invention were examined for association with HIV-1 protease inhibitor-dependent metabolic abnormalities using 3 (genotypes)×2 (high risk and low risk cluster) contingency tables.

Methods

Sample: Investigators in the BMS clinical trials diagnosed HIV-1 protease inhibitor-dependent metabolic abnormalities in some subjects.

Measures: Single nucleotide polymorphisms (SNPs) in human resistin were genotyped on all subjects essentially as described in Example 2 herein. The SNPs that were genotyped likely represent a sample of the polymorphic variation in each gene and are not exhaustive with regard to coverage of the total genetic variation that may be present in each gene. The SNP for which a statistical association to HIV-1 protease inhibitor-dependent metabolic abnormalities was confirmed is provided as SNP1.

Statistical Analyses: All statistical analyses were done using SPSS® version 12 (Chicago, Ill., US).

Clustering: Traits measured after 32 weeks of HAART were standardized to have a mean of 0 and variance of 1 and then used in the clustering. For each individual a profile was made of body mass index, total, LDL, HDL and non-HDL cholesterol, triglyceride, glucose, and HOMA-IR. These profiles were clustered together using "two-step" clustering to identify sub-groups with more homogeneous metabolic profiles. In this clustering method, data are a first grouped into sub-clusters using agglomerative clustering and then cluster assignment is refined to determine the optimal number of clusters. The optimal number of clusters was determined in two steps. First, Bayesian information criterion was calculated for the specified number of clusters to obtain an initial estimate of cluster number. Second, this estimate was refined by finding the greatest change in distance between two clusters in each stage of hierarchical clustering The distance between two clusters was defined as the decrease in log-likelihood resulting from the two clusters being combined into a single cluster. Up to 20 clusters were permitted, but the algorithm repeatedly determined that a two cluster solution was optimal. To assess stability of the cluster solution, multiple runs (N=20) of clustering were performed on different days using randomly sorted data. All runs produced clusters identical to those described earlier. Differences in means between clusters for metabolic traits and body fat were evaluated using Kruskal-Wallis or repeated measures ANOVA.

Genetic association between SNPs and clusters was assessed using $\chi^2$ or Fisher's exact tests.

A C/T SNP thirty-nine base-pairs downstream of the second exon of the resistin gene was the most significantly associated with cluster membership (P=0.0003). The frequency of this SNP in the normal cluster was 0.16 and it was 0.33 in the high-risk cluster. C/T heterozygotes and T/T homozygotes were 2.7 (95% C.I. 1.3-5.3) and 19 (95% C.I. 2-183) times more likely to be classified in the high-risk cluster than wild-type (P=0.001).

The nucleotide sequence of the resistin gene containing the reference allele ("C") for SNP1 at nucleotide 1398 is provided in FIGS. 3A-B (SEQ ID NO:1); while the nucleotide sequence of the resistin gene containing the variable allele ("T") for SNP1 at nucleotide 1398 is provided in FIGS. 4A-B (SEQ ID NO:2).

Resistin was cloned as a hormone that links obesity and insulin resistance (Steppan, C. M. et al., Nature 409: 307-12 (2001). Increased resistin resulted in mice with abnormal glucose tolerance (Steppan, C. M. et al., Nature 409: 307-12 (2001). Conversely, resistin knockout mice had lower fasting blood glucose (Banerjee, R. et al., Science 203: 1195-98 (2004)). Consistent with the genetic association observed in this study, SNPs in resistin have been variably associated with metabolic traits captured by the clusters described above including body mass index, fat mass, insulin resistance and diabetes (Engert, J. C., et al., Diabetes 51: 1629-34 (2002); Engert, J. C., et al. Diabetes 51: 1629-34 (2002); Wang, H., et al., J. Clin. Endo. Metab. 87: 2520-24 (2002); Sentinelli, F. et al., Diabetes 51: 860-62 (2002); Coneely, K. N. et al., Diabetologia 47: 1782-88 (2004); and Osawa, H. et al., Am. J. Hum. Genet. 75: 678-86 (2004).

These results suggest that polymorphisms in the resistin gene contributes to differences in susceptibility to HIV-1 protease inhibitor-dependent metabolic abnormalities independent of other significant predictors such as age, sex and body mass index.

The utility, in general, of each of these significant SNP-HIV-1 protease inhibitor-dependent metabolic abnormalities event associations is that they suggest (1) such SNPs may be causally involved, alone or in combination with other SNPs in the respective gene regions with susceptibility to HIV-1 protease inhibitor-dependent metabolic abnormalities events resulting from exposure to a HIV-1 protease inhibitor; (2) such SNPs, if not directly causally involved, are reflective of an association because of linkage disequilibrium with one or more other SNPs that may be causally involved, alone or in combination with other SNPs in the respective gene regions with susceptibility to HIV-1 protease inhibitor-dependent metabolic abnormalities resulting from exposure to a HIV-1 protease inhibitor; (3) such SNPs may be useful in establishing haplotypes that may be used to narrow the search for and identify polymorphisms or combinations of polymorphisms that may be causally, alone or in combination with other SNPs in the respective gene regions with susceptibility to HIV-1 protease inhibitor-dependent metabolic abnormalities resulting from exposure to a HIV-1 protease inhibitor; and (4) such SNPs, if used to establish haplotypes that are identified as causally involved in such event susceptibility, may be used to predict which subjects are most likely to experience such events when exposed to a HIV-1 protease inhibitor-dependent metabolic abnormalities resulting from exposure to a HIV-1 protease inhibitor. The term "respective gene regions" shall be construed to refer to those regions of each gene which have been used to identify the SNPs of the present invention.

Example 5

Method of Isolating the Native Forms of the Human Resistin Gene

A number of methods have been described in the art that may be utilized in isolating the native forms of the human resistin gene. Specific methods are referenced below and are hereby incorporated by reference herein in their entireties. The artisan, skilled in the molecular biology arts, would be able to isolate the native form of human resistin based upon the methods and information contained, and/or referenced, therein.

1. Human Resistin (gi|NM_020415; SEQ ID NO:7; chr19:7638972-7641340 dbSNP ID rs3219177).
2. Adeghate, E., Cell. Mol. Life. Sci. 61 (19-20), 2485-2496 (2004).
3. Azuma, K., et al., Horm. Metab. Res. 36 (8), 564-570 (2004).
4. Cho, Y. M., et al., Diabetologia 47 (3), 559-565 (2004).

5. Motojima, K., J. Endocrinol. Invest. 26 (12), 1171-1173 (2003).
6. Seo, J. B., et al., Mol. Endocrinol. 17 (8), 1522-1533 (2003).
7. Smith, S. R., et al., Diabetes 52 (7), 1611-1618 (2003).
8. Banerjee, R. R. and Lazar, M. A., J. Mol. Med. 81 (4), 218-226 (2003).
9. Tan, M. S., et al., J. Clin. Endocrinol. Metab. 88 (3), 1258-1263 (2003).
10. Ma, X., et al., J. Clin. Endocrinol. Metab. 87 (9), 4407-4410 (2002).
11. Pizzuti, A., et al., J. Clin. Endocrinol. Metab. 87 (9), 4403-4406 (2002).
12. Wang, H., et al., J. Clin. Endocrinol. Metab. 87 (6), 2520-2524 (2002).
13. McTernan, P. G., et al., J. Clin. Endocrinol. Metab. 87 (5), 2407 (2002).
14. Steppan, C. M., et al., Proc. Natl. Acad. Sci. U.S.A. 98 (2), 502-506 (2001).
15. Holcomb, I. N., et al., EMBO J. 19 (15), 4046-4055 (2000).
16. Bennett, M. and Reed, R., Science 262 (5130), 105-108 (1993).

Methods of isolation for the human resistin gene of the present invention may also be found in reference to the references cited in the GENBANK® accession nos. for each gene provided herein which are hereby incorporated by reference herein.

Example 6

Method of Isolating the Polymorphic Forms of the Human Resistin Gene of the Present Invention Since the allelic genes of the present invention represent genes present within at least a subset of the human population, these genes may be isolated using the methods provided in Example 4 above. For example, the source DNA used to isolate the allelic gene may be obtained through a random sampling of the human population and repeated until the allelic form of the gene is obtained. Preferably, random samples of source DNA from the human population are screened using the SNPs and methods of the present invention to identify those sources that comprise the allelic form of the gene. Once identified, such a source may be used to isolate the allelic form of the gene(s). The invention encompasses the isolation of such allelic genes from both genomic and/or cDNA libraries created from such source(s).

In reference to the specific methods provided in Example 4 above, it is expected that isolating the polymorphic alleles of the human resistin gene would be within the skill of an artisan trained in the molecular biology arts. Nonetheless, a detailed exemplary method of isolating at least one of the resistin polymorphic alleles, in this case the variant form of SNP31 ("T" nucleotide at 1398 of SEQ ID NO:1) is provided. Briefly, First, the individuals with the "t" allele at the locus corresponding to nucleotide 1398 of SEQ ID NO:1 or 2 are identified by genotyping the genomic DNA samples using the method outlined in Example 2 herein. Other methods of genotyping may be employed, such as the FP-SBE method (Chen et al., Genome Res., 9(5):492-498 (1999)), or other methods described herein. DNA samples publicly available (e.g., from the Coriell Institute (Collingswood, N.J.) or from the clinical samples described herein may be used. Oligonucleotide primers that are used for this genotyping assay are provided in Example 2.

By analyzing genomic DNA samples, individuals with the C1398T form of the SNP1 variant may be identified. Once identified, clones comprising the genomic sequence may be obtained using methods well known in the art (see Sambrook, J., E. F. Fritsch, and T. Maniatis, 1989, Molecular Cloning: A Laboratory Manual, Cold Spring Harbor Laboratory Press, Cold Spring Harbor, N.Y.; and Current Protocols in Molecular Biology, 1995, F. M. Ausubel et al., eds., John Wiley and Sons, Inc., which are hereby incorporated by reference herein.).

If cDNA clones of the coding sequence of this allele of the gene are of interest, such clones may be obtained in accordance with the following steps. Next, Lymphoblastoid cell lines may be obtained from the Coriell Institute. These cells can be grown in RPMI-1640 medium with L-glutamine plus 10% FCS at 37 degrees. PolyA+ RNA are then isolated from these cells using OLIGOTEX® Direct Kit (Life Technologies).

First strand cDNA (complementary DNA) is produced using SUPERSCRIPT® Preamplification System for First Strand cDNA Synthesis (Life Technologies, Cat No 18089-011) using these polyA+ RNA as templates, as specified in the users manual which is hereby incorporated herein by reference in its entirety. Specific cDNA encoding the human resistin protein is amplified by polymerase chain reaction (PCR) using a forward primer which hybridizes to the 5'-UTR region, a reverse primer which hybridizes to the 3'-UTR region, and these first strand cDNA as templates (Sambrook, Fritsch et al. 1989). Alternatively, these primers may be designed using Primer3 program (Rozen S 2000). Restriction enzyme sites (example: SalI for the forward primer, and NotI for reverse primer) are added to the 5'-end of these primer sequences to facilitate cloning into expression vectors after PCR amplification. PCR amplification may be performed essentially as described in the owner's manual of the Expand Long Template PCR System (Roche Molecular Biochemicals) following manufacturer's standard protocol, which is hereby incorporated herein by reference in its entirety.

PCR amplification products are digested with restriction enzymes (such as SalI and NotI, for example) and ligated with expression vector DNA cut with the same set of restriction enzymes. pSPORT (Invitrogen) is one example of such an expression vector. After ligated DNA is introduced into E. coli cells (Sambrook, Fritsch et al. 1989), plasmid DNA is isolated from these bacterial cells. This plasmid DNA is sequenced to confirm the presence an intact (full-length) coding region of the human resistin protein with the variation, if the variation results in changes in the encoded amino acid sequence, using methods well known in the art and described elsewhere herein.

The skilled artisan would appreciate that the above method may be applied to isolating the other novel human resistin genes of the present invention through the simple substitution of applicable PCR and sequencing primers. Such primers may be selected from any one of the applicable primers provided in herein, or may be designed using the Primer3 program (Rozen S 2000) as described. Such primers may preferably comprise at least a portion of any one of the polynucleotide sequences of the present invention.

Example 7

Method of Engineering the Allelic Forms of the Human Resistin Gene of the Present Invention Aside from isolating the allelic genes of the present invention from DNA samples obtained from the human population, as described in Example 5 above, the invention also encompasses methods of engineering the allelic genes of the present invention through the application of site-directed mutagenesis to the isolated native forms of the genes. Such methodology could be applied to synthesize allelic forms of the genes comprising at least one, or more, of the encoding SNPs of the present invention (e.g., silent, missense)—preferably at least 1, 2, 3, or 4 encoding SNPs for each gene.

In reference to the specific methods provided in Example 5 above, it is expected that isolating the novel polymorphic resistin genes of the present invention would be within the skill of an artisan trained in the molecular biology arts. Nonetheless, a detailed exemplary method of engineering at least one of the resistin polymorphic alleles to comprise the encoding and/or non-coding polymorphic nucleic acid sequence, in this case the variant form (C1398T) of SNP1 (SEQ ID NO:2) is provided. Briefly, cDNA clones encoding the human resistin protein may be identified by homology searches with the BLASTN program (Altschul SF 1990) against the GENBANK® non-redundant nucleotide sequence database using the published human resistin cDNA sequence (GENBANK® Accession No.: NM_020415). Alternatively, the genomic sequence of the human resistin gene may be obtained as described herein. After obtaining these clones, they are sequenced to confirm the validity of the DNA sequences.

However, in the case of the variant form (C1398T) of SNP1, genomic clones would need to be obtained and may be identified by homology searches with the BLASTN program (Altschul SF 1990) against the GENBANK® non-redundant nucleotide sequence database using the published human resistin genomic sequence (GENBANK® Accession No.: AC008963.9, nucleotides chr19:7638972-7641340 dbSNP ID rs3219177). Alternatively, the genomic sequence of the human resistin gene may be obtained as described herein. After obtaining these clones, they are sequenced to confirm the validity of the DNA sequences.

Once these clones are confirmed to contain the intact wild type cDNA or genomic sequence of the human resistin coding and/or non-coding region, the C1398T polymorphism (mutation) may be introduced into the native sequence using PCR directed in vitro mutagenesis (Cormack, B., Directed Mutagenesis Using the Polymerase Chain Reaction. Current Protocols in Molecular Biology, John Wiley & Sons, Inc. Supplement 37: 8.5.1-8.5.10, (2000)). In this method, synthetic oligonucleotides are designed to incorporate a point mutation at one end of an amplified fragment. Following PCR, the amplified fragments are made blunt-ended by treatment with Klenow Fragment. These fragments are then ligated and subcloned into a vector to facilitate sequence analysis. This method consists of the following steps.

1. Subcloning of cDNA or genomic insert into a plasmid vector, or BAC sequence if the clone is a genomic sequence, containing multiple cloning sites and M13 flanking sequences, such as pUC19 (Sambrook, Fritsch et al. 1989), in the forward orientation. The skilled artisan would appreciate that other plasmids could be equally substituted, and may be desirable in certain circumstances.
2. Introduction of a mutation by PCR amplification of the genomic region downstream of the mutation site using a primer including the mutation. (FIG. 8.5.2 in Cormack 2000)). In the case of introducing the C1398T mutation into the human resistin genomic sequence, the following two primers may be used.

M13 reverse sequencing primer:

```
5'-AGCGGATAACAATTTCACACAGGA-3'.     (SEQ ID NO:12)
```

Mutation primer:

```
                                     (SEQ ID NO:10)
5'-GGCAAGCTCCCCAAGGGTCTTAGAGACCTCACTGATCCC-3'
```

Mutation primer contains the mutation (C1398T) at the 5' end (in bold and underlined) and a portion of its flanking sequence. M13 reverse sequencing primer hybridizes to the pUC19 vector. Subcloned cDNA or genomic clone comprising the human resistin cDNA or genomic sequence is used as a template (described in Step 1). A 100 ul PCR reaction mixture is prepared using 10 ng of the template DNA, 200 uM 4dNTPs, 1 uM primers, 0.25 U Taq DNA polymerase (PE), and standard Taq DNA polymerase buffer. Typical PCR cycling condition are as follows:

| 20-25 cycles: | 45 sec, 93 degrees |
| | 2 min, 50 degrees |
| | 2 min, 72 degrees |
| 1 cycle: | 10 min, 72 degrees |

After the final extension step of PCR, 5U Klenow Fragment is added and incubated for 15 min at 30 degrees. The PCR product is then digested with the restriction enzyme, EcoRI.

3. PCR amplification of the upstream region is then performed, using subcloned cDNA or genomic clone as a template (the product of Step 1). This PCR is done using the following two primers:

M13 forward sequencing primer:

```
5'-CGCCAGGGTTTTCCCAGTCACGAC-3'.     (SEQ ID NO:8)
```

Flanking primer:

```
                                     (SEQ ID NO:11)
5'-GGGATCAGTGAGGTCTCTAAGACCCTTGGGGAGCTTGCC-3'.
```

Flanking primer is complimentary to the upstream flanking sequence and mutation locus of the C1398T mutation (in bold and underlined). M13 forward sequencing primer hybridizes to the pUC19 vector. PCR conditions and Klenow treatments follow the same procedures as provided in Step 2, above. The PCR product is then digested with the restriction enzyme, HindIII.

4. Prepare the pUC19 vector for cloning the cDNA or genomic clone comprising the polymorphic locus. Digest pUC19 plasmid DNA with EcoRI and HindIII. The resulting digested vector fragment may then be purified using techniques well known in the art, such as gel purification, for example.
5. Combine the products from Step 2 (PCR product containing mutation), Step 3 (PCR product containing the upstream region), and Step 4 (digested vector), and ligate them together using standard blunt-end ligation conditions (Sambrook, Fritsch et al. 1989).
6. Transform the resulting recombinant plasmid from Step 5 into *E. coli* competent cells using methods known in the the art, such as, for example, the transformation methods described in Sambrook, Fritsch et al. 1989.

7. Analyze the amplified fragment portion of the plasmid DNA by DNA sequencing to confirm the point mutation, and absence of any other mutations introduced during PCR. The method of sequencing the insert DNA, including the primers utilized, are described herein or are otherwise known in the art.

Example 8

Alternative Methods of Genotyping Polymorphisms Encompassed by the Present Invention Preparation of Samples Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For example, if the target nucleic acid is a cytochrome P450, the liver is a suitable source.

Many of the methods described below require amplification of DNA from target samples. This can be accomplished by e.g., PCR. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, (1991); PCR (eds. McPherson et al., IRL Press, Oxford); and U.S. Pat. No. 4,683,202.

Other suitable amplification methods include the ligase chain reaction (LCR) (see Wu and Wallace, Genomics 4:560 (1989), Landegren et al., Science 241:1077 (1988), transcription amplification (Kwoh et al., Proc. Natl. Acad. Sci. USA 86, 1173 (1989), and self-sustained sequence replication (Guatelli et al., Proc. Nat. Acad. Sci. USA, 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Additional methods of amplification are known in the art or are described elsewhere herein.

Detection of Polymorphisms in Target DNA

There are two distinct types of analysis of target DNA for detecting polymorphisms. The first type of analysis, sometimes referred to as de novo characterization, is carried out to identify polymorphic sites not previously characterized (i.e., to identify new polymorphisms). This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus can be identified, and the frequencies of such alleles/haplotypes in the population can be determined. Additional allelic frequencies can be determined for subpopulations characterized by criteria such as geography, race, or gender. The de novo identification of polymorphisms of the invention is described in the Examples section.

The second type of analysis determines which form(s) of a characterized (known) polymorphism are present in individuals under test. Additional methods of analysis are known in the art or are described elsewhere herein.

Allele-Specific Probes

The design and use of allele-specific probes for analyzing polymorphisms is described by e.g., Saiki et al., Nature 324, 163-166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic locus aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Tiling Arrays

The polymorphisms can also be identified by hybridization to nucleic acid arrays, some examples of which are described in WO 95/11995. The same arrays or different arrays can be used for analysis of characterized polymorphisms. WO 95/11995 also describes sub arrays that are optimized for detection of a variant form of a precharacterized polymorphism. Such a sub array contains probes designed to be complementary to a second reference sequence, which is an allelic variant of the first reference sequence. The second group of probes is designed by the same principles as described, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to bases).

Allele-Specific Primers

An allele-specific primer hybridizes to a site on target DNA overlapping a polymorphism and only primes amplification of an allelic form to which the primer exhibits perfect complementarity. See Gibbs, Nucleic Acid Res. 17,2427-2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic locus and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing elongation from the primer (see, e.g., WO 93/22456).

Direct-Sequencing

The direct analysis of the sequence of polymorphisms of the present invention can be accomplished using either the dideoxy chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology. Principles and Applications for DNA Amplification, (W. H. Freeman and Co, New York, 1992), Chapter 7.

Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86,2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

Single Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., (PNAS 94:10756-61 (1997), uses a locus-specific oligonucleotide primer labeled on the 5' terminus with 5-carboxyfluorescein (F AM). This labeled primer is designed so that the 3' end is immediately adjacent to the polymorphic locus of interest. The labeled primer is hybridized to the locus, and single base extension of the labeled primer is performed with fluorescently-labeled dideoxyribonucleotides (ddNTPs) in dye-terminator sequencing fashion. An increase in fluorescence of the added ddNTP in response to excitation at the wavelength of the labeled primer is used to infer the identity of the added nucleotide.

Example 9

Additional Methods of Genotyping the SNPs of the Present Invention

The skilled artisan would acknowledge that there are a number of methods that may be employed for genotyping a SNP of the present invention, aside from the preferred methods described herein. The present invention encompasses the following non-limiting types of genotype assays: PCR-free genotyping methods, Single-step homogeneous methods, Homogeneous detection with fluorescence polarization, Pyrosequencing, "Tag" based DNA chip system, Bead-based methods, fluorescent dye chemistry, Mass spectrometry based genotyping assays, TAQMAN® genotype assays, Invader genotype assays, and microfluidic genotype assays, among others.

Specifically encompassed by the present invention are the following, non-limiting genotyping methods: Landegren, U., Nilsson, M. & Kwok, P. Genome Res 8, 769-776 (1998); Kwok, P., Pharmacogenomics 1, 95-100 (2000); Gut, I., Hum Mutat 17, 475-492 (2001); Whitcombe, D., Newton, C. & Little, S., Curr Opin Biotechnol 9, 602-608 (1998); Tillib, S. & Mirzabekov, A., Curr Opin Biotechnol 12, 53-58 (2001); Winzeler, E. et al., Science 281, 1194-1197 (1998); Lyamichev, V. et al., Nat Biotechnol 17, 292-296 (1999); Hall, J. et al., Proc Natl Acad Sci USA 97, 8272-8277 (2000); Mein, C. et al., Genome Res 10, 333-343 (2000); Ohnishi, Y. et al., J Hum Genet 46, 471-477 (2001); Nilsson, M. et al., Science 265, 2085-2088 (1994); Baner, J., Nilsson, M., Mendel-Hartvig, M. & Landegren, U., Nucleic Acids Res 26, 5073-5078 (1998); Baner, J. et al., Curr Opin Biotechnol 12, 11-15 (2001); Hatch, A., Sano, T., Misasi, J. & Smith, C., Genet Anal 15, 35-40 (1999); Lizardi, P. et al., Nat Genet 19, 225-232 (1998); Zhong, X., Lizardi, P., Huang, X., Bray-Ward, P. & Ward, D., Proc Natl Acad Sci USA 98, 3940-3945 (2001); Faruqi, F. et al. BMC Genomics 2, 4 (2001); Livak, K., Genet Anal 14, 143-149 (1999); Marras, S., Kramer, F. & Tyagi, S., Genet Anal 14, 151-156 (1999); Ranade, K. et al., Genome Res 11, 1262-1268 (2001); Myakishev, M., Khripin, Y., Hu, S. & Hamer, D., Genome Res 11, 163-169 (2001); Beaudet, L., Bedard, J., Breton, B., Mercuri, R. & Budarf, M., Genome Res 11, 600-608 (2001); Chen, X., Levine, L. & PY, K., Genome Res 9, 492-498 (1999); Gibson, N. et al., Clin Chem 43, 1336-1341 (1997); Latif, S., Bauer-Sardina, I., Ranade, K., Livak, K. & PY, K., Genome Res 11, 436-440 (2001); Hsu, T., Law, S., Duan, S., Neri, B. & Kwok, P., Clin Chem 47, 1373-1377 (2001); Alderborn, A., Kristofferson, A. & Hammerling, U., Genome Res 10, 1249-1258 (2000); Ronaghi, M., Uhlen, M. & Nyren, P., Science 281, 363, 365 (1998); Ronaghi, M., Genome Res 11, 3-11 (2001); Pease, A. et al., Proc Natl Acad Sci USA 91, 5022-5026 (1994); Southern, E., Maskos, U. & Elder, J., Genomics 13, 1008-1017 (1993); Wang, D. et al., Science 280, 1077-1082 (1998); Brown, P. & Botstein, D., Nat Genet 21, 33-37 (1999); Cargill, M. et al. Nat Genet 22, 231-238 (1999); Dong, S. et al., Genome Res 11, 1418-1424 (2001); Halushka, M. et al., Nat Genet 22, 239-247 (1999); Hacia, J., Nat Genet 21, 42-47 (1999); Lipshutz, R., Fodor, S., Gingeras, T. & Lockhart, D., Nat Genet 21, 20-24 (1999); Sapolsky, R. et al., Genet Anal 14, 187-192 (1999); Tsuchihashi, Z. & Brown, P., J Virol 68, 5863 (1994); Herschlag, D., J Biol Chem 270, 20871-20874 (1995); Head, S. et al., Nucleic Acids Res 25, 5065-5071 (1997); Nikiforov, T. et al., Nucleic Acids Res 22, 4167-4175 (1994); Syvanen, A. et al., Genomics 12, 590-595 (1992); Shumaker, J., Metspalu, A. & Caskey, C., Hum Mutat 7, 346-354 (1996); Lindroos, K., Liljedahl, U., Raitio, M. &

Syvanen, A., Nucleic Acids Res 29, E69-9 (2001); Lindblad-Toh, K. et al., Nat Genet 24, 381-386 (2000); Pastinen, T. et al., Genome Res 10, 1031-1042 (2000); Fan, J. et al., Genome Res 10, 853-860 (2000); Hirschhorn, J. et al., Proc Natl Acad Sci USA 97, 12164-12169 (2000); Bouchie, A., Nat Biotechnol 19, 704 (2001); Hensel, M. et al., Science 269, 400-403 (1995); Shoemaker, D., Lashkari, D., Morris, D., Mittmann, M. & Davis, R. Nat Genet 14, 450-456 (1996); Gerry, N. et al., J Mol Biol 292, 251-262 (1999); Ladner, D. et al., Lab Invest 81, 1079-1086 (2001); Iannone, M. et al. Cytometry 39, 131-140 (2000); Fulton, R., McDade, R., Smith, P., Kienker, L. & Kettman, J. J., Clin Chem 43, 1749-1756 (1997); Armstrong, B., Stewart, M. & Mazumder, A., Cytometry 40, 102-108 (2000); Cai, H. et al., Genomics 69, 395 (2000); Chen, J. et al., Genome Res 10, 549-557 (2000); Ye, F. et al. Hum Mutat 17, 305-316 (2001); Michael, K., Taylor, L., Schultz, S. & Walt, D., Anal Chem 70, 1242-1248 (1998); Steemers, F., Ferguson, J. & Walt, D., Nat Biotechnol 18, 91-94 (2000); Chan, W. & Nie, S., Science 281, 2016-2018 (1998); Han, M., Gao, X., Su, J. & Nie, S., Nat Biotechnol 19, 631-635 (2001); Griffin, T. & Smith, L., Trends Biotechnol 18, 77-84 (2000); Jackson, P., Scholl, P. & Groopman, J., Mol Med Today 6, 271-276 (2000); Haff, L. & Smimov, I., Genome Res 7, 378-388 (1997); Ross, P., Hall, L., Smirnov, I. & Haff, L., Nat Biotechnol 16, 1347-1351 (1998); Bray, M., Boerwinkle, E. & Doris, P. Hum Mutat 17, 296-304 (2001); Sauer, S. et al., Nucleic Acids Res 28, E13 (2000); Sauer, S. et al., Nucleic Acids Res 28, E100 (2000); Sun, X., Ding, H., Hung, K. & Guo, B., Nucleic Acids Res 28, E68 (2000); Tang, K. et al., Proc Natl Acad Sci USA 91, 10016-10020 (1999); Li, J. et al., Electrophoresis 20, 1258-1265 (1999); Little, D., Braun, A., O'Donnell, M. & Koster, H., Nat Med 3, 1413-1416 (1997); Little, D. et al. Anal Chem 69, 4540-4546 (1997); Griffin, T., Tang, W. & Smith, L., Nat Biotechnol 15, 1368-1372 (1997); Ross, P., Lee, K. & Belgrader, P., Anal Chem 69, 4197-4202 (1997); Jiang-Baucom, P., Girard, J., Butler, J. & Belgrader, P., Anal Chem 69, 4894-4898 (1997); Griffin, T., Hall, J., Prudent, J. & Smith, L., Proc Natl Acad Sci USA 96, 6301-6306 (1999); Kokoris, M. et al., Mol Diagn 5, 329-340 (2000); Jurinke, C., van den Boom, D., Cantor, C. & Koster, H. (2001); and/or Taranenko, N. et al., Genet Anal 13, 87-94 (1996).

The following additional genotyping methods are also encompassed by the present invention: the methods described and/or claimed in U.S. Pat. No. 6,458,540; and the methods described and/or claimed in U.S. Pat. No. 6,440,707.

Example 10

Method of Limiting the Risk of an HIV-1 Protease Inhibitor from Causing Metabolic Abnormalities in a Patient by Measuring Basal Resistin Levels The inventors hypothesis that some HIV-1 protease inhibitors may significantly elevate human resistin plasma/serum levels in patients. As described herein, this effect is believed to be representative of HIV-1 protease inhibitors that are also capable if inhibiting cathepsin D and cathepsin E. As a consequence of resistin being associated with obesity and insulin resistance, it is plausible to associate increased resistin plasma/serum levels both prior to or after administration of an HIV-1 protease inhibitor with an increased susceptibility to a patient in developing HIV-1 protease inhibitor-dependent metabolic abnormalities or related disorder upon the administration of a HIV-1 protease inhibitor. Therefore, the present invention encompasses the use of assays designed to measure resistin plasma/serum levels prior or in response to HIV-1 protease inhibitor exposure in patients to identify patients that may be at risk of developing HIV-1 protease inhibitor-dependent metabolic abnormalities.

Resistin may be assayed from patient samples essentially as described by Yagmor, et al., (Amer. J. Gastro., 101(6):1244 (2006)). Briefly, serum resistin concentrations can be determined using a quantitative sandwich enzyme immunoassay (ELISA), according to manufacturer's instructions (BioVendor, LLC, Candler, N.C., USA). Patient samples are stored at $-80°$ C. at time of collection and remain freezed up to the time of resistin measurement. To ensure assay maintains a linear measurement, human serum may be diluted in a range from 1:2 to 1:8, as necessary.

Generally, though any method capable of measuring the plasma/serum level of resistin would constitute a suitable method for identifying patients at increased risk of developing HIV-1 protease inhibitor-dependent metabolic abnormalities or related disorders. The lower the level of resistin, the lower the likelihood that a patient will develop HIV-1 protease inhibitor-dependent metabolic abnormalities.

Such an assay would also be useful for identifying levels of a given HIV-1 protease inhibitor compound in vivo that has a lower likelihood of inducing HIV-1 protease inhibitor-dependent metabolic abnormalities or related disorder in a patient. For example, it would be possible to identify a dose of a HIV-1 protease inhibitor compound using the above mentioned assay that induces lower levels of resistin plasma/serum levels, but that still has an acceptable level of efficacy.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the Sequence Listing submitted herewith and the corresponding computer readable form are both incorporated herein by reference in their entireties.

While this invention has been particularly shown and described with references to preferred embodiments thereof, it will be understood by those skilled in the art that various changes in form and details may be made therein without departing from the scope of the invention encompassed by the appended claims.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the Sequence Listing submitted herewith and the corresponding computer readable form are both incorporated herein by reference in their entireties.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a HIV-1 protease inhibitor compound having a decreased likelihood of inducing HIV-1 protease inhibitor-dependent metabolic abnormalities in a mammal comprising the step of:
   a) incubating resistin, with a cathepsin, in the presence of a test compound; and
   b) measuring the level of proteolyzed resistin;
wherein a diminished level or absence of proteolyzed resistin by the test compound relative to a control is indicative of a decreased probability said compound will cause HIV-1 protease inhibitor-dependent metabolic abnormalities in said mammal.

2. The method according to claim 1, wherein said cathepsin is cathepsin D.

3. The method according to claim 1, wherein said cathepsin is cathepsin E.

4. The method according to claim 1, wherein said resistin is denatured.

5. The method according to claim 4, wherein said resistin is denatured by alkylation.

6. The method according to claim 1, wherein the cysteine residues of said resistin are reduced.

7. The method according to claim 1, wherein said resistin is denatured by alkylation and the cysteine residues of said resistin are reduced.

8. The method according to claim 1, wherein said cathepsin is activated prior to incubation with resistin.

* * * * *